(12) United States Patent
Bingold et al.

(10) Patent No.: US 12,172,039 B2
(45) Date of Patent: Dec. 24, 2024

(54) BODY-WORN AIR-TREATMENT DEVICES AND METHODS OF DEACTIVATING PATHOGENS

(71) Applicant: Clear Blew, Portland, OR (US)

(72) Inventors: Joseph W. Bingold, Portland, OR (US); Ian D. Gates, Portland, OR (US); David S. D'Ascenzo, Portland, OR (US); Wyatt T. Weaver, Beaverton, OR (US)

(73) Assignee: Clear Blew, Portland, OR (US)

( * ) Notice: Subject to any disclaimer, the term of this patent is extended or adjusted under 35 U.S.C. 154(b) by 0 days.

(21) Appl. No.: 18/477,269

(22) Filed: Sep. 28, 2023

(65) Prior Publication Data

US 2024/0024711 A1    Jan. 25, 2024

Related U.S. Application Data

(62) Division of application No. 17/356,254, filed on Jun. 23, 2021, now Pat. No. 11,806,558.

(Continued)

(51) Int. Cl.
*A62B 23/00*    (2006.01)
*A61L 9/20*    (2006.01)
(Continued)

(52) U.S. Cl.
CPC .............. *A62B 23/00* (2013.01); *A61L 9/20* (2013.01); *A61N 1/32* (2013.01); *A61N 5/0603* (2013.01);
(Continued)

(58) Field of Classification Search
CPC .... A62B 7/00; A62B 7/10; A62B 9/00; A62B 9/06; A62B 18/00; A62B 18/02;
(Continued)

(56) References Cited

U.S. PATENT DOCUMENTS

| 5,103,813 | A | 4/1992 | Hart et al. |
| 5,165,395 | A | 11/1992 | Ricci |

(Continued)

FOREIGN PATENT DOCUMENTS

| AU | 2020100228 A4 | 3/2020 |
| AU | 2020100503 A4 | 5/2020 |

(Continued)

OTHER PUBLICATIONS

Ushio, "Care 222® in the Workplace: Testing Effectiveness of Long-Range Surface Infection Prevention": www.ushio.com/files/white-papers/ushio/care222-in-the-workplace-testing-effectiveness-of-long-range-surface-infection-prevention.pdf, downloaded May 28, 2020.

(Continued)

*Primary Examiner* — Colin W Stuart
(74) *Attorney, Agent, or Firm* — Kolitch Romano Dascenzo Gates LLC

(57) ABSTRACT

Body-worn air-treatment devices include a body that is configured to be selectively coupled proximate to a respiratory tract inlet of a living individual, and a pathogen-deactivating mechanism that is supported by the body. Methods include deactivating pathogens proximate to a respiratory tract inlet of a living individual.

22 Claims, 20 Drawing Sheets

Related U.S. Application Data

(60) Provisional application No. 63/044,966, filed on Jun. 26, 2020.

(51) Int. Cl.
  *A61N 1/32* (2006.01)
  *A61N 5/06* (2006.01)
  *A62B 9/06* (2006.01)
  *A62B 23/06* (2006.01)

(52) U.S. Cl.
  CPC .............. *A61N 5/0624* (2013.01); *A62B 9/06* (2013.01); *A62B 23/06* (2013.01); *A61L 2209/12* (2013.01); *A61N 2005/0606* (2013.01); *A61N 2005/0607* (2013.01); *A61N 2005/0627* (2013.01); *A61N 2005/0647* (2013.01); *A61N 2005/0661* (2013.01); *A61N 2005/0667* (2013.01)

(58) Field of Classification Search
  CPC ....... A62B 18/025; A62B 18/08; A62B 23/00; A62B 23/02; A62B 23/025; A62B 23/06; A41D 13/11; A41D 13/1192; A61L 9/20; A61L 9/18; A61L 2209/12; A61N 5/0624; A61N 2205/0607; A61N 2205/0661; A61N 2205/0667
  See application file for complete search history.

(56) References Cited

U.S. PATENT DOCUMENTS

| | | | |
|---|---|---|---|
| 6,681,765 | B2 | 1/2004 | Wen |
| 6,772,762 | B2 | 8/2004 | Piesinger |
| 7,036,502 | B2 | 5/2006 | Manne |
| 7,226,470 | B2 | 6/2007 | Kemeny et al. |
| 7,392,806 | B2 | 7/2008 | Yuen et al. |
| 7,823,586 | B2 | 11/2010 | Glazman |
| 8,574,331 | B2 | 11/2013 | Bangera et al. |
| 8,733,356 | B1 | 5/2014 | Roth |
| 9,095,704 | B2 | 8/2015 | McGuire |
| 10,201,198 | B2 | 2/2019 | Tong et al. |
| 10,335,618 | B2 | 7/2019 | Zhou et al. |
| 10,960,094 | B1* | 3/2021 | Ismail ............... A61M 16/0666 |
| 2005/0081849 | A1 | 4/2005 | Warren |
| 2005/0284470 | A1 | 12/2005 | Wei et al. |
| 2006/0182670 | A1 | 8/2006 | Allen |
| 2007/0175478 | A1 | 8/2007 | Brunst |
| 2007/0251526 | A1 | 11/2007 | Zocher |
| 2008/0065175 | A1 | 3/2008 | Redmond et al. |
| 2009/0007919 | A1 | 1/2009 | Dolezal et al. |
| 2009/0018485 | A1 | 1/2009 | Krespi et al. |
| 2010/0108071 | A1 | 5/2010 | Macy, Jr. |
| 2010/0222852 | A1 | 9/2010 | Vasily et al. |
| 2011/0126828 | A1 | 6/2011 | Wu et al. |
| 2012/0279503 | A1 | 11/2012 | Zhou et al. |
| 2013/0012869 | A1 | 1/2013 | Cha et al. |
| 2014/0290669 | A1* | 10/2014 | Ngo ..................... A63B 71/085 128/861 |
| 2015/0290471 | A1 | 10/2015 | McGuire |
| 2018/0064968 | A1 | 3/2018 | Taslagyan |
| 2018/0178031 | A1* | 6/2018 | Wu ........................ A61N 5/062 |
| 2018/0193660 | A1 | 7/2018 | DiMauro et al. |
| 2019/0015541 | A1 | 1/2019 | Peczalski |
| 2019/0240503 | A1 | 8/2019 | Friedman et al. |
| 2020/0215359 | A1 | 7/2020 | Yu et al. |
| 2021/0308407 | A1 | 10/2021 | Fitzgerald |
| 2021/0369431 | A1* | 12/2021 | Dreier .................. A61C 15/00 |
| 2021/0379425 | A1 | 12/2021 | Tran |

FOREIGN PATENT DOCUMENTS

| | | | |
|---|---|---|---|
| CN | 2616236 | Y | 5/2004 |
| CN | 2854874 | Y | 1/2007 |
| CN | 105988227 | A | 10/2016 |
| CN | 205649748 | U | 10/2016 |
| CN | 110882498 | A | 3/2020 |
| CN | 111096500 | A | 5/2020 |
| CN | 111135497 | A | 5/2020 |
| CN | 111150138 | A | 5/2020 |
| CN | 111165942 | A | 5/2020 |
| CN | 111194953 | A | 5/2020 |
| CN | 111202865 | A | 5/2020 |
| CN | 111214775 | A | 6/2020 |
| CN | 111228618 | A | 6/2020 |
| CN | 111228667 | A | 6/2020 |
| CN | 111249637 | A | 6/2020 |
| CN | 111317936 | A | 6/2020 |
| CN | 111329145 | A | 6/2020 |
| CN | 111450431 | A | 7/2020 |
| CN | 111514479 | A | 8/2020 |
| CN | 111602900 | A | 9/2020 |
| CN | 111632184 | A | 9/2020 |
| CN | 111657594 | A | 9/2020 |
| CN | 111752010 | A | 10/2020 |
| CN | 211794438 | U | 10/2020 |
| CN | 111938231 | A | 11/2020 |
| IL | 162597 | A | 5/2009 |
| IN | 201941004702 | A | 8/2020 |
| JP | 3148385 | U | 2/2009 |
| JP | 3154859 | U | 10/2009 |
| JP | 2011078488 | A | 4/2011 |
| JP | 4927199 | B2 | 5/2012 |
| KR | 20170000747 | U | 3/2017 |
| KR | 101851064 | B1 | 4/2018 |
| KR | 1020180032803 | A | 4/2018 |
| RU | 2404816 | C1 | 11/2010 |
| RU | 2729292 | C1 | 8/2020 |
| WO | WO96/11037 | A1 | 4/1996 |
| WO | WO2005060366 | A2 | 7/2005 |
| WO | WO2014059675 | A1 | 4/2014 |
| WO | WO2017128501 | A1 | 8/2017 |
| WO | WO2020026472 | A1 | 2/2020 |

OTHER PUBLICATIONS

Cantor, Carla, "Could a New Ultraviolet Technology Fight theSpread of Coronavirus?", Columbia News: https://news.columbia.edu/ultraviolet-technology-virus-covid-19-UV-light; Apr. 1, 2020.

Buonanno, Manuela et al. "Far-UVC light efficiently and safely inactivates airborne human coronaviruses", Apr. 27, 2020, Preprint (Version 1) available at Research Square: https://doi.org/10.21203/rs.3.rs-25728/v1.

Bukszpan, Daniel, "This former NASA scientist wants to fight coronavirus with ultraviolet light", CNBC: https://www.cnbc.com/2020/05/07/former-nasa-scientist-wants-to-fight-coronavirus-with-ultraviolet-light.html; May 7, 2020.

Kobe University, "Repetitive irradiation with 222nm UVC non-carcinogenic, safe for sterilizing human skin", Phys.Org: https://phys.org/news/2020-04-repetitive-irradiation-222nm-uvc-non-carcinogenic.html; Apr. 7, 2020.

* cited by examiner

FIG. 1

BODY-WORN AIR-TREATMENT DEVICE 10

- BODY 12
  - FIRST BODY PART 18
    - FIRST RESILIENT MATERIAL 22
    - OUTERMOST/EXTERNAL DIMENSION 30
    - ADHESIVE SURFACE 38
    - ADHESIVE 40
    - CAVITY 46
    - HEAD MOUNT 98
    - SUPPORT 99
  - SUB-PORTION(S) 65
    - PROJECTION 67
  - SECOND BODY PART 20
    - SECOND RESILIENT MATERIAL 24
    - LONGITUDINAL AXIS 32
    - LIGHT TRAP 60
    - CIRCUITOUS PATHWAY 62
    - BAFFLES 63
    - BACKING 42
    - ANTIMICROBIAL MATERIAL 52
    - BAND 44
  - RESILIENT MATERIAL 16
    - END REGIONS 26
    - VOID 28
    - END REGIONS 72
    - MAGNETIC ASSEMBLY 33
    - MAGNET 34
    - FERROMAGNETIC ELEMENT 36
    - INWARD SURFACE 64
    - COVERING 70
  - TETHER 50
  - ANCHOR 48

- POWER SOURCE 82
  - BATTERY(IES) 84
- CHARGING PORT 66
- CONTROLLER 85
- USER CONTROL 86
- WIRELESS TRANSCEIVER 88
- INDICATOR 94
- DISPLAY 96
- INTERNAL SWITCH 53
- WIRED CONNECTION PORT 90
- MEDIA 92

- PATHOGEN-DEACTIVATING MECHANISM 14
  - CURTAIN 55
  - ELECTRODES 81
  - ELECTRIC FIELD 77
  - STRUCTURE(S) 59
  - LENS(ES) 56
  - REFLECTOR(S) 58
  - LIGHT SOURCE(S) 54
  - LED(S) 76
  - LIGHT FILTER 74
  - ELECTROCEUTICAL FABRIC 78
  - PLIES 80

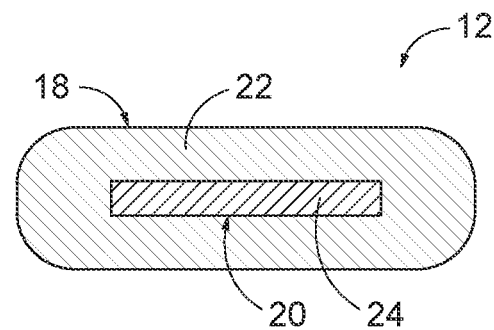
FIG. 3
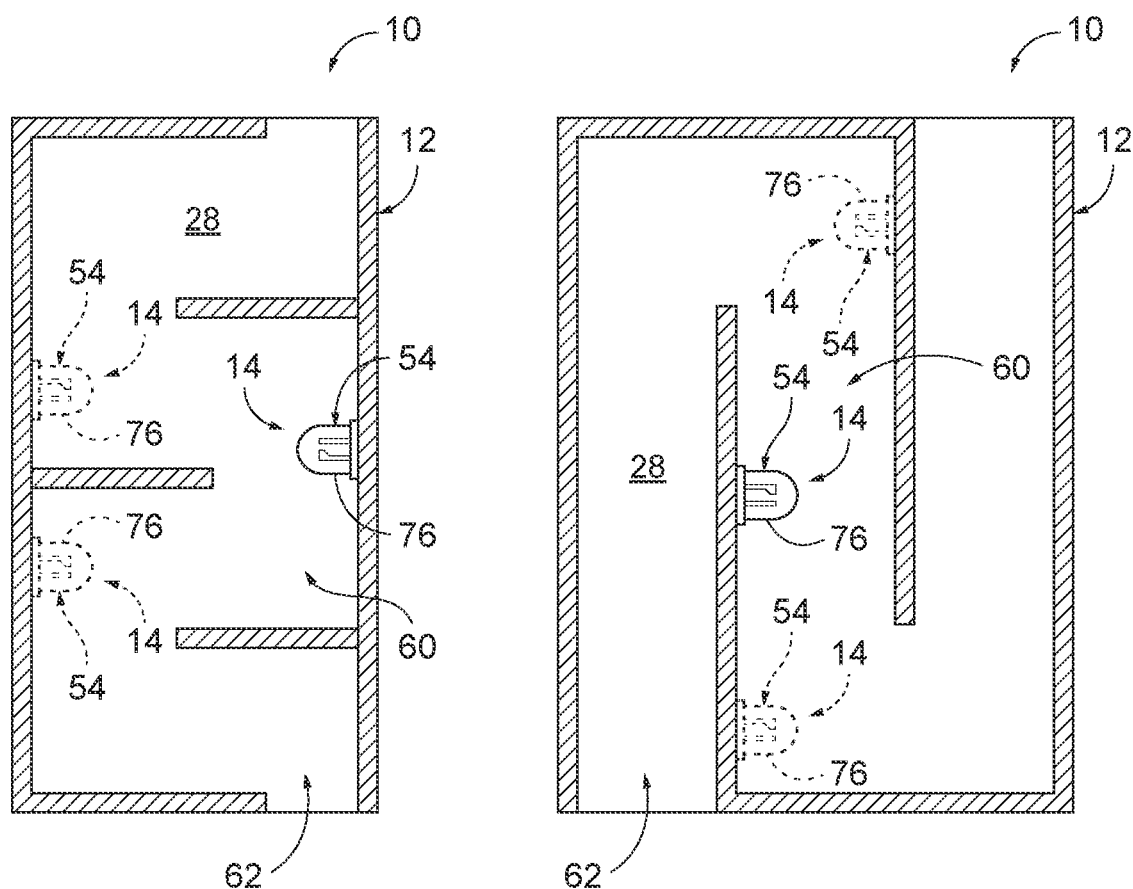
FIG. 4
FIG. 5

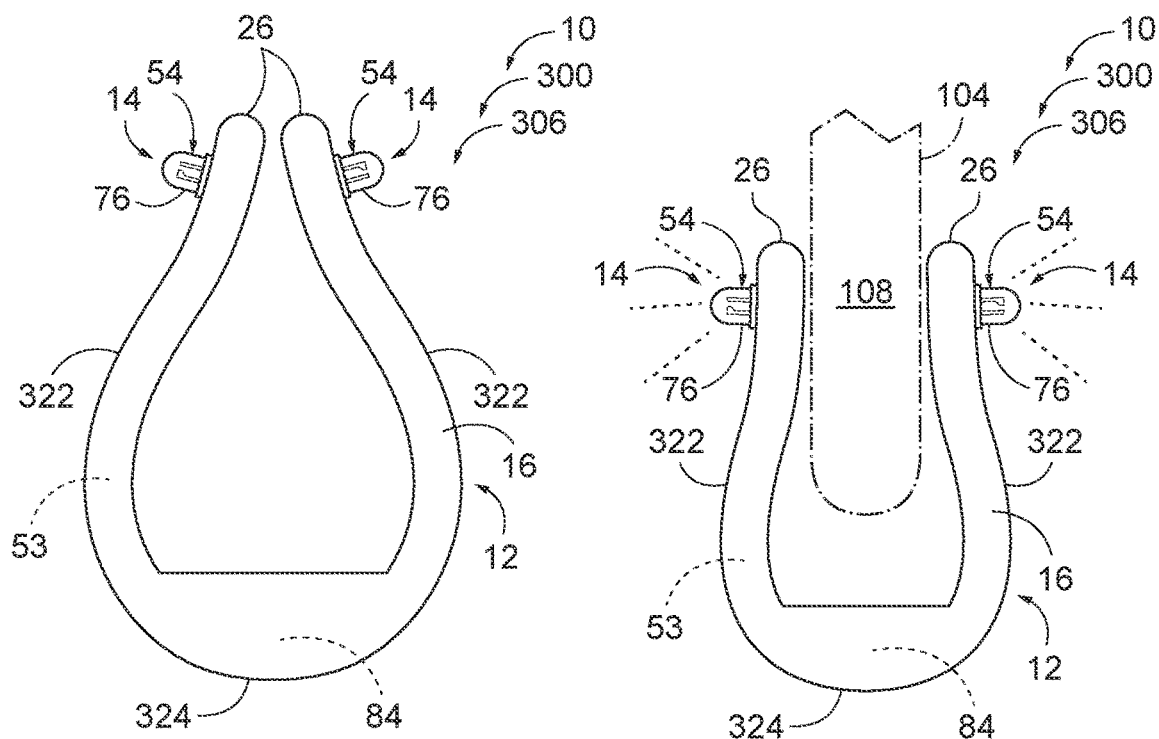
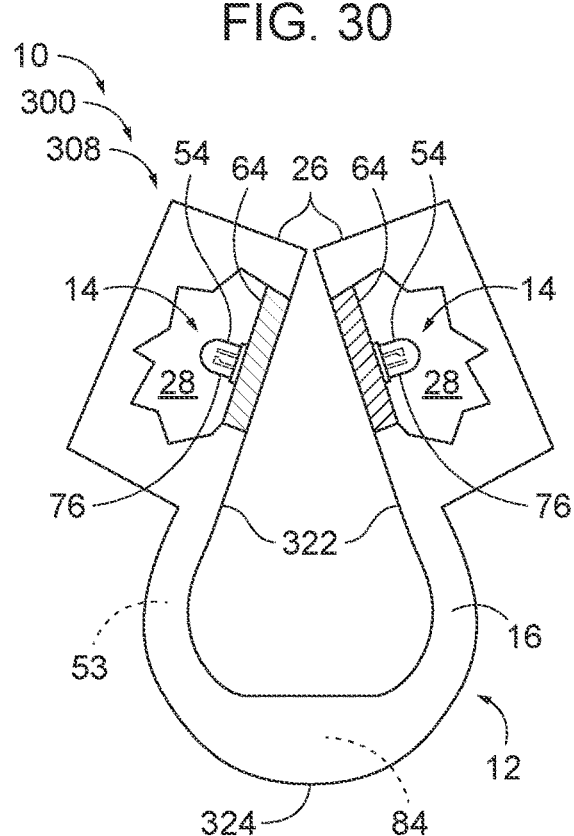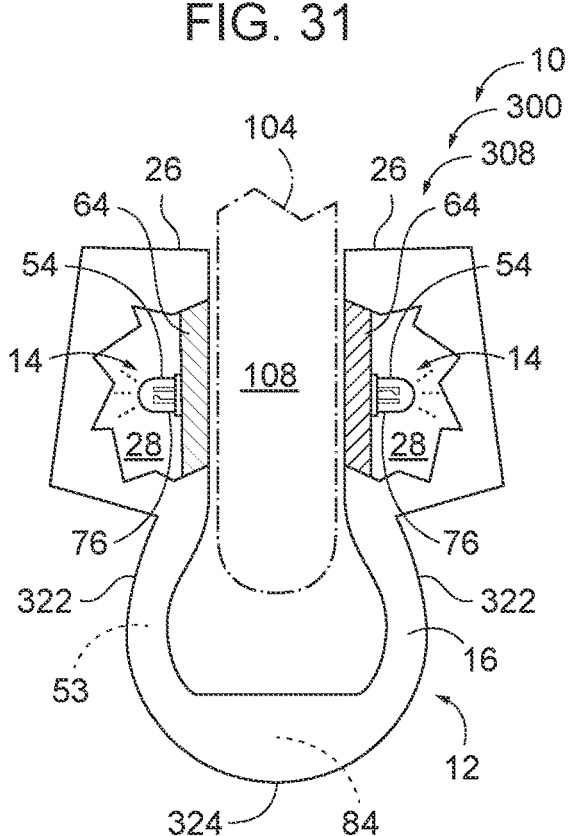
FIG. 30  FIG. 31  FIG. 32  FIG. 33

BODY-WORN AIR-TREATMENT DEVICES AND METHODS OF DEACTIVATING PATHOGENS

RELATED APPLICATIONS

The present application is a divisional of U.S. patent application Ser. No. 17/356,254, which was filed on Jun. 23, 2021, and which claims priority to U.S. Provisional Patent Application No. 63/044,966, which was filed on Jun. 26, 2020, and the complete disclosures of which are hereby incorporated by reference.

FIELD

The present disclosure relates to body-worn air-treatment devices, to uses thereof, and to methods of deactivating pathogens.

BACKGROUND

Living individuals may contract diseases via a variety of mechanisms, or contamination paths. One such way is via inhalation of pathogens into the living individual's respiratory tract, such as via the living individual's nose or mouth. In a similar manner, infected individuals may spread disease to other living individuals and/or contaminate objects with pathogens by exhaling air that contains the pathogens. Proper sanitation of objects and frequent handwashing may help reduce the likelihood of such pathogens being inhaled by a living individual, but conventional solutions are limited, such as to prevent the actual inhalation or exhalation of pathogens by a living individual. Masks and face shields may be utilized to provide physical barriers proximate to the inlets to the living individual's respiratory tract, but such physical barriers do not deactivate pathogens and may even become a carrier or accumulator of active pathogens. Accordingly, there exists a need for effective, body-worn air-treatment devices for deactivating pathogens, and especially for deactivating pathogens proximate to an inlet to a living individual's respiratory tract.

SUMMARY

Body-worn air-treatment devices and related methods are disclosed herein. The devices comprise a body that is configured to be selectively coupled proximate to a respiratory tract inlet of a living individual, and a pathogen-deactivating mechanism that is supported by the body. The methods comprise deactivating pathogens proximate to a respiratory tract inlet of a living individual.

BRIEF DESCRIPTION OF THE DRAWINGS

FIG. 1 is a schematic diagram representing examples of body-worn air-treatment devices.

FIG. 3 is a schematic cross-sectional view representing example bodies of body-worn air-treatment devices.

FIG. 4 is a schematic cross-sectional view representing example body-worn air-treatment devices.

FIG. 5 is a schematic cross-sectional view representing example body-worn air-treatment devices.

FIG. 30 is a schematic illustration representing example nose-mounted air-treatment devices, shown in a sprung conformation.

FIG. 31 is a schematic illustration representing the example nose-mounted air-treatment devices of FIG. 30, shown conformed to or toward a flexed conformation.

FIG. 32 is a schematic illustration representing example nose-mounted air-treatment devices, shown in a sprung conformation.

FIG. 33 is a schematic illustration representing the example nose-mounted air-treatment devices of FIG. 32, shown conformed to or toward a flexed conformation.

DESCRIPTION

Figure 2:
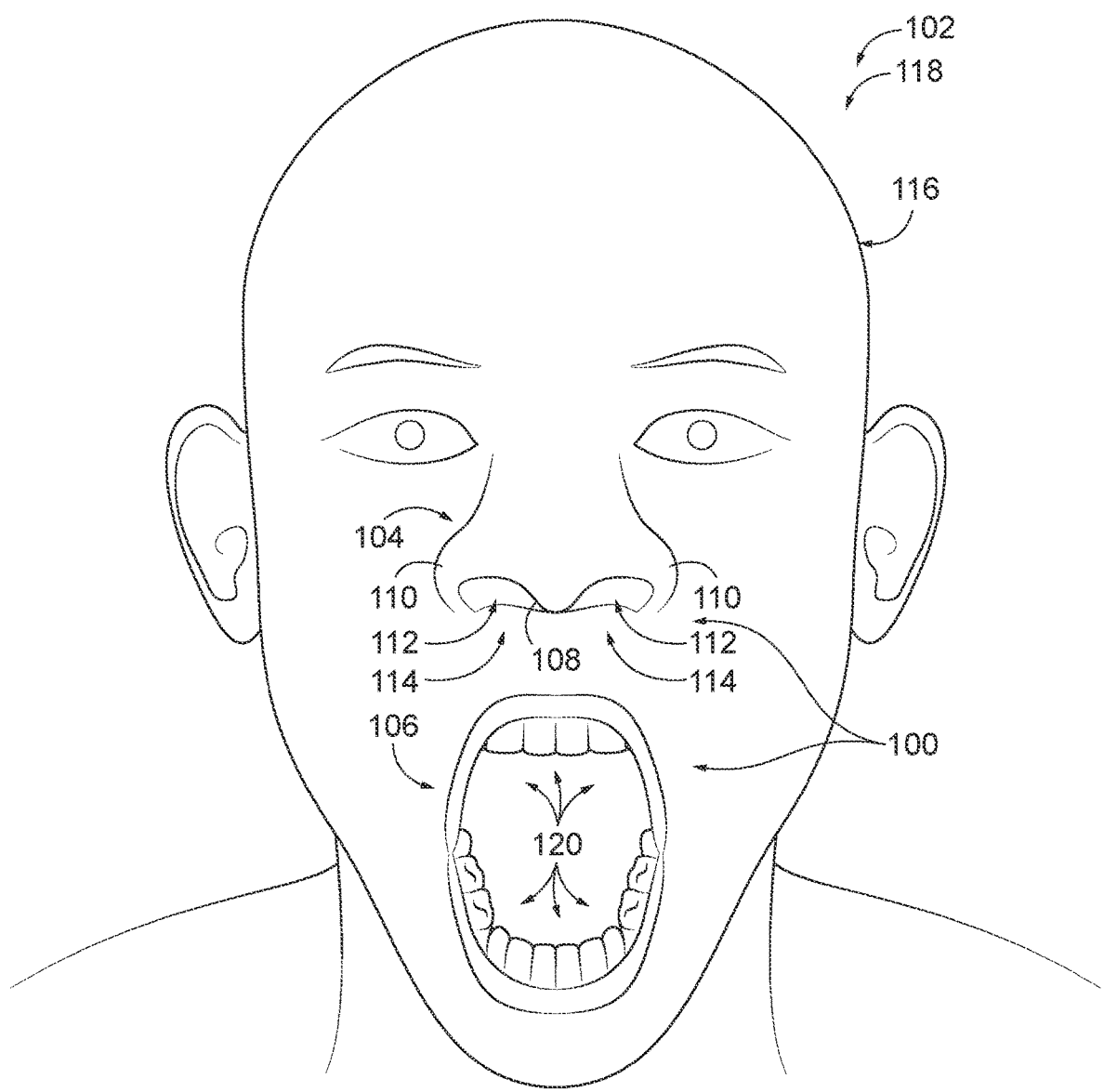
FIG. 2 is a schematic representation of an example living individual that may wear a body-worn air-treatment device.
Figure 52:
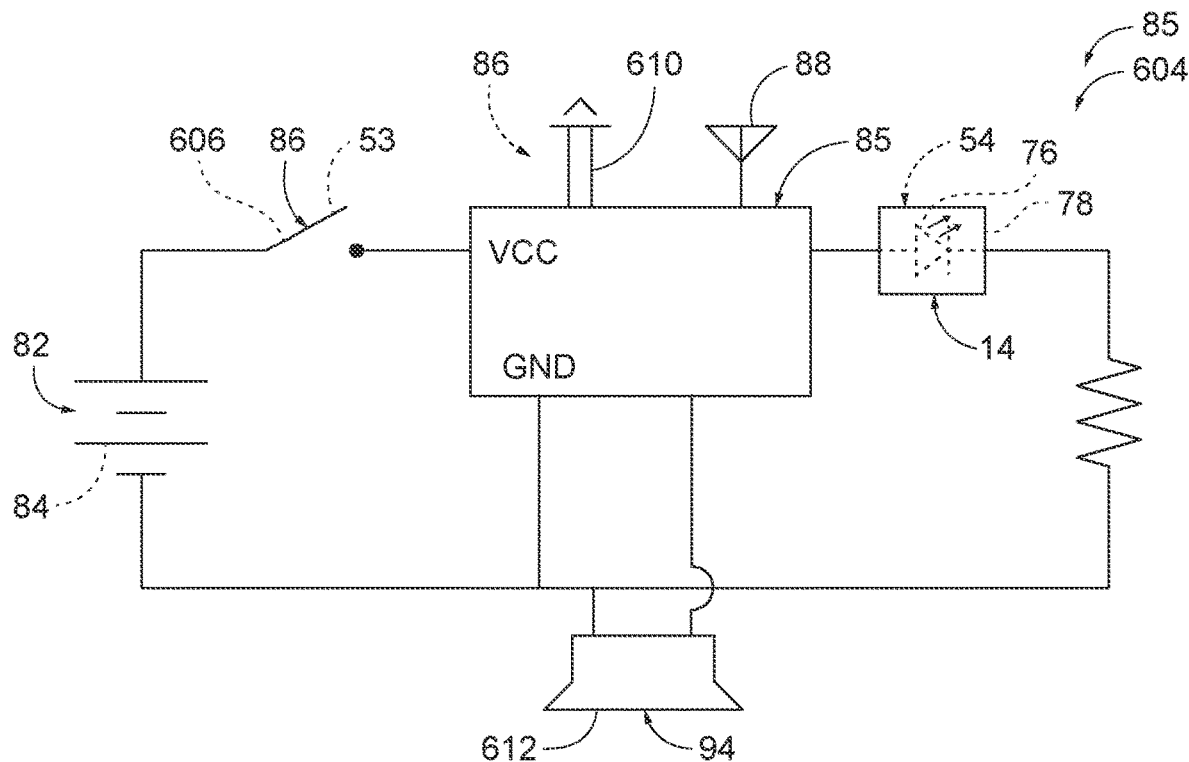
FIG. 52 is another schematic circuit diagram representing example electronics of body-worn air-treatment devices.
Figure 53:
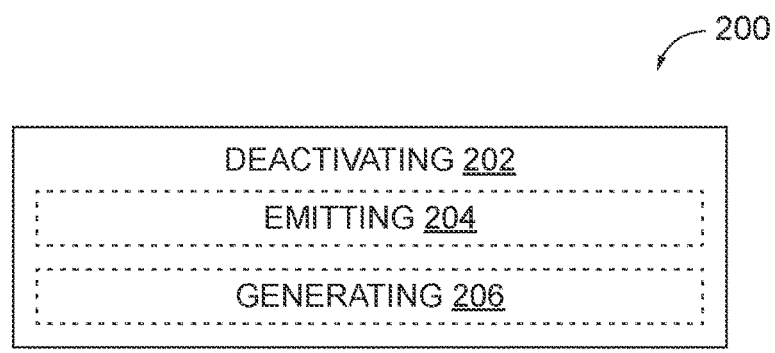
FIG. 53 is a flowchart schematically representing methods of deactivating pathogens.

FIG. 1 schematically represents body-worn air-treatment devices 10 according to the present disclosure, FIG. 2 schematically represents a living individual 102 that may wear, or don, a body-worn air-treatment device 10, FIGS. 3-52 less schematically illustrate examples of body-worn air-treatment devices 10 and/or portions thereof, and FIG. 53 schematically represents methods of deactivating pathogens. While FIG. 2 schematically illustrates an example of a living individual 102 in the form of a human 118, body-worn air-treatment devices 10 also may be used and/or configured to be used with non-human animals. Generally in the figures, elements that are likely to be included in a given example or embodiment are illustrated in solid lines, while elements that are optional to a given example or embodiment are illustrated in dashed lines. However, elements that are illustrated in solid lines are not essential to all examples or embodiments of the present disclosure, and an element shown in solid lines may be omitted from a particular example or embodiment without departing from the scope of the present disclosure. Where appropriate, the reference numerals from the schematic diagram of FIG. 1 are used to designate corresponding parts of the examples of FIGS. 3-52; however, the examples of FIGS. 3-52 are non-exclusive and do not limit body-worn air-treatment devices 10 to the illustrated embodiments of FIGS. 3-52. That is, body-worn air-treatment devices 10 are not limited to the specific examples of FIGS. 3-52, and body-worn air-treatment devices 10 may incorporate any number of the various aspects, configurations, characteristics, properties, etc. of body-worn air-treatment devices 10 that are illustrated in and discussed with reference to the schematic diagram of FIG. 1 and/or the examples of FIGS. 3-52, as well as variations thereof, without requiring the inclusion of all such aspects, configurations, characteristics, properties, etc. For the purpose of brevity, each component, part, portion, aspect, region, etc. or variants thereof discussed in connection with FIG. 1 may not be discussed, illustrated, and/or labeled again with respect to FIGS. 3-52; however, it is within the scope of the present disclosure that the features, variants, etc. discussed in connection with FIG. 1 may be utilized with any suitable example or embodiment according to the present disclosure.

As schematically represented in FIG. 1, body-worn air-treatment devices 10 comprise at least a body 12 and a pathogen-deactivating mechanism 14. Body-worn air-treatment devices 10 additionally or alternatively may be referred to herein as air-purifying devices 10, pathogen-deactivating devices 10, air-treatment devices 10, or simply as devices 10. The body 12 is configured to be selectively coupled proximate a respiratory tract inlet 100 of a living individual 102, and the pathogen-deactivating mechanism 14 is supported by the body 12. Accordingly, when the body 12 is coupled proximate a respiratory tract inlet 100 (illustrated in FIG. 2) of a living individual 102, the pathogen-deactivating mechanism 14 is positioned to deactivate pathogens as they enter and/or exit the respiratory tract inlet 100. In some examples, the pathogen-deactivating mechanism 14 may be described as an active pathogen-deactivating mechanism 14 and/or as being configured to actively deactivate pathogens as they enter and/or exit the respiratory tract inlet 100. An active pathogen-deactivating mechanism 14 may be described as a pathogen-deactivating mechanism that requires electricity and/or that generates an emission (e.g., light or an electric field) to operatively function. Passive pathogen-deactivating mechanisms 14 and/or pathogen-deactivating mechanisms 14 with a passive deactivating component or element also are within the scope of the present disclosure, such as examples where one or more components of a body-worn air-treatment device 10 are constructed of an antimicrobial material, as discussed herein. In some examples, a body-worn air-treatment device 10 may be described as an intra-body-worn air-treatment device 10, in that the device itself or at least a portion thereof is positioned within the living individual's body when operatively donned. However, as disclosed herein, this is not required of all body-worn air-treatment devices 10 according to the present disclosure.

The body 12 additionally or alternatively may be referred to herein as the housing 12, the frame 12, the hub 12, and/or the shell 12 of the device 10. The pathogen-deactivating mechanism 14 additionally or alternatively may be referred to herein as the pathogen-deactivating assembly 14, the pathogen-deactivating components 14, the pathogen-deactivating circuit 14, and/or the pathogen-deactivating module 14 of the device 10. As used herein, references to the pathogen-deactivating mechanism 14 or another component of the device 10 being supported by the body 12 include the pathogen-deactivating mechanism 14 or other component being at least one of housed within, encapsulated within, secured to, coupled to, embedded within, extending from, positioned by, protected by, shielded by, embodied within, adhered to, formed within, mounted upon, and/or mounted within the body 12.

With reference to FIG. 2, respiratory tract inlets 100 include the threshold (i.e., nasal nostril inlet) to the nose 104 and the threshold (i.e., lips) to the mouth 106 of a living individual 102, and as used herein, "proximate a respiratory tract inlet 100" means at, within, at least partially within, extending at least partially into, inserted within, installed within, projecting at least partially from, adjacent to (e.g., within a threshold distance 150 (illustrated in FIGS. 48-49) of) the threshold to the nose 104 or the threshold to the mouth 106 of a living individual 102. Respiratory tract inlets 100 also may be described as respiratory tract outlets or thresholds 100. Examples of the threshold distance 150 include at most 20 centimeters (cm), at most 15 cm, at most 10 cm, at most 5 cm, at most 2.5 cm, 0-40 cm, 0-30 cm, 0-20 cm, 0-10 cm, 0-5 cm, 0.1-30 cm, 0.1-20 cm, 0.1-10 cm, 0.1-5 cm, 0.5-15 cm, 0.5-10 cm, and/or 0.5-5 cm.

Examples of pathogens include bacteria, viruses, and other microorganisms that cause disease in living individuals 102. As used herein, "deactivate," "deactivating," and/or "deactivation of" pathogens means the rendering of pathogens ineffective or at least less effective in causing associated diseases in living individuals 102. For example, deactivation may include one or more of damaging the DNA and/or RNA of the pathogens, killing the pathogens, disrupting a membrane of the pathogens, rendering the pathogens unable to reproduce, etc. "Deactivate", "deactivation," and "deactivating" additionally or alternatively may be referred to as "inactivate," "inactivation," and "inactivating."

Accordingly, body-worn air-treatment devices 10 are configured to be worn by a living individual 102 so that pathogens entering and/or exiting the living individual's respiratory tract inlet 100 become deactivated and thus unable, or at least less likely to, cause disease in the living individual 102 or others.

In some examples of devices 10, the pathogen-deactivating mechanism 14 comprises at least one light source 54 that is supported by the body 12 and that is configured to emit light within a germicidal spectrum, such as UV light (i.e., light having a wavelength in the range of 100 to 400 nanometers (nm)). UVC light (i.e., light having a wavelength in the range of 100 to 280 nm) is generally considered to be germicidal because it disrupts DNA base pairing, causing formation of pyrimidine dimers, and leads to the inactivation of bacteria, viruses, and protozoa. In some examples, a light source 54 is configured to emit light solely within the germicidal spectrum, or within the UVC range. Additionally or alternatively, a light source 54 may be configured to not emit any light within the visible spectrum. Accordingly, in such an example, when a device 10 is worn and used, the light source 54 will not be visible to the living individual 102 or others. For example, in a nose-mounted embodiment, the living individual's nose will not glow or otherwise be illuminated, and similarly in mouth-mounted embodiments, the living individual's mouth will not glow or otherwise be illuminated. Moreover, in such examples, visible light will not be emitted from the corresponding respiratory tract inlet.

A desired spectrum of emitted light may be accomplished by selecting a specific type or configuration of light source 54 and/or by filtering the light emitted by a light source 54. In some examples of devices 10, the light source 54 comprises a light filter 74, such as that is selected to restrict unwanted spectrums of light from being emitted from the light source 54.

For example, and as discussed herein, in some examples or embodiments it may be desirable to filter out (i.e., restrict or prevent) visible light from being emitted. Additionally or alternatively, in some examples, it may be desirable to avoid and/or filter out (i.e., block) light that damages human tissue, such as light within the UVA spectrum, within the UVB spectrum, or within the near UVC spectrum. In some examples, the light source 54 is configured to emit light within the far UVC range (205-230 nm) and optionally solely within the far UVC range. In some such examples, the light has a wavelength of 222 nm, and optionally a substantial portion of or optionally all of the light has a wavelength of 222 nm. The light source 54 may include at least one light, or light-emitting structure, with examples including bulbs and LEDs 76. In some examples, a preferred light source 54 is one or more LEDs 76.

In some examples of devices 10, a light source 54 may be configured to emit light within at least one, and optionally both, nostrils 112 of a nose 104 of a living individual 102 when the body 12 is operatively coupled relative to the nose 104. In some such examples, a light source 54 may be configured to emit the light primarily, and optionally solely, within a single nostril 112 when the body 12 is operatively coupled relative to the nose 104, as opposed to a device in which a light source 54 is positioned external of a nose 104 and is configured to direct light into both nostrils 112 of a living individual. Each of the example nose-mounted devices 300 of FIGS. 15-29, 34-35, and 38-41 are examples of such devices 10 that include a light source 54 that emits light primarily within a single nostril 112. Some devices 10 comprise more than one light source 54, with a first light source 54 that is configured to emit light primarily, and optionally solely, within a first nostril 112, and a second light source 54 that is configured to emit light primarily, and optionally solely, within a second nostril 112 when the body 12 is operatively coupled relative to the nose 104. Each of example nose-mounted devices 306, 308, and 314 of FIGS. 30-33 and 36-37 are examples of such devices 10.

In some devices 10 that comprise one or more light sources 54, the body 12 at least partially, and optionally at least substantially or completely, defines a void 28 that is and/or extends inward, optionally radially inward, from an exterior, or exterior surface, of the body 12. In some such embodiments, the at least one light source 54 may be supported by the body 12 in a position such that when a light source 54 is activated, the light is directed to an entirety of the void 28. Accordingly, when the device 10 is operatively donned by a living individual 102, all air passing through the void 28 as a result of the living individual's breathing will be impinged by the light and thus the pathogens therein deactivated by the device 10. In some such examples, the body 12 may be sized, shaped, and/or otherwise configured to abut, extend against, and/or form an at least partial, if not complete, barrier to air flow against the corresponding portion of the respiratory tract inlet 100, such as a nostril 112, so that all air flowing through the nostril must flow through the void, and thus be impinged by the light and thus deactivated by the device 10. Each of example nose-mounted devices 310, 302, and 304 of FIGS. 15-20 are examples of such devices 10.

The void 28 additionally or alternatively may be described as an air passage 28, a deactivation passage 28, and/or a treatment passage 28. In some devices 10, the device 10 defines, or bounds, the entire perimeter of the void (i.e., the surface of the void that extends between the void's inlet and outlet), and such a void may be referred to as a closed void. The devices 10 of FIGS. 3-7, 9-12, 15-18, and 20 are examples of devices 10 that define a void 28 in the form of a closed void. In some devices 10, the body 12 may be sized, shaped, and/or otherwise configured such that the body 12 together with a portion of the living individual's tissue (e.g., the inside surface of a nostril 112) defines the void 28, and collectively forms a barrier to air flow against the corresponding portion of the respiratory tract inlet 100, such as a nostril 112, so that all air flowing through the nostril must flow through the void, and thus be impinged by the light and thus deactivated by the device 10. In such examples, the void 28 may be described as an open void. Each of example nose-mounted devices 304 and 330 of FIGS. 19-29 are examples of such devices 10.

In some devices 10 that comprise one or more light sources 54, the light source(s) 54 is/are configured to emit a curtain 55 of light proximate to a nasal cavity 114 and/or is mouth 106 of a living individual 102 when the body 12 is operatively coupled proximate to the respiratory tract inlet 100 of the living individual 102. As used herein, a curtain 55 of light, or light curtain 55, is or includes a volume in space, through which the light emitted when the light source(s) 54 shines, with the volume having at least one side that defines a boundary of the light curtain. For example, such a light curtain 55 may have a proximal boundary and/or a distal boundary generally spaced in front of the face of the living individual 102 wearing the device, so that the light shines within at least a threshold distance proximal the living individual's face so that the mechanism 14 may deactivate pathogens entering or exiting the inlets of the living individual's respiratory tract. In examples where a proximal boundary (i.e., adjacent to the living individual's face) is defined, the light curtain 55 therefore does not impinge on the living individual's facial tissue, avoiding damage thereto in examples where the emitted light is within a spectrum that potentially damages human tissue (e.g., UVA, UVB, and near UVC). In examples where a distal boundary (i.e., distal from the living individual's face) is defined, the light curtain 55 therefore does not shine away from the living individual in an undesirable direction, such as toward other individuals in proximity to the living individual 102 wearing the device 10. Some such devices 10 further comprise one or more structures 59 (e.g., lenses 56 and/or reflectors 58) that are supported by the body 12 and/or that are defined by the body 12 relative to the light source(s) 54 and that are configured to direct the light as the light curtain 55, such as to define the boundaries thereof. The dimensions, boundaries, and shape of a light curtain 55 may vary depending on the properties of the light source 54 and/or on the type of light emitted therefrom. In some examples, a thin light curtain may be desired to avoid impingement of light on the living individual's tissue and to avoid the light impinging on others or objects in the vicinity of the living individual. In other examples, a wider light curtain may be desired to increase the exposure time that air (and thus pathogens) experiences as the air passes through the light curtain.

Figure 6:
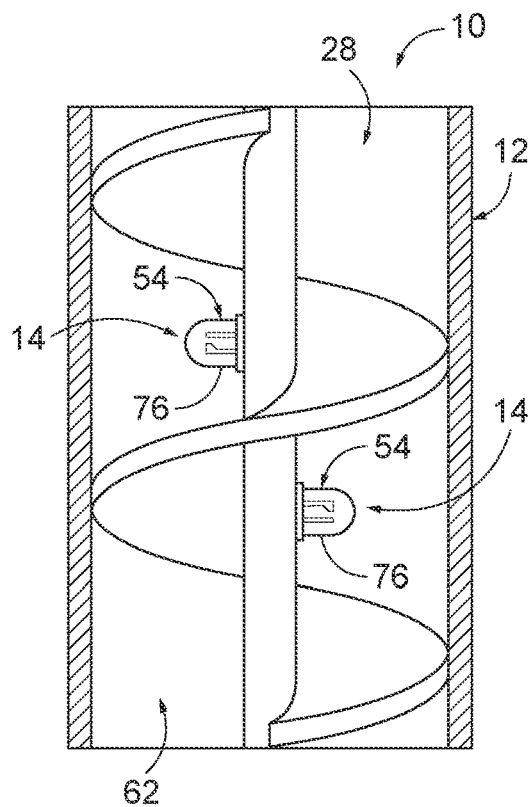
FIG. 6 is a schematic cross-sectional view representing example body-worn air-treatment devices.

In some devices 10 that comprise one or more light sources 54, the light source(s) 54 is/are supported by the body 12 such that the body 12 shields tissue of the living individual 102 from the light emitted by the light source(s) 54 when the body 12 is operatively coupled proximate to the respiratory tract inlet 100 of the living individual 102. For example, in examples where the light source 54 emits light within a spectrum (e.g., UVA, UVB, or near UVC) that potentially damages human tissue, the body 12 will prevent such damage by shielding tissue from impingement by the emitted light. The schematic examples of bodies 12 in at least FIGS. 4-6 provide such functionality.

Additionally or alternatively, in some devices 10 that comprise one or more light sources 54, the body 12 is shaped to shield tissue of the living individual 102 from the light when the body 12 is operatively coupled proximate to the respiratory tract inlet 100 of the living individual 102. For example, in some such devices 10, the body 12 defines the void 28, and the light source(s) 54 is/are configured to emit light solely within the void 28. Additionally or alternatively, in some examples, the body 12 defines a light trap 60, and the light source(s) 54 is/are configured to emit light solely within the light trap 60. At least FIGS. 4-6 schematically illustrate examples of bodies 12 that define light traps 60.

Additionally or alternatively, the body 12, and optionally the void 28 extending therein, may define a circuitous pathway 62, through which air (e.g., a living individual's breath) is permitted to flow when the body 12 is operatively coupled proximate to the respiratory tract inlet 100 of the living individual 102, and with the light source(s) 54 being configured to emit light throughout at least a substantial portion of the circuitous pathway 62. FIGS. 4-6 schematically illustrate examples of bodies 12 that define circuitous pathways 62. In some examples, the circuitous pathway 62 is fully within or substantially within a nostril 112 of a living individual 102 when the body 12 is operatively coupled proximate to the respiratory tract inlet 100 of the living individual 102. In other examples, the circuitous pathway 62 may extend within and outside of a nostril 112 of a living individual 102 when the body 12 is operatively coupled proximate to the respiratory tract inlet 100 of the living individual 102. When provided, the circuitous pathway 62 may define a light trap 60, as discussed above. Also, the circuitous pathway 62 enables a longer exposure time for air passing through the body 12 when a living individual 102 donning the device is breathing, thereby increasing the effectiveness of the pathogen-deactivating function of the pathogen-deactivating mechanism 14.

Additionally or alternatively, the body 12 may define a plurality of baffles 63 extending into or otherwise positioned within the void 28. When present, the baffles 63 are configured to cause air flow through the void 28 to be disrupted or otherwise turbulent such that the air passing through the void 28, when a living individual 102 donning the device is breathing, has a longer exposure time from the pathogen-deactivating mechanism 14 compared to a similarly structured device without the baffles 63. Accordingly, in such devices 10, the effectiveness of the pathogen-deactivating function of the light source(s) 54 is increased. The baffles 63, when present, optionally may define a circuitous pathway 62. When present, the baffles 63 may take any suitable configuration such that they disrupt the air flow and cause a longer exposure time. As examples, the baffles 63 may comprise ridges or ribs extending from and/or between one or more surfaces (e.g., inward surface(s) 64) of the body 12. The baffles 63 may be shaped, positioned, and/or oriented to optimally disrupt the air flow but without making breathing by a user restrictive or difficult. In some examples, the baffles 63 may have terminal ends that extend generally or partially in the direction of air flow so that the air is directed away from the bulk flow direction of the air flow. In some such examples, a subset of the baffles 63 may extend toward the opening to the void 28 that faces away from the user and a subset of the baffles 63 may extend toward the opening to the void 28 that faces within the user. The example nose-mounted device 330 of FIGS. 21-29 is an example of such devices 10 having two subsets of baffles 63 with terminal ends that respectively extend into the opposing directions of air flow and that are curved away from the directions of air flow so that the air flow is suitably disrupted to increase exposure time by the light source 54.

In some devices 10 that comprise one or more light sources 54, and in which the body 12 at least partially defines the void 28, the body 12 may include an inward, or interior, surface 64 that faces the void 28, with the inward surface 64 being reflective, so as to concentrate the light emitted by the light source(s) 54 within the void, through which air passes, and thus to increase the effectiveness of the pathogen-deactivating function of the light source(s) 54. As examples, the inward surface 64 may have a reflectance of at least 20%, at least 40%, at least 60%, or at least 80% for the light emitted by the light source(s) 54 and/or at least for a desired subset of the spectrum of the light emitted by the light source(s) 54 (e.g., for far UVC light).

In some devices 10 that comprise one or more light sources 54, and in which the body 12 at least partially defines the void 28, the body 12 comprises a covering 70 that extends across the void 28, with the covering 70 being configured to permit air flow therethrough. Such a covering 70 therefore may serve as a light filter to restrict passage of certain wavelengths of light and/or as an air filter to filter out particles within the air, as a user breathes through the void 28. For example, covering 70 may be configured to restrict passage of visible light therethrough, so when operatively donned and used by a living individual, visible light will not be emitted from the living individual's nose or mouth, depending on the type of device 10. Additionally or alternatively, in some examples, the covering 70 is further configured to restrict passage of UV light therethrough. Accordingly, in examples where the light source(s) 54 emit(s) portions of the UV spectrum that may damage human tissue, those portions of the UV spectrum may be filtered out by the covering 70, so as to avoid unintended damage to human tissue. For example, the covering 70 may be configured to restrict passage of UV light outside of the far UVC range therethrough.

Figure 7:
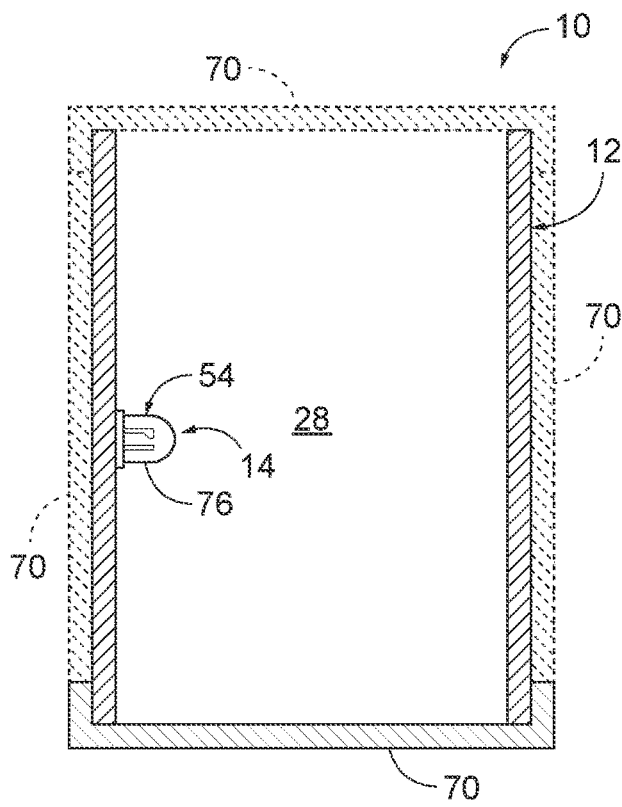
FIG. 7 is a schematic cross-sectional view representing example body-worn air-treatment devices.

In some examples of devices 10 that comprise a covering 70 and whose body defines the void 28, the void 28 has first and second longitudinally spaced end regions 72, and the covering 70 extends across one of the first and the second longitudinally spaced end regions 72. In other examples, the covering 70 extends across both of the first and the second longitudinally spaced end regions 72. In some examples, the covering encapsulates the body 12. FIG. 7 schematically illustrates such optional examples.

Figure 10:
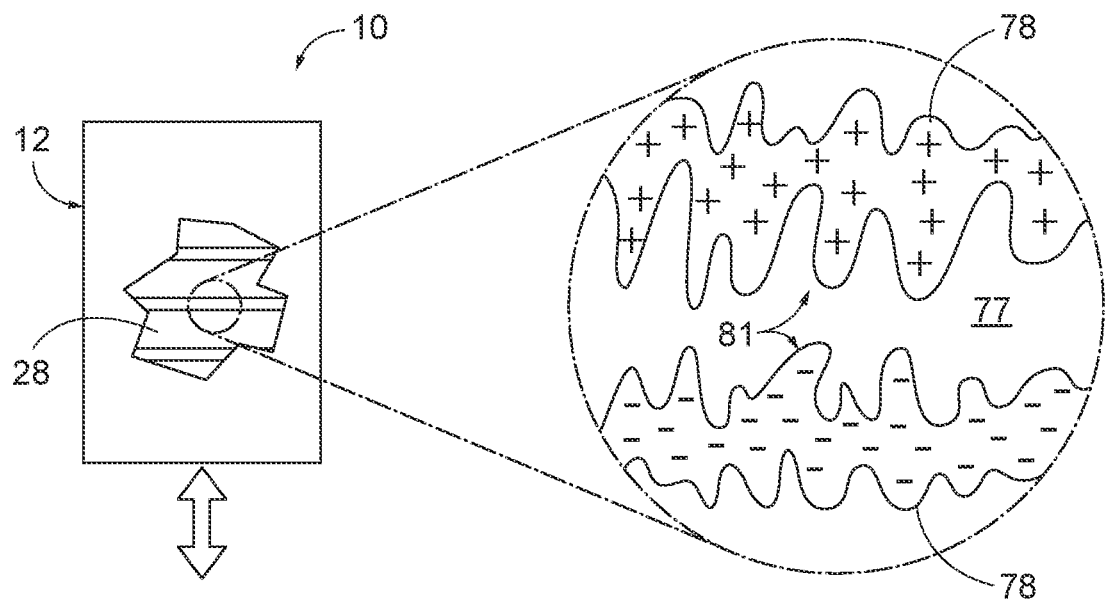
FIG. 10 is a schematic detailed view representing example body-worn air-treatment devices.
Figure 11:
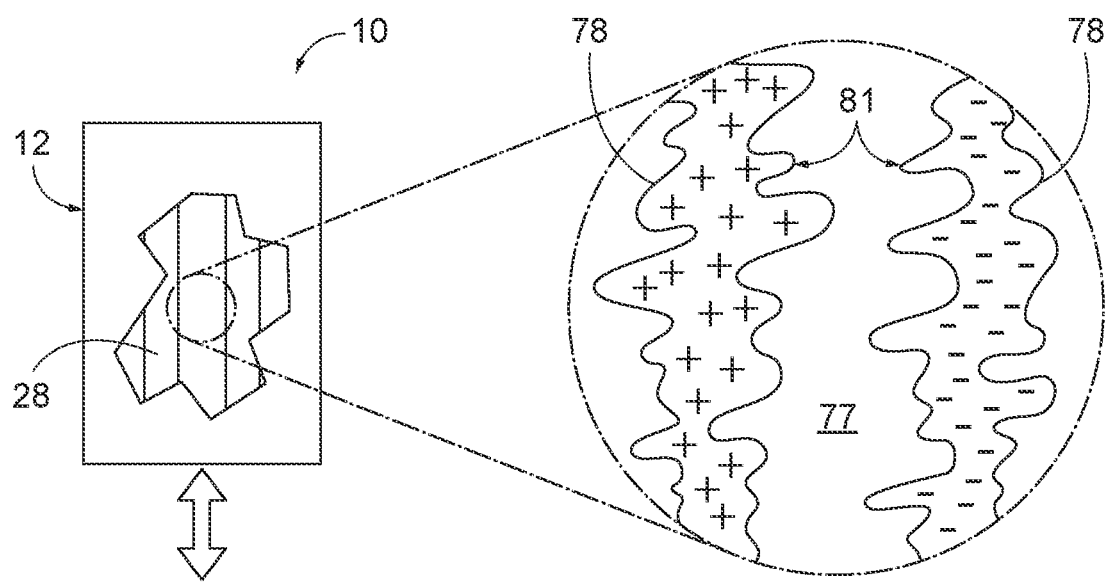
FIG. 11 is a schematic detailed view representing example body-worn air-treatment devices.

In some devices 10, the pathogen-deactivating mechanism 14 is configured to generate an electric field 77 through which air being inhaled or exhaled through a given nasal cavity 114 is forced to flow when the body 12 is operatively coupled proximate to the respiratory tract inlet 100 of the living individual 102, for example, with the electric field 77 being sufficient to deactivate the pathogens. In some such examples, the pathogen-deactivating mechanism 14 comprises electrodes 81 operatively coupled to a power source 82 (such as a battery or batteries 84) and configured to generate an electric field 77 between the electrodes 81 and within the void 28 defined by the body 12. In some examples, the pathogen-deactivating mechanism 14 comprises an electroceutical fabric 78 that defines the electrodes 81. For example, in some such examples, the body 12 at least partially defines the void 28 through which air is permitted, and optionally forced, to flow when the body 12 is operatively coupled proximate to the respiratory tract inlet 100 of a living individual 102, and the electroceutical fabric 78 at least partially spans the void 28 to create the electric field 77, through which air flows when the living individual 102 breathes. In some such examples, the electroceutical fabric 78 comprises a plurality of plies 80 that spans the void 28. FIGS. 10 and 11 schematically illustrate examples of devices 10 with electroceutical fabric 78. In example device 10 of FIG. 10, the electroceutical fabric 78 spans the void 28 across the longitudinal axis of the void (i.e., transverse thereto), with the electroceutical fabric 78 not only creating an electric field or fields 77 but also filtering the air. In example device 10 of FIG. 11, the electroceutical fabric 78 spans the void 28 in a direction aligned with the longitudinal axis of the void 28 (i.e., in a direction of air flow), thereby not hindering the flow of air, or at least hindering the flow of air less than in examples where the electroceutical fabric 78 spans transverse to the longitudinal axis of the void 28. In some examples, an optional covering 70 comprises electroceutical fabric 78 that generates an electric field 77.

In some examples of devices 10, the body 12 is configured to support a power source 82 (e.g., one or more batteries 84) to power the pathogen-deactivating mechanism 14. In some such examples, device 10 further comprises the power source 82. That is, some devices 10 may come with a power source installed, while other devices 10 may come without a power source 82 installed and thus require a power source to be operatively connected to the device 10 before the device 10 may be utilized to deactivate pathogens. Some devices 10 may comprise an integral power source 82 that is not configured to be replaced. Some such devices 10 may be constructed as a single use device, with such devices 10 not being designed or intended to have power source 82 replaced or recharged when depleted. In some examples, an integral and/or preinstalled power source 82 may be restricted from operatively providing power by a temporary tab, or other structure, that is configured to be removed by an end user, such that when an end user pulls the tab, the power source 82 provides power to the pathogen-deactivating mechanism 14.

Devices 10 that are constructed as a single use device may be inexpensive to produce and may be well suited for distribution at large public gatherings or events, such as concerts, sporting events, political and other rallies, conventions, etc. For example, such devices 10 may be distributed to attendees as they arrive at an event and attendees may be required, or encouraged, to use the device 10 during the event.

Other devices 10, however, may comprise a power source 82 that is rechargeable, such as one or more rechargeable batteries 84, with such devices 10 therefore being designed or intended to be used multiple times. Such a power source 82 may be referred to as a rechargeable power source. In some examples, the power source 82 (i.e., one or more rechargeable batteries 84) is configured to be recharged via a contactless recharger. Such examples may be able to have a smaller overall volume without the need for a recharging port or an access panel for end users to be able to remove and replace batteries 84. In other examples, however, devices 10 may include a charging port 66 that is supported by the body 12 and that is configured to be selectively coupled to an external power source for charging the power source 82.

Some devices 10 comprise a controller 85 that is supported by the body 12. When present, the controller 85 may be configured, constructed, and/or programmed to control various functions of a device 10. For example, the controller 85 may be configured to regulate a voltage applied by and/or a current supplied by a power source 82 to the pathogen-deactivating mechanism 14. In some examples, the controller 85 is configured to track a number of cycles that the pathogen-deactivating mechanism 14 has been activated. Additionally or alternatively, in some examples, the controller 85 may be configured to track a length of time that the pathogen-deactivating mechanism 14 has been selectively activated. In some examples, the controller 85 is configured to restrict activation of the pathogen-deactivating mechanism 14 upon the pathogen-deactivating mechanism 14 having been activated for a predetermined length of time, upon the power source 82 falling below a predetermined power level, and/or based at least in part on criteria associated with efficacy of the pathogen-deactivating mechanism 14. In some examples, the controller 85 is configured to generate an alert upon the pathogen-deactivating mechanism 14 having been activated for a predetermined length of time, upon the power source 82 falling below a predetermined power level, and/or based at least in part on criteria associated with efficacy of the pathogen-deactivating mechanism 14. Additionally or alternatively, in some examples, the controller 85 is configured to determine a potential output of the power source 82 and to restrict activation of the pathogen-deactivating mechanism 14 when the power source 82 does not have sufficient potential output to activate the at least one pathogen-deactivating mechanism 14 for a predetermined period of time.

Accordingly, the controller 85 may be configured to deactivate a device 10, or otherwise restrict activation of the pathogen-deactivating mechanism 14 thereof, or may alert a user when the device or the pathogen-deactivating mechanism 14 thereof is incapable of deactivating pathogens at a desired or requisite level, so that a user does not use the device 10 or attempt to use the device 10 when the device 10 will be ineffective for its pathogen-deactivating purpose. A user therefore may refrain, or be restricted, from further use of the device 10 until the power source 82 is recharged and/or the pathogen-deactivating mechanism 14, or component thereof (e.g., a light source 54), is replaced.

A controller 85 may be any suitable device or devices that are configured to perform the functions of the controller 85 discussed herein. For example, the controller 85 may include one or more of an electronic controller, a dedicated controller, a special-purpose controller, a microprocessor, a circuit board, a logic device, a memory device, and/or a memory device having computer-readable media 92 suitable for storing computer-executable instructions for implementing aspects of devices 10 and and/or methods according to the present disclosure. Additionally or alternatively, a controller 85 may include, or be configured to read, non-transitory computer-readable storage, or memory, media 92 suitable for storing computer-executable instructions, or software, for implementing methods or steps of methods according to the present disclosure. Examples of such media 92 include flash memory and ROM. As used herein, storage, or memory, devices and media 92 having computer-executable instructions as well as computer-implemented methods and other methods according to the present disclosure are considered to be within the scope of subject matter deemed patentable in accordance with Section 101 of Title 35 of the United States Code.

Some examples of devices 10 comprise a user control 86 that is supported by the body 12 and that is operatively coupled to, or in communication with, the controller 85. When present, the user control 86 may be configured to permit a user to activate the pathogen-deactivating mechanism 14, deactivate pathogen-deactivating mechanism 14, program the controller 85, and/or set an activation period of time for the pathogen-deactivating mechanism 14. Examples of user controls 86 include on/off switches, dials, buttons, touch screens, etc.

Some devices 10 comprise an indicator 94 that is supported by the body 12 and that is configured to indicate a current status of the device 10, such as a battery level, an on/off status, etc. The indicator 94, when present, may take any suitable form, including, for example, a visible indicator, such as a visible light LED, and/or an audible indicator, such as a piezoelectric buzzer, beeper, or speaker. In example devices 10 that are nose-mounted, as discussed herein, an indicator 94 may take the form of a visible light LED that is positioned to emit light that will be visible outside of the nose 104 when the device 10 is donned and when the pathogen-deactivating mechanism 14 is operatively functioning. Accordingly, third parties will be able to readily see that the living individual 102 donning the device 10 has an active device 10 in place. In such an example, the visible light LED may be sized and/or selected to provide such a visible indicator without overly illuminating the living individual's face, impairing the living individual's vision, etc.

Some devices 10 comprise a display 96 that is supported by the body 12 and that is configured to display information associated with the device 10, such as battery level, on/off status, a timer, a programming interface, etc. Displays 96 may take any suitable form including, for example, electroluminescent displays, liquid crystal displays, and LED displays.

Some examples of devices 10 comprise a wireless transceiver 88 and/or a wired connection port 90 supported by the body 12 and coupled to the controller 85. When so included, the controller 85 is configured to send, such as via the wireless transceiver 88 and/or the wired connection port 90, signals representative of one or more of a status of the power source 82, a status of the at least one pathogen-deactivating mechanism 14, the voltage across the power source 82, the current able to be supplied by the power source 82, the number of cycles that the pathogen-deactivating mechanism 14 has been activated, the length of time that the pathogen-deactivating mechanism 14 has been activated, and/or a subsequent length of time the power source 82 is able to operatively power the at least one pathogen-deactivating mechanism 14. Accordingly, devices 10 may be configured to be operatively coupled to an external computing device, such as a personal computer, a laptop computer, a mobile computing device, a smart phone, a smart watch, a tablet computer, etc. to facilitate a user determining a status of the device. Similarly, in some examples, the controller 85 is configured to receive, such as via the wireless transceiver 88 and/or the wired connection port 90, signals representative of instructions to activate the power source(s) 82, deactivate the power source(s) 82, program the controller 85, and/or set an activation period of time for the pathogen-deactivating mechanism 14. Accordingly, devices 10 may be configured to be operated and/or programmed via an external computing device. In some examples, the external computing device may replicate, substitute for, or function as, the indicator 94 and/or the display 96 of the device. In some examples, a device 10 may be used in combination with software stored on an external computing device, with the software comprising computer-executable instructions configured to cause a computing device to communicate with the controller 85 via the wireless transceiver 88 and/or the wired connection port 90. As an example, devices 10 may have a companion mobile application that interfaces with the device 10.

Some bodies 12 of devices 10 are configured to be selectively coupled to the nose 104, while other bodies 12 of devices 10 are configured to be coupled within the mouth 106 of a living individual 102, such as to a tooth or teeth 120. Some bodies 12 of devices 10 are configured to be selectively coupled to a head 116 of a living individual 102, such as with the body 12 being, forming a portion of, or being coupled or anchored to headwear or eyewear. Examples of headwear include a hat, a visor, a cap, and a headband. Examples of eyewear include eyeglasses and an eyewear frame.

The body 12 of devices 10 may be constructed, or composed, of any suitable material or combination of materials. In some examples, the body 12 is composed of, is at least partially composed of, or comprises one or more of an antimicrobial material 52, a resilient material 16, and/or a material that is compatible with (i.e., will not damage or cause irritation to) tissue of a living individual 102. Accordingly, in some examples, not only does pathogen-deactivating mechanism 14 deactivate pathogens passing through device 10, but also pathogens that come into contact with body 12 may be deactivated. That is, in some examples, the body 12 itself may deactivate pathogens in addition to the pathogen-deactivating mechanism 14 deactivating pathogens. An antimicrobial material 52 may be embedded in the body 12 of a device 10 and/or may be applied to the exterior of the body 12 of a device 10. Examples of antimicrobial materials 52 include those composed of or having copper, copper alloys, silver, quaternary ammonium compounds, chlorhexidine incorporated hydroxyapatite coatings, chlorhexidine-containing polylactide coatings, polymer and calcium phosphate coatings with chlorhexidine, antibiotic coatings, antiviral surfaces, and others. In some examples, a material or materials for body 12 may be selected to facilitate a desired flexibility and/or resilience for operative coupling of the body 12 to a living individual 102, as discussed herein.

As schematically represented in FIG. 3, in some examples of devices 10, the body 12 comprises a first body part 18 that is composed or otherwise formed of a first resilient material 22, and a second body part 20 that is at least partially embedded within the first body part 18 and composed or otherwise formed of a second resilient material 24. In some such examples, the second resilient material 24 has a spring constant greater than the first resilient material, and thus the second body part 20 may be described as constituting or defining a spring, or a leaf spring.

In some examples, the body 12 is resiliently conformable amongst a range of conformations comprising at least a sprung conformation and a flexed conformation. Such a body 12 and/or a device 10 that includes such a body may be referred to as a resiliently conformable body 12 and/or a resiliently conformable device 10, respectively. In some such embodiments, the body 12 may be biased toward the sprung conformation, such as by one or more springs or resilient portions of the device 10 and/or the body 12 portion thereof. The sprung conformation may additionally or alternatively be described as a default conformation, a nominal conformation, and/or a resting conformation, in that the internal bias, or springiness, of the body 12 causes it to revert to, or at least toward, the sprung conformation when no external force is applied on the body 12 against the internal bias thereof. The flexed conformation additionally or alternatively may be described as an energized conformation, a stressed conformation, and/or a deflected conformation, in that the spring of the body 12 is energized upon a user applying an external force against the bias of the body 12. In some examples, the flexed conformation may be a compressed conformation, while in other examples, the flexed conformation may be a tensioned conformation, for example, depending on how the body 12 is configured to be operatively coupled to a living individual 102. The various conformations described and/or illustrated herein additionally or alternatively may be referred to as configurations, states, and/or positions without departing from the scope of the present disclosure.

In some examples of devices 10 having a resiliently conformable body 12, the pathogen-deactivating mechanism 14 is configured to be automatically activated when the body 12 is within a predetermined subset of conformations of the range of conformations. For example, rather than, or in addition to, having a user-activated and/or externally accessible on/off button or switch that is engaged and operated by a user, a device 10 may be configured to automatically activate pathogen-deactivating mechanism 14 when the body 12 has been manipulated by a user into a certain conformation or subset of conformations of the range of conformations. For example, with reference to example devices 310, 302, and 304 of FIGS. 15-20, discussed in greater detail below, when the body 12 of example devices 310, 302, and 304 is compressed from the sprung conformation (FIGS. 15, 17, and 19) to or toward the flexed conformation (FIGS. 16, 18, and 20), such as when the device is inserted into a nostril 112 of a living individual 102, the pathogen-deactivating mechanism 14 automatically will be activated, such as via an internal switch 53 within the body 12 of the device. Similarly, with reference to example devices 306, 308, 312, and 314 of FIGS. 30-37, also discussed in greater detail below, when the body 12 of example devices 306, 308, 312, and 314 is tensioned, or expanded, from the sprung conformation (FIGS. 30, 32, 34, and 36) to or toward the flexed conformation (FIGS. 31, 33, 35, and 37), such as when the example devices 306, 308, and 314 are clipped to a septal region 108 of a living individual 102 or when the example device 312 is clipped to a wing 110 of a nose 104 of a living individual 102, the pathogen-deactivating mechanism(s) 14 automatically will be activated, such as via an internal switch 53 within the body 12 of the device 10. In some examples, the pathogen-deactivating mechanism 14 may be configured to be automatically activated when the body 12 is not in the sprung conformation. In other examples, the pathogen-deactivating mechanism 14 may be configured to be automatically deactivated when the body 12 is not in the flexed conformation. Such an optional configuration of a device 10 facilitates conservation of the device's power source 82, in that the device will only activate the pathogen-deactivating mechanism 14 when the body 12 is in a conformation corresponding to being coupled to a living individual 102.

Figure 8:
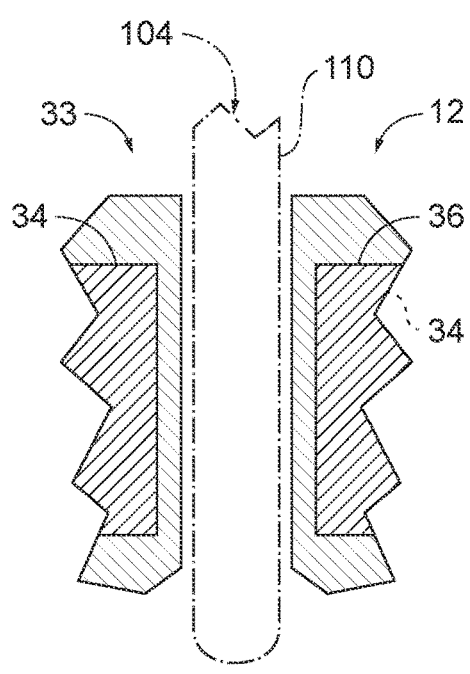
FIG. 8 is a schematic fragmentary cross-sectional view representing example bodies of body-worn air-treatment devices.
Figure 9:
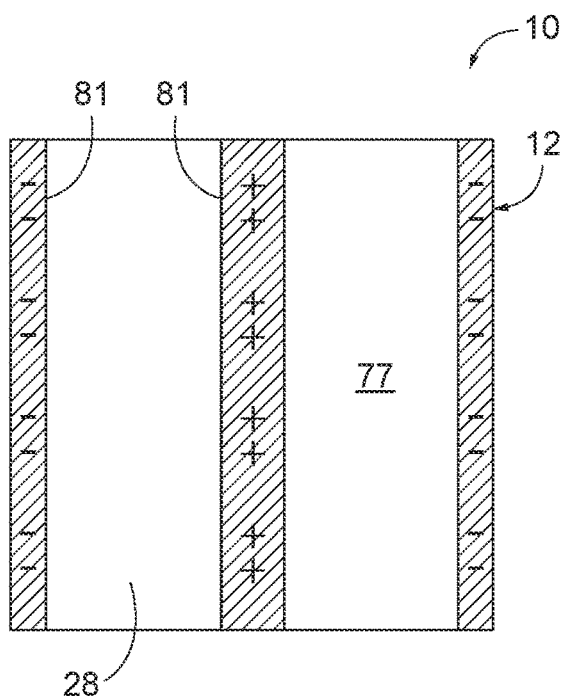
FIG. 9 is a schematic cross-sectional view representing example body-worn air-treatment devices.

In some examples, devices 10 may utilize a mechanism other than, or in addition to, a mechanical mechanism to couple at least the pathogen-deactivating mechanism 14 of the body 12 proximate to the respiratory tract inlet 100 of the living individual 102. As an example, device 10 may utilize an adhesive 40 or a magnetic assembly 33 to couple, or operatively position, at least a portion of the device 10, such as the body 12 and/or the pathogen-deactivating mechanism 14 thereof, proximate to the respiratory tract inlet of the living individual. As schematically represented in FIG. 8, the magnetic assembly 33 may include at least one magnet 34 configured to couple, and in some examples may include at least a pair of magnets 34 that are configured to be magnetically coupled, or retained, together to couple, at least the pathogen-deactivating mechanism 14 of the body 12 and/or the device 10 proximate to the respiratory tract inlet 100 of the living individual 102. In some examples, the magnetic assembly 33 includes at least one magnet 34 and a ferromagnetic element 36 that is configured to be selectively positioned within a magnetic field of the at least one magnet 34 to couple at least the pathogen-deactivating mechanism 14 of the body 12 and/or the device 10 proximate to the respiratory tract inlet 100 of the living individual 102. Ferromagnetic element 36 may be a magnetic material that is not permanently magnetized, such as an iron-containing material, although it is within the scope of the present disclosure that ferromagnetic element 36 also may be another magnet. The magnet(s) 34 and/or ferromagnetic element 36 of the magnetic assembly 33 are sized, selected, and/or configured to form a mating pair that creates a sufficient magnetic force, or magnetic attraction, therebetween to operatively couple the device 10, or corresponding portion thereof, proximate to the respiratory tract inlet 100 of the living individual 102. Examples of suitable magnets 34 include discrete magnets, bar magnets, sheet magnets, correlated magnets (an ordered group of magnetic dipoles), or any suitable magnet configuration or assembly.

In some examples, the magnet(s) 34 and/or ferromagnetic element 36 may be magnetically coupled together on opposed sides of a portion of the living individual's nose 104, such as a wing 110 or septum thereof, to couple at least the pathogen-deactivating mechanism 14 of the body 12 and/or the device 10 proximate to the respiratory tract inlet 100 of the living individual 102. In some examples, the device 10, or at least one pathogen-deactivating mechanism 14 thereof, is configured to be automatically activated when the ferromagnetic element 36 is within a threshold distance from the magnet 34.

In some examples, each of a pair of devices 10 may comprise a magnet 34 and/or a ferromagnetic element 36, with each of the pair being configured for insertion into a single nostril 112, such that when operably positioned therein, the magnetic field of the magnet(s) 34 will encompass the septal region 108 of the living individual 102 and thereby attract the two devices together and against the living individual's septum.

As another example, device 10 may utilize an adhesive 40 to couple, or operatively position, at least a portion of the device 10, such as the body 12 and/or the pathogen-deactivating mechanism 14 thereof, proximate to the respiratory tract inlet of the living individual. The portion of device 10 that is adhesively coupled by the adhesive 40 may be referred to as an adhesive surface 38 of the device 10. The adhesive surface 38 thus may be sized, shaped, and/or otherwise configured to be selectively affixed by the adhesive 40 proximate to the respiratory tract inlet 100 of the living individual 102. The adhesive surface 38 may be configured to receive an adhesive 40, such as which is applied thereto by the living individual 102. Alternatively, the adhesive surface 38 may include the adhesive 40 when the device is manufactured. As an example, the adhesive surface 38 may include the adhesive and a backing 42 that is releasably coupled to the adhesive surface 38 and/or the adhesive 40 and configured to be removed therefrom when the device 10 is being affixed proximate to the respiratory tract inlet 100 of the living individual 102.

Figures 13, 14:
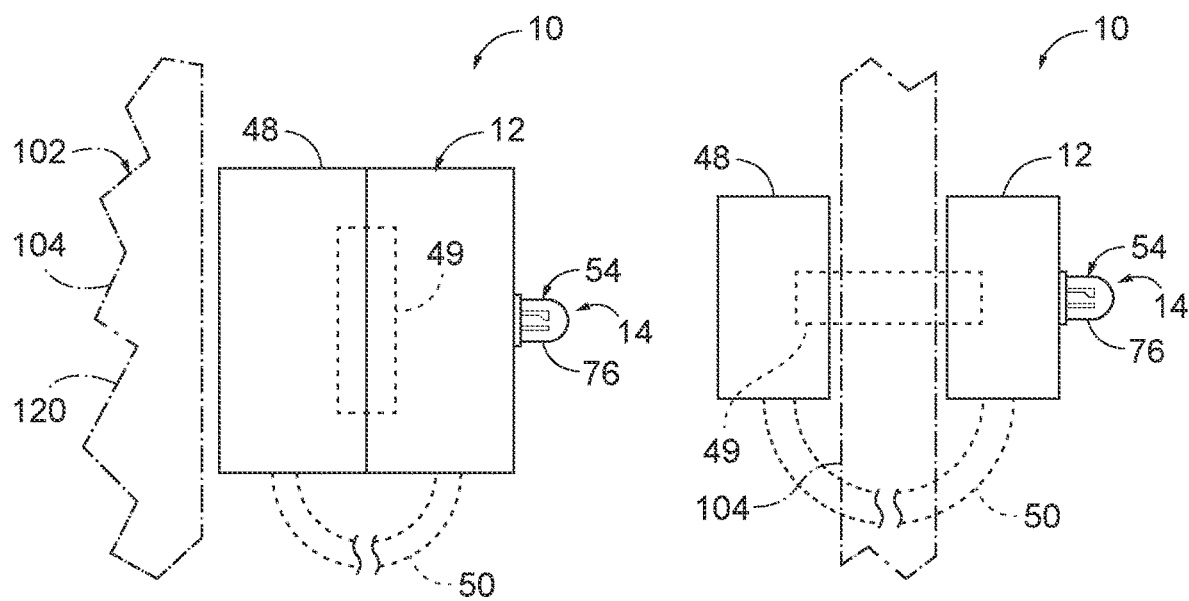
FIG. 13 is a schematic illustration representing example body-worn air-treatment devices.
FIG. 14 is a schematic illustration representing example body-worn air-treatment devices.

As schematically represented in FIGS. 13 and 14, some devices 10 further comprise an anchor 48 that is configured to be secured to the living individual's body, with the body 12 and the anchor 48 being configured to be selectively, and typically removably, coupled together to position the body 12, including pathogen-deactivating mechanism 14 thereof, proximate to the respiratory tract inlet 100 of the living individual 102. In some examples, the anchor 48 is clipped, mounted, inserted, implanted, or otherwise secured to a portion of the living individual's nose 104 or mouth 106. For example, an anchor 48 may be secured to a wing or septum of the living individual's nose or to at least one tooth or orthodontic appliance in the living individual's mouth.

When device 10 includes an anchor 48, the anchor may be configured to be permanently or semi-permanently secured to the portion of the living individual's body. For example, an anchor 48 may be or include a tooth band that is secured around a tooth, an anchor that is adhesively mounted to a tooth, and/or an orthodontic appliance that is adhesively or mechanically coupled to a tooth. As additional examples, an anchor 48 may be a nasal anchor, such as a nasal piercing that extends through a wing or septum of the living individual's nose or a nasal clip that is coupled to the wing or septum of the living individual's nose. In addition to coupling the device 10 to the portion of the living individual's body, the anchor 48, when present, may be utilized to position, support, or otherwise orient the device 10, such as the pathogen-deactivating mechanism 14 portion thereof, in a desired orientation for deactivating pathogens during operative use of the device 10.

When the living individual 102 desires to utilize the device 10 to deactivate pathogens, the body 12 of the device 10 may be selectively coupled to the anchor. When the living individual is not utilizing the device 10 to deactivate pathogens, the body 12 of the device 10 may be detached, or uncoupled, from the anchor. In some examples, the anchor 48 and/or the body 12 may be configured and/or constructed to permit repeated coupling and uncoupling of the body 12 and the anchor 48 without destruction or damage to either the anchor 48 or the body 12. When the device 10 includes an anchor 48, any suitable coupling mechanism 49 may be utilized to selectively couple the anchor to the body. Examples include adhesive coupling mechanisms, magnetic coupling mechanisms, and mechanical coupling mechanisms, such as are otherwise described herein.

As used herein, "semi-permanently," when used to describe a connection or coupling between elements, is intended to refer to elements that are not configured to be readily separated or uncoupled, but which may be separated or uncoupled without destruction of or damage to the elements. Thus, elements that are semi-permanently secured together may be damaged or may require precise movement, manipulation, or tools to separate or uncouple, whereas elements that are removably coupled together may be configured to be repeatedly coupled and uncoupled without destruction of or damage to the elements. Furthermore, and as used herein, "permanently," when used to describe a connection or coupling between elements, is intended to refer to elements that are not configured to be separated or uncoupled without destruction of or damage to one or both of the elements or the coupling mechanism utilized to permanently secure the elements together.

When device 10 includes an anchor 48, the device 10 optionally may include a tether 50 that physically interconnects the anchor 48 and the body 12 so that the body 12 is physically retained proximate the anchor even if the body 12 is uncoupled from the living individual's body. The tether 50, when present, thus may prevent loss of the body 12 of the device, such as if the body 12 is inadvertently uncoupled from the living individual's body. It follows that the tether 50 thus may be described as defining a maximum distance or range of movement of the body 12 relative to the anchor 48. Examples of a suitable tether include a wire, a chain, a string, or a lanyard. The tether 50, when present, may be formed from a flexible and/or elastomeric material that permits relative movement of the body 12 relative to the anchor 48 when the body 12 is uncoupled from the anchor 48.

As mentioned, some bodies 12 of devices 10 are configured to be selectively coupled to a nose 104 of a living individual 102. Such devices 10 may be described as nose-mounted devices 300, and FIGS. 15-41 provide examples thereof.

Some nose-mounted devices 300 are configured to pinch a portion of a nose 104, such as the septal region 108 or wing 110 thereof. Example devices 306, 308, 312, 314, and 350 illustrated in FIGS. 30-41 are examples of such devices 300. In such examples, the flexed conformation is a tensioned conformation, with the body 12 being configured to be selectively expanded toward the flexed conformation responsive to an external force on the body 12. For example, the body 12 may comprise two end regions 26 that are closer together when the body 12 is in the sprung conformation (e.g., FIGS. 30, 32, 34, and 36) than in the flexed conformation (e.g., FIGS. 31, 33, 35, and 37), and with the two end regions being configured to engage opposite sides of a portion of a nose 104 (e.g., opposed sides of the septum or opposed sides of a wing of the nose) of a living individual 102, thereby pinching the portion of the nose to operatively retain the device 300 thereon. In some examples, when the body 12 is in the sprung conformation, the two end regions 26 engage each other, and in some such examples, such positioning of the two end regions 26 is configured to cause the pathogen-deactivating mechanism 14 to be turned off, or deactivated.

Other nose-mounted devices 300 are configured to expand within a nostril 112 of a living individual 102. Example devices 302, 304, and 310 illustrated in FIGS. 15-20 are examples of such devices 300. In such examples, the flexed conformation is a compressed conformation, with the body 12 being configured to be selectively compressed toward the flexed conformation responsive to an external force on the body 12. For example, in some examples, the body 12 may be described as having an outermost, or external, dimension 30 that is greatest when the body 12 is in the sprung conformation and that is reduced when the body 12 is compressed to or toward the flexed conformation.

More specifically, in some examples, the body 12 is configured to be selectively compressed toward the flexed conformation (FIGS. 16, 18, and 20) for insertion into a nostril 112 and released to expand toward the sprung conformation (FIGS. 15, 17, and 19) to engage inside surfaces of the nostril 112 and be retained at least partially within the nostril 112. In some examples, the body 12 is sized to be positioned fully within a nostril 112. In some examples, a portion of the device 10, such as portion of the body, a portion of light source 54, and/or a portion of a tether 50, may extend partially out of the nostril 112. In such examples this portion may facilitate removal of the device 10 from the nostril 112 and/or proper insertion of the device 10 into the nostril 112 because this portion may be easier to grasp when the device 10 is inserted and positioned within the nostril 112 or removed from the nostril 112.

As discussed, in some examples of devices 10, including some nose-mounted devices 300, tooth-mounted devices 400, and head-mounted devices 500, the body 12 at least partially defines a void 28 that is defined at least in part by the body 12. In such examples, the body 12 may be described as having a longitudinal axis 32, such as generally corresponding to the direction of air flow through the void 28 when such a device 10 is operatively worn by a living individual 102. In some such examples, when the body 12 is composed at least in part of a resilient material 16, the body 12 may be configured to be selectively squeezed toward the longitudinal axis 32 to conform the body 12 toward the flexed conformation. Example devices 302, 304, and 310 (FIGS. 15-20) are examples of such nose-mounted devices 300. In such examples, a user squeezes the body 12 to conform it into a size and shape for operative insertion into a nostril 112, and upon releasing the body 12, the body will return toward the sprung conformation to operatively engage the inside surface of the nostril for retention therein. In some examples, such as in example devices 310 and 302 (FIGS. 15-18), the body 12 fully circumscribes the void 28. In other examples, such as in example device 304 (FIGS. 19 and 20), the body 12 only partially circumscribes the void 28.

As used herein, the void 28 additionally or alternatively may be described as an air passage 28, an air conduit 28, a flow passage 28, and/or a duct 28. In addition, the voids 28 that are described and/or illustrated herein may be at least partially, if not at least substantially or even completely, defined by the device 10, such as the body 12 thereof. In some examples, the void 28 may be surrounded by the body 12, with the void 28 having openings on opposed ends of the body 12. These openings thus may be inlets or outlets for air flowing through the void 28. In some examples, the void 28 extends into the body from end regions and a side wall of the body. In such examples, the void 28 may define openings on opposed end regions 72 of the body 12, as well as a lateral opening extending between the openings on the opposed end regions of the body. Such a lateral opening often will be at least partially closed during use of the device 10, such as when the body is configured to a flexed conformation and/or when a portion of the living individual's body, such as wing or septum of the individual's nose extends through the lateral opening. In some examples, the void 28 is cylindrical, substantially cylindrical, or generally cylindrical; however, any suitable shape of void 28 may be incorporated into a device 10.

Some examples of bodies 12 of devices 10 are configured to mate with, extend into, or otherwise nest or nestle with a specific portion or portions of a living individual 102 for operative retention of the device 10 on the living individual 102. That is, the body 12 of a device 10 may comprise one or more sub-portions 65 that is/are sized and/or shaped to mate with, extend into, or otherwise nest or nestle with a specific portion of a living individual 102 for operative retention of the device 10 on the living individual 102. For example, the sub-portion(s) 65 may be configured to engage a portion of the living individual 102 to restrict gravity causing the device 10 to fall away from, or out of, the living individual 102, such as a nostril 112 thereof. Additionally or alternatively, the sub-portion(s) 65 may be configured to engage a portion of the living individual 102 to cause an opposite region of the body 12 to wedge or be urged against another portion of the living individual 102.

In some such examples, the sub-portion 65 comprises or defines a projection 67, extending from an adjacent portion of the body 12. In some such examples, the projection 67 is narrowed relative to an adjacent portion of the body 12. As an illustrative, non-exclusive example, a sub-portion 65, which optionally may be a projection 67, of the body 12 of a nose-mounted device 300 may be configured, sized, and/or shaped to engage a nasal vestibule (i.e., the area just inside the nostril that leads into the nasal cavity) of a living individual 102 donning the device 10. In more specific examples, a sub-portion 65, which optionally may be a projection 67, may be configured, sized, and/or shaped to engage the superior region of a nasal vestibule and to thereby wedge or urge the remainder of the body 12 against an inside surface of the nostril 112. The example nose-mounted device 330 of FIGS. 21-29 is an example of a nose-mounted device 300 whose body 12 comprises a sub-portion 65 in the form of a projection 67 that is configured to engage a superior region of a nasal vestibule to urge the remainder of the body 12 against the inside surface of the nostril 112 to retain the device 10 within the nostril 112.

Figure 12:
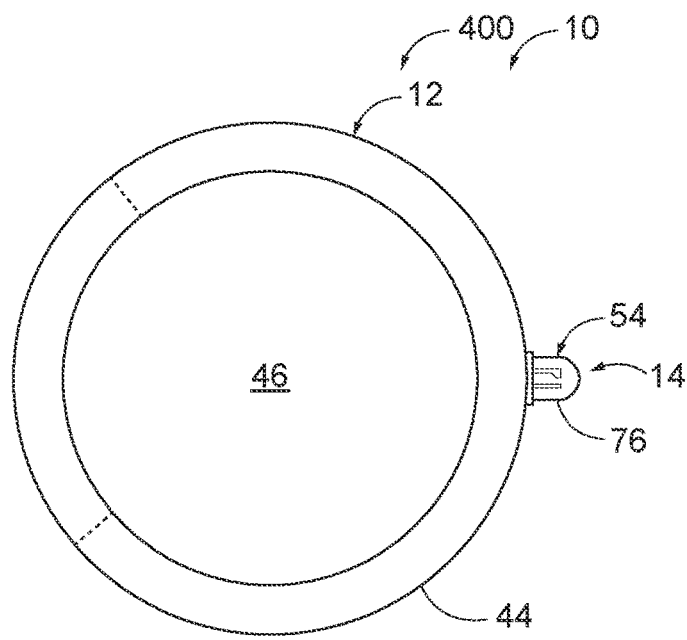
FIG. 12 is a schematic illustration representing example tooth-mounted body-worn air-treatment devices.

With reference to FIG. 12 and as mentioned, some bodies 12 of devices 10 in the form of tooth-mounted air-treatment devices 400 according to the present disclosure are configured to be coupled to a tooth 120 of the living individual 102 and thereby be operatively positioned to deactivate at least pathogens entering or being exhausted from the living individual's respiratory tract via the living individual's mouth 106. Tooth-mounted air-treatment devices 400 may be secured to any suitable surface of the living individual's tooth, or teeth. As examples, and especially when device 400 includes a pathogen-deactivating mechanism 14 that includes at least one LED 76 or other light source 54, the light source may be positioned to emit light into the living individual's oral cavity without being significantly obstructed by the living individual's tongue. As examples, the device may be secured to a palatal surface of the living individual's tooth so that the light source 54 emits light primarily in the palatal direction and/or toward the living individual's throat, as opposed to primarily emitting light in a buccal or labial direction. Also, while a tooth-mounted air-treatment device 400 may be coupled to any surface of any of the living individual's teeth, a buccal surface of one or more teeth of the living individual's maxilla (upper jaw) may be less likely to be obstructed than a corresponding surface of a tooth of the living individual's mandible (lower jaw).

The body 12 of such a device 400 may be coupled to the tooth directly, such as with an adhesive 40, or the body 12 may be coupled to an anchor 48 that is secured to the tooth. The anchor 48, when present, may be configured and/or installed to position the pathogen-deactivating mechanism 14, such as the one or more light sources 54 thereof, to deactivate pathogens flowing through the living individual's mouth while the individual breathes, talks, etc. For example, the device 400, or anchor 48 thereof, may be or include a band 44 that is sized and configured to extend at least partially, and optionally fully, around the tooth 120 of the living individual. As another example, the body 12 of the device 10 and/or the anchor 48 may include or define a cavity 46 that is sized to receive at least a portion of the tooth 120 to couple the body 12 to the tooth 120.

Figure 42:
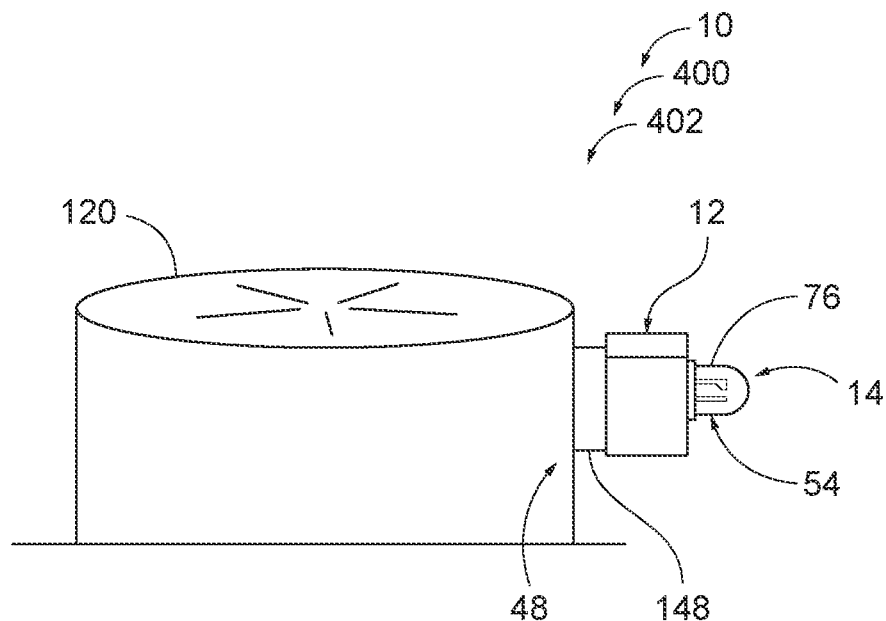
FIG. 42 is a schematic illustration representing example tooth-mounted body-worn air-treatment devices.

An example of a device 10 in the form of a tooth-mounted air-treatment device 400 that is coupled to an anchor 48 that is secured to the tooth 120 is shown in FIG. 42 and generally indicated at 402. Anchor 48 may have any suitable shape or construction and may be secured to the tooth 120 via any suitable mechanism, such as with an adhesive or a mechanical fastener, such as a screw, or clip. Anchor 48 in turn may be configured to be permanently or semi-permanently coupled to device 402. More specific examples of permanently coupled anchors 48 include anchors that are integrally formed with device 402, welded to device 402 and/or bonded to device 402. In contract, examples of semi-permanently coupled anchors 48 include anchors that are threadingly coupled to device 402, magnetically coupled to device 402, and/or coupled to device 402 with a friction fit, clip, or other releasable mechanical fastening mechanism.

Figure 43:
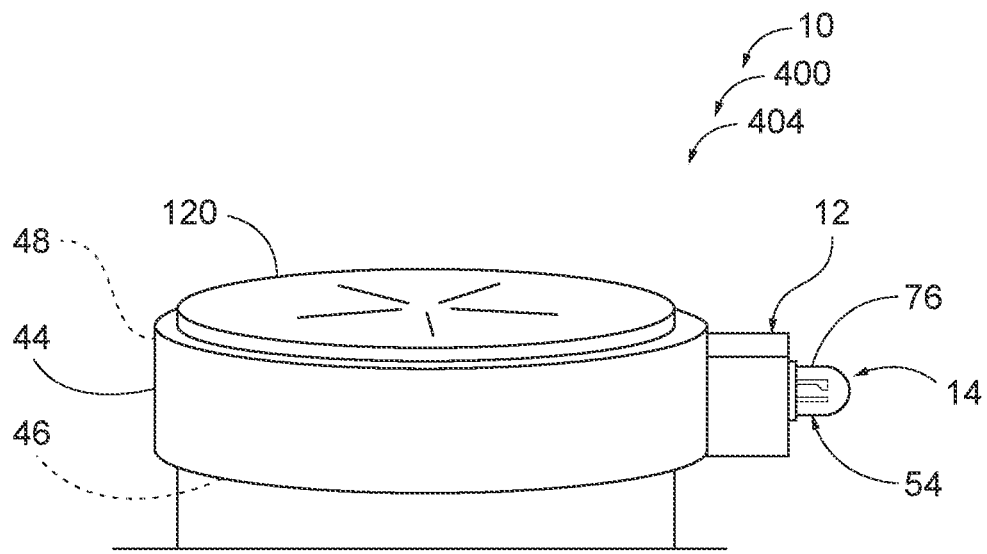
FIG. 43 is a schematic illustration representing example tooth-mounted body-worn air-treatment devices.
Figure 44:
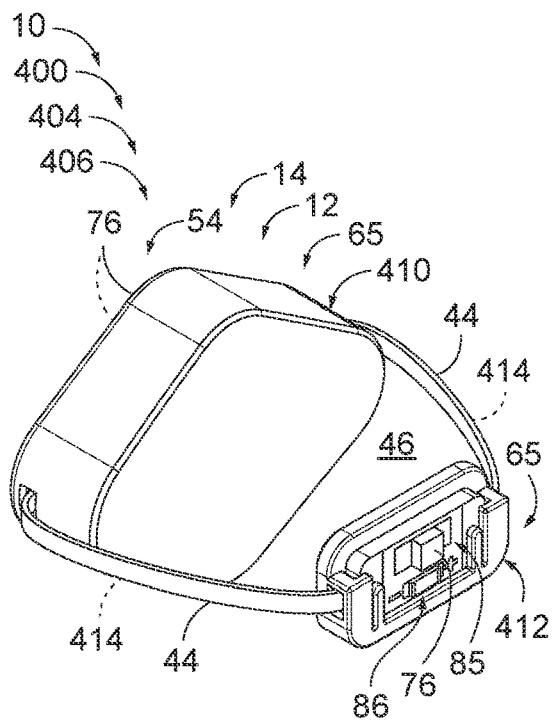
FIG. 44 is an isometric view of an example tooth-mounted body-worn air-treatment device.

An example of a device 10 in the form of a tooth-mounted air-treatment device 400 with an anchor 48 in the form of a band 44 is shown in FIG. 43 and generally indicated at 404. The band 44 may be permanently or semi-permanently coupled to the device, such as in the manners described above with respect to the anchor 48.

A potential benefit of permanently coupled devices 404 is that they are not likely to be dislodged or repositioned after being secured to the individual's tooth. A potential benefit of selectively coupled devices 404 is that the device may be selectively removed from the tooth (and the individual's mouth), such as during periods in which the device is not being used, or when the device needs to be recharged, have its battery replaced, or undergo maintenance. When device 404 is permanently coupled to the band 44 and/or the anchor 48, the device and the corresponding band and/or anchor may be installed and oriented on the tooth by an orthodontist, dentist, or other suitably trained practitioner. When device 404 is selectively coupled to the band and/or the anchor, the band and/or the anchor may be installed and oriented on the tooth by an orthodontist, dentist, or other suitably trained practitioner, and the living individual may selectively couple the device 404 during periods in which the device is to be used.

FIGS. 44-47 provide additional examples of tooth-mounted air-treatment devices 404 according to the present disclosure and are indicated generally at 406. As discussed, it is within the scope of the present disclosure that the features, configurations, components, properties, etc. of the examples of devices 406 of FIGS. 44-47 may be utilized with other devices 400 and 10 according to the present disclosure, and that the example devices 406 of FIGS. 44-47 may include any of the features, configurations, components, properties, etc. of the other devices 400 and/or 10 disclosed herein.

Figure 45:
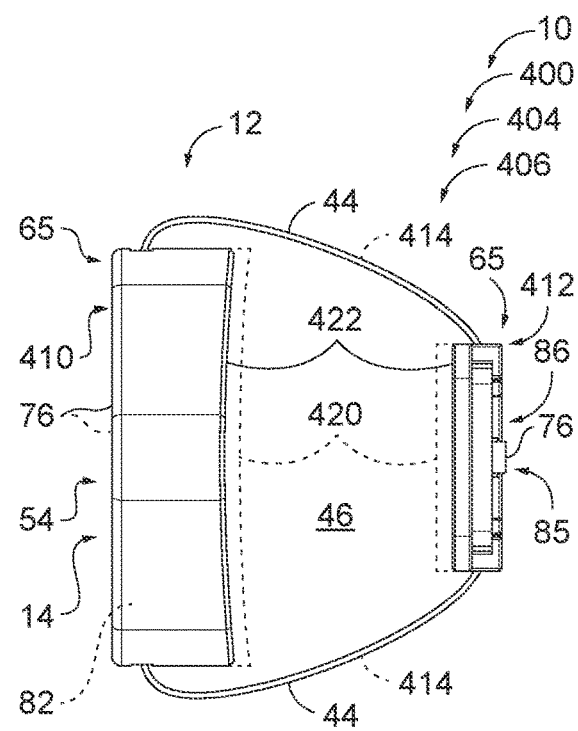
FIG. 45 is a top plan view of the example tooth-mounted body-worn air-treatment device of FIG. 44.
Figure 46:
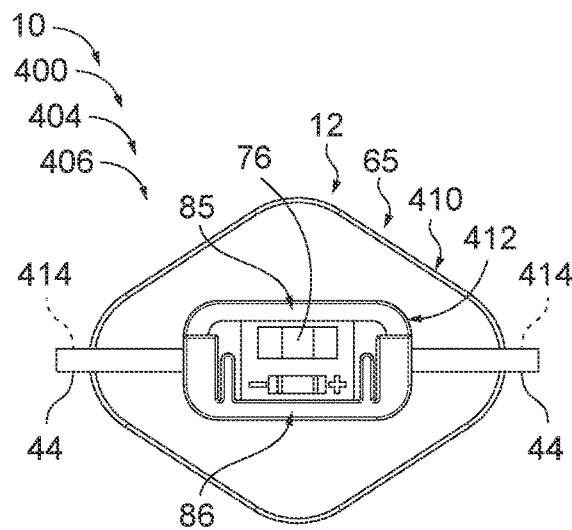
FIG. 46 is a side view of the example tooth-mounted body-worn air-treatment device of FIG. 44.
Figure 47:
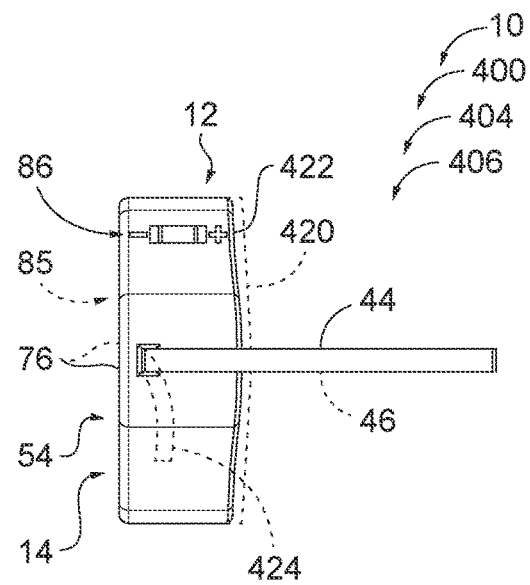
FIG. 47 is a side view of a variant of the example tooth-mounted body-worn air-treatment device of FIG. 44.

In FIGS. 44-47, tooth-mounted air-treatment device 406 takes the form of a tooth-mounted air-treatment device 404 that includes a band 44 that is configured to extend around a tooth of a living individual. In other words, the device 406 defines a cavity 46 through which a tooth of a living individual extends. As schematically indicated in FIGS. 45 and 47, devices 406 optionally may include a conformance layer 420 on at least one tooth-facing surface 422 of the device's body 12, including sub-portions 65 thereof. Conformance layer 420 may include and/or be formed from a resiliently compressible material that assists device 406 to conform and be securely coupled to the living individual's tooth. Examples of such a material include silicone and a closed-cell foam, although others may be used and are within the scope of the present disclosure.

As illustrated in FIGS. 44-47, device 406 includes a body 12 having a pair of sub-portions 65 that are secured on generally opposed surfaces of the living individual's tooth by band 44, which may be a flexible and/or adjustable band. The illustrated sub-portions 65 include a deactivating sub-portion 410 that contains the pathogen-deactivating mechanism 14, including at least one LED 76 or other light source 54. The illustrated sub-portions 65 also include a control sub-portion 412 that contains the device's controller 85 and user control 86, with the illustrated example of the user-control being an on/off switch. In such an example, the battery 84 or other power source 82 of the device may be contained in either sub-portion 65, with the example of FIGS. 44-46 indicating the power source being contained in deactivating sub-portion 410. Power and control signals may be transmitted between the sub-portions 65 by any suitable type and numbers of wires or other electrical conduits 414 that extend through the band. The wires or other electrical conduits 414 thus may be described as establishing electrical communication between the first and second sub-portions 65 of the body 12 and/or of the electrical components of the device 406 contained therein.

FIG. 47 demonstrates that all devices 400, 404, and/or 406 are not required to include a body 12 with a pair of sub-portions 65, with FIG. 47 illustrating a device 406 in which the pathogen-deactivating mechanism 14, controller 85, and user control 86 are all present in a single body portion. The example of FIG. 47 also schematically illustrates that it is within the scope of the present disclosure that the band 44 of a device 10, including devices 400, 404, and/or 406, may be selectively adjustable, such as to permit the length of the band to be lengthened, shortened, or otherwise adjusted during coupling of the device to the tooth or other portion of the living individual's body. In FIG. 47, band 44 is shown optionally including a free end 424 that may be selectively urged away from body 12 to shorten the length of the band 44 and thus reduce the size of the cavity 46 defined thereby.

As mentioned, some bodies 12 of devices 10 are configured to be selectively coupled to the head 116 of a living individual 102. Such devices 10 may be referred to herein as head-mounted devices 500. In such examples, the body 12 may comprise a head mount 98 that is configured to be selectively and operatively coupled to a user's head 116, and a support 99 that extends from the head mount 98, with the pathogen-deactivating mechanism 14 at least partially supported by the support 99. In some such examples, the pathogen-deactivating mechanism 14 comprises at least one light source 54, such as an LED 76, supported by the support 99 and configured to emit light within a germicidal spectrum. As examples, and as discussed in more detail herein, examples of head mount 98 include headwear, such as a hat, cap, visor, or headband, or eyewear, such as eyeglasses, or at least an eyewear frame.

Figure 15:
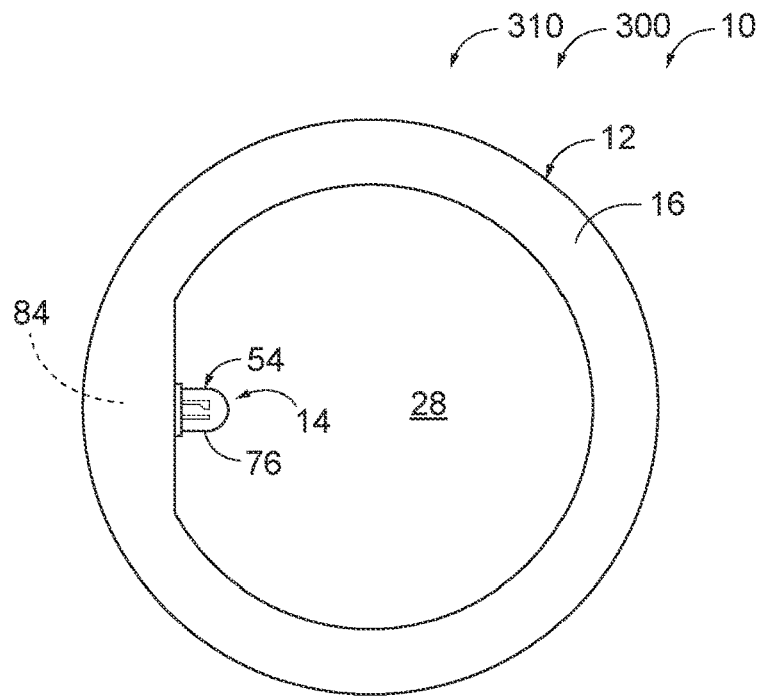
FIG. 15 is a schematic illustration representing example nose-mounted air-treatment devices, shown in a sprung conformation.
Figure 16:
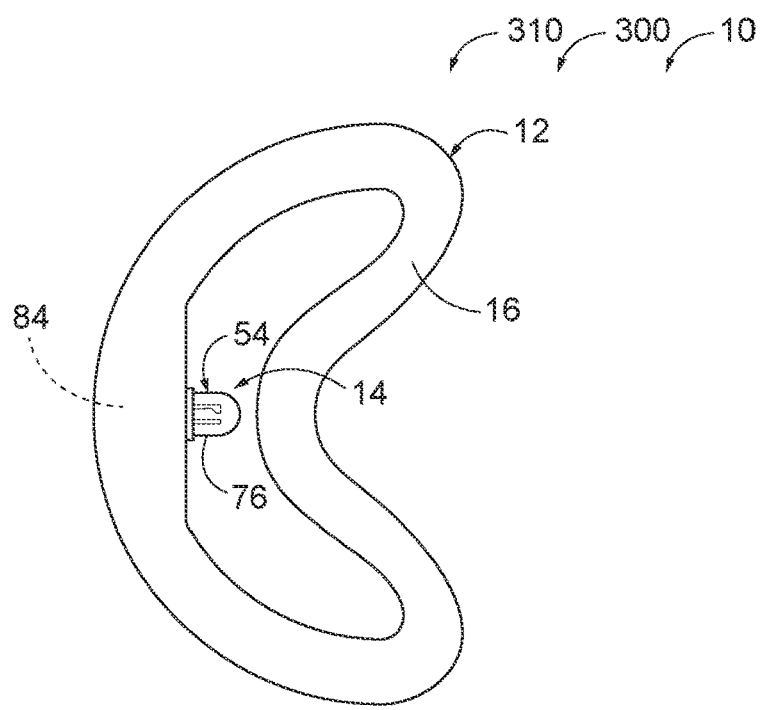
FIG. 16 is a schematic illustration representing the example nose-mounted air-treatment devices of FIG. 15, shown conformed to or toward a flexed conformation.

Turning now to FIGS. 15 and 16, example device 310 is an example of a nose-mounted device 300 that is configured to be inserted into and retained within a nostril 112 of the living individual 102. The body 12 of device 310 comprises a resilient material 16 and is configured to be compressed from a sprung conformation (FIG. 15) to or toward a flexed conformation (FIG. 16) for operative insertion into a nostril 112. Body 12 may be constructed with first and second body parts 18 and 20, such as according to the cross-sectional representation of FIG. 3, with the second body part 20 defining a spring. Once operatively positioned within a nostril 112, release of the compressive force on the body 12 causes the body 12 to spring back toward the sprung conformation (FIG. 15), so that the body 12 engages the inside surface of the nostril 112 in a friction-fit arrangement to be retained within the nostril 112. Body 12 of device 310 defines and fully circumscribes a void 28. The body 12 supports a pathogen-deactivating mechanism 14 that comprises an LED 76 that, when activated, emits light within the void 28 to deactivate pathogens as air passes through the void 28 as a result of a user breathing.

Figures 17, 18:
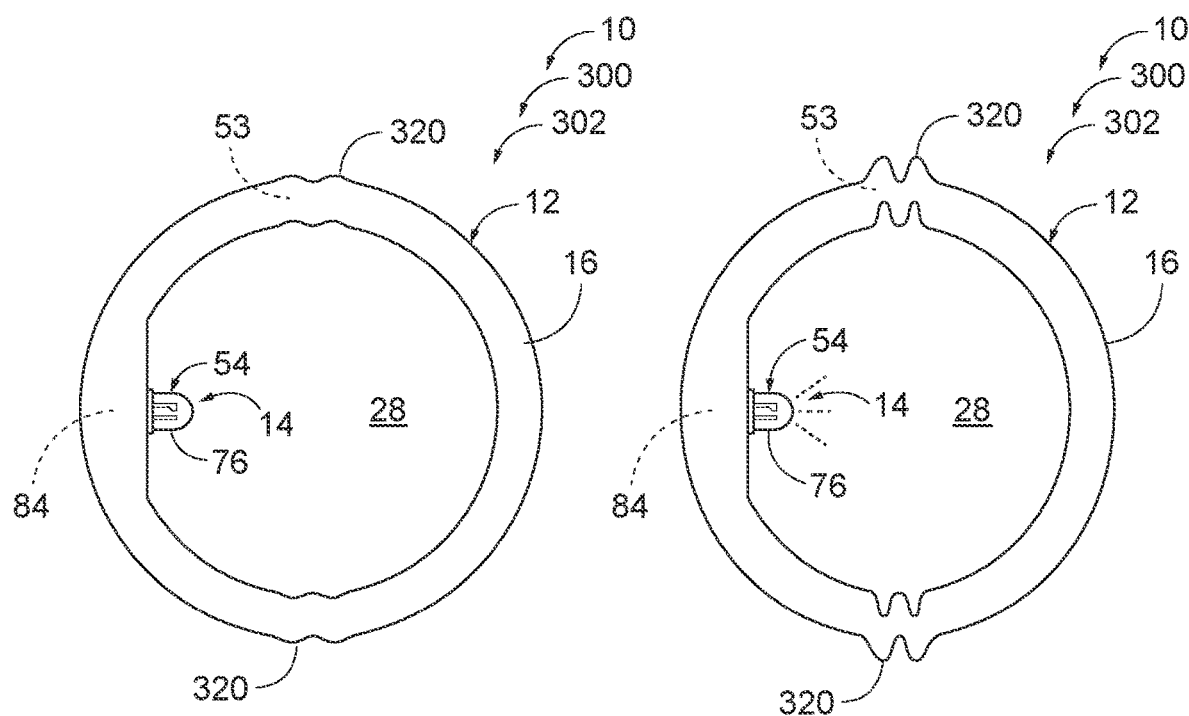
FIG. 17 is a schematic illustration representing example nose-mounted air-treatment devices, shown in a sprung conformation.
FIG. 18 is a schematic illustration representing the example nose-mounted air-treatment devices of FIG. 17, shown conformed to or toward a flexed conformation.

Example device 302 is illustrated in FIGS. 17 and 18. Similar to device 310, device 302 is an example of a nose-mounted device 300 that is configured to be inserted into and retained within a nostril 112. The body 12 of device 302 comprises a resilient material 16 and is configured to be compressed from a sprung conformation (FIG. 17) to or toward a flexed conformation (FIG. 18) for operative insertion into a nostril 112. As illustrated, the body 12 of device 302 may comprise or define one or more spring regions 320 that are configured to be compressed upon a user engaging and compressing opposing sides of the body toward each other. These spring region(s) 320 may be defined by a corrugated span of resilient material 16, for example, and/or an internal spring, such as a second body part 20 (FIG. 3) may be provided within the spring region(s) 320 to bias the body toward the sprung conformation (FIG. 17). Once operatively positioned within a nostril 112, release of the compressive force on the body 12 causes the body 12 to spring back toward the sprung conformation (FIG. 17) so that the body 12 engages the inside surface of the nostril 112 in a friction-fit arrangement to be retained within the nostril 112. Body 12 of device 302 defines and fully circumscribes a void 28. The body 12 supports a pathogen-deactivating mechanism 14 that comprises an LED 76 that, when activated, emits light within the void 28 to deactivate pathogens as air passes through the void 28 as a result of a user breathing. Device 302 may comprise an internal switch 53 configured to automatically activate the pathogen-deactivating mechanism 14 upon the body 12 being compressed away from the sprung conformation. Accordingly, when a user compresses the body 12 for insertion into a nostril 112, the pathogen-deactivating mechanism 14 will be activated, and when the body 12 is retained away from the sprung conformation as a result of engagement with the inside of the nostril 112, the pathogen-deactivating mechanism will continue to be activated.

Figures 19, 20:
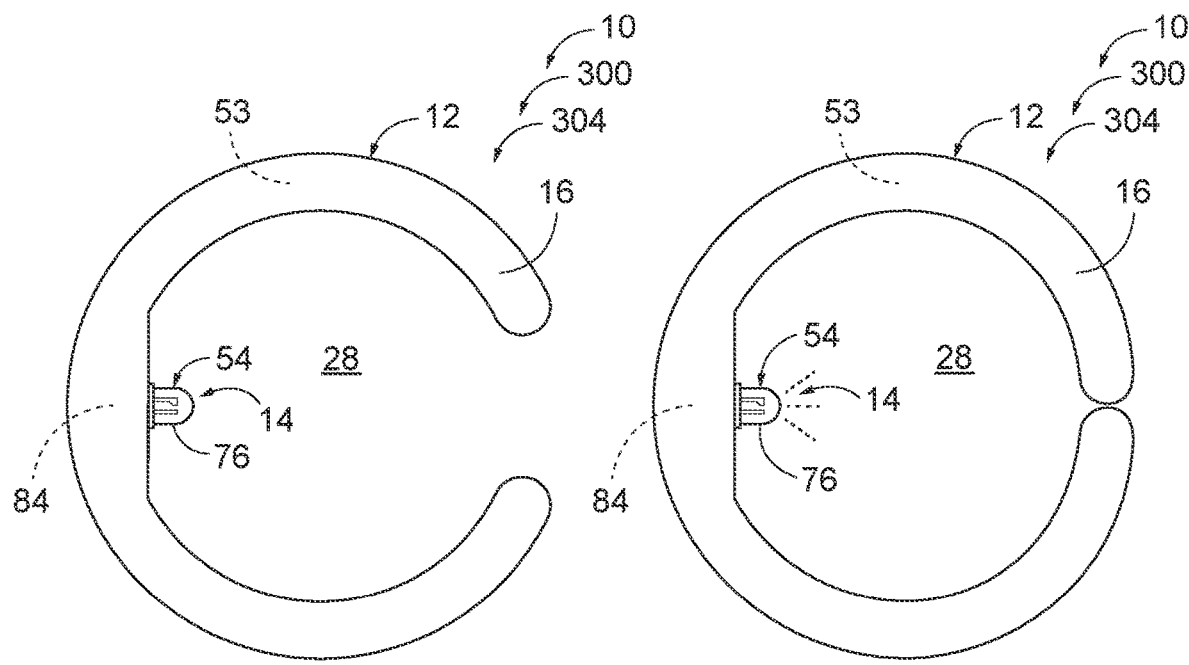
FIG. 19 is a schematic illustration representing example nose-mounted air-treatment devices, shown in a sprung conformation.
FIG. 20 is a schematic illustration representing the example nose-mounted air-treatment devices of FIG. 19, shown conformed to or toward a flexed conformation.
Figure 21:
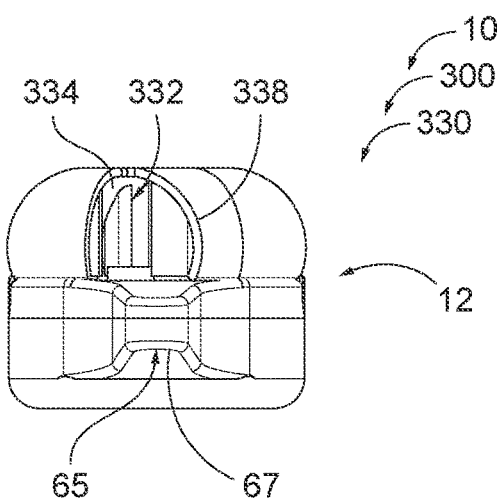
FIG. 21 is an end view of an example nose-mounted air-treatment device.
Figures 22, 23:
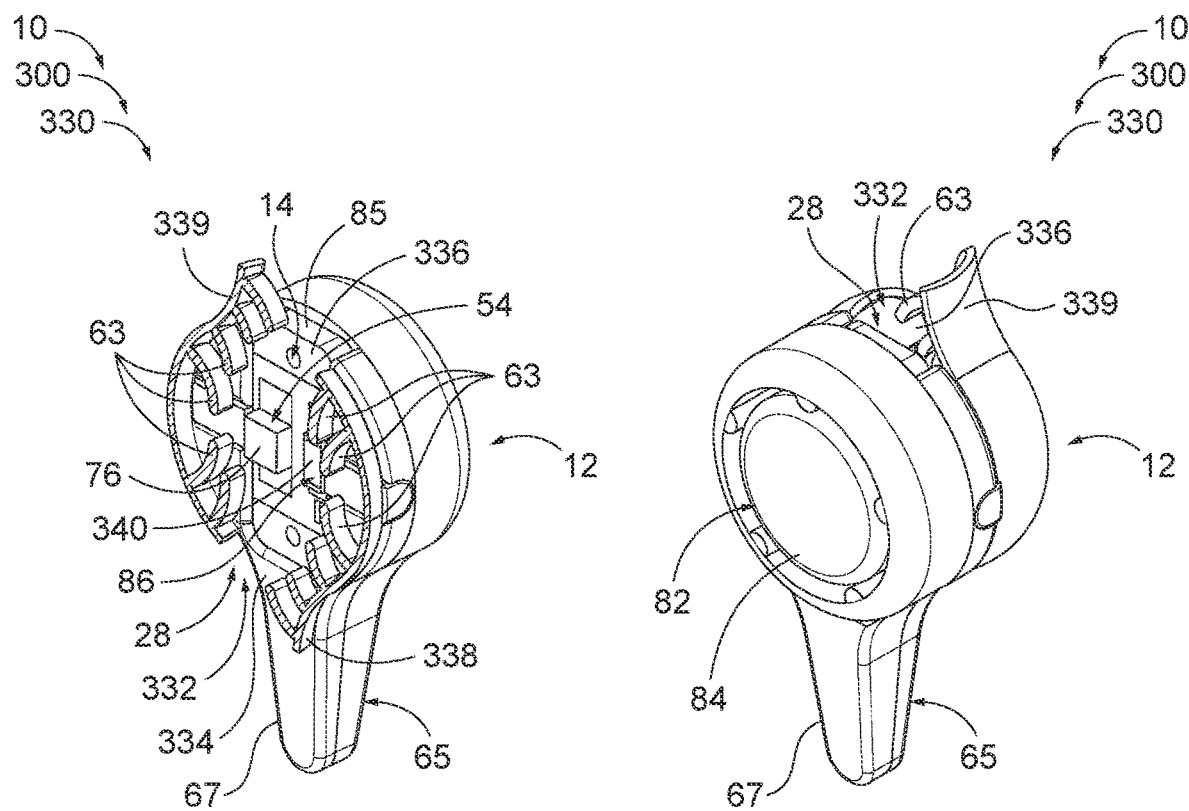
FIG. 22 is an isometric front cross-sectional view of the nose-mounted air-treatment device of FIG. 21.
FIG. 23 is an isometric rear view of the nose-mounted air-treatment device of FIG. 21.
Figure 24:
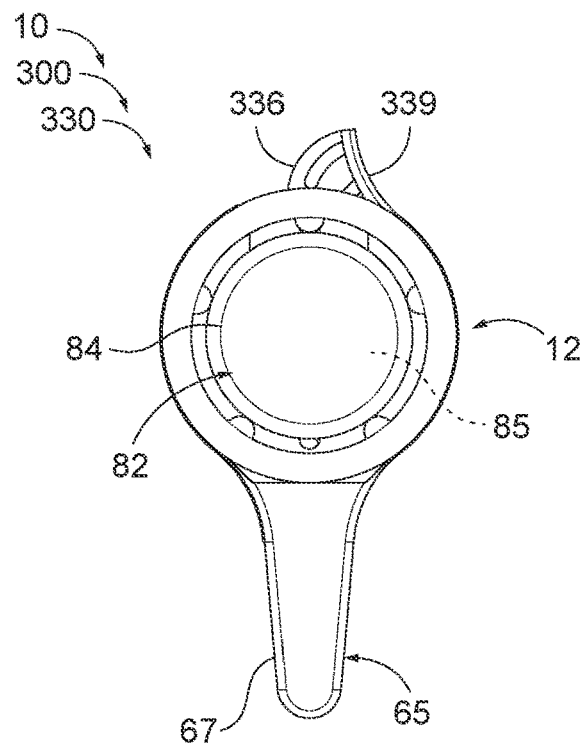
FIG. 24 is a rear view of the nose-mounted air-treatment device of FIG. 21.
Figure 25:
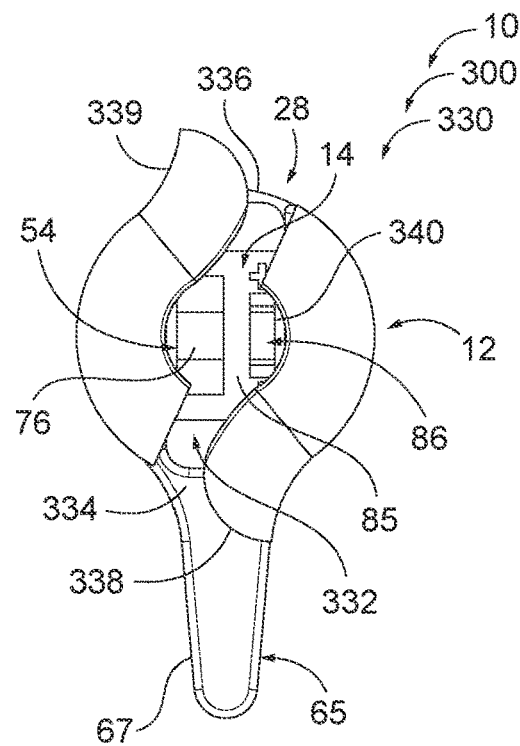
FIG. 25 is a front view of the nose-mounted air-treatment device of FIG. 21.
Figure 26:
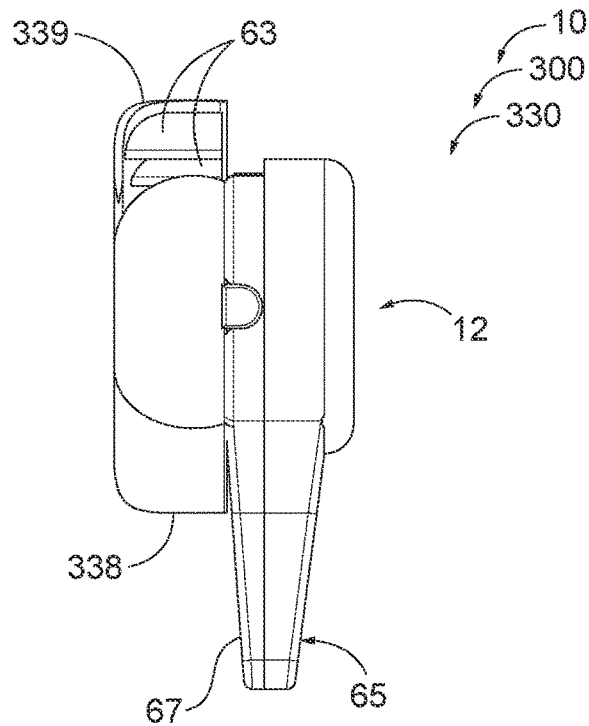
FIG. 26 is a side view of the nose-mounted air-treatment device of FIG. 21.
Figure 27:
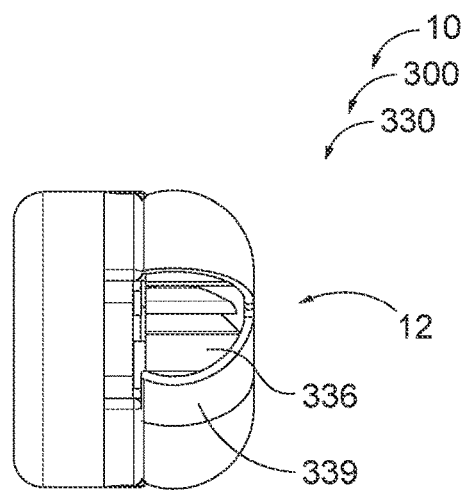
FIG. 27 is an end view of the nose-mounted air-treatment device of FIG. 21.
Figures 28, 29:
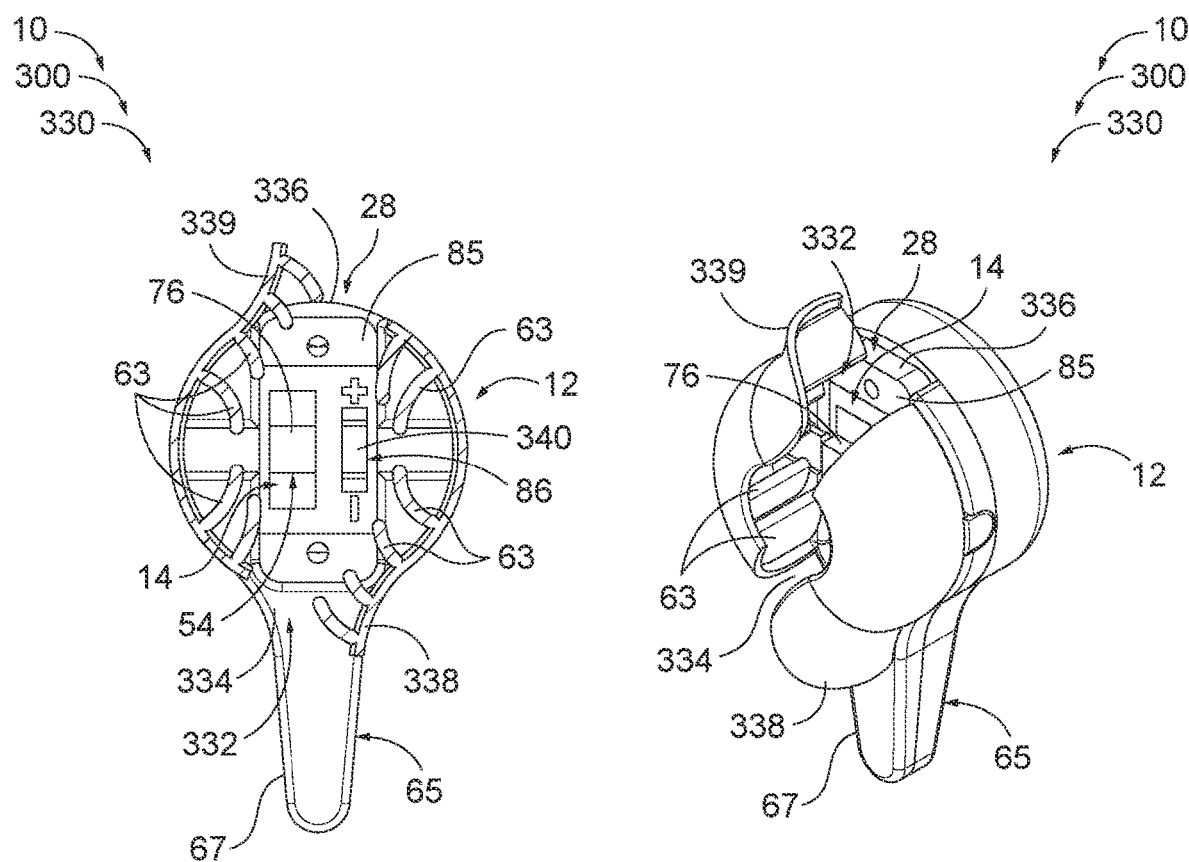
FIG. 28 is a cross-sectional front view of the nose-mounted air-treatment device of FIG. 21.
FIG. 29 is an isometric front view of the nose-mounted air-treatment device of FIG. 21

Example device 304 is illustrated in FIGS. 19 and 20. Similar to devices 310 and 302, device 304 is an example of a nose-mounted device 300 that is configured to be inserted into and retained within a nostril 112. The body 12 of device 304 comprises a resilient material 16 and is configured to be compressed from a sprung conformation (FIG. 19) to or toward a flexed conformation (FIG. 20) for operative insertion into a nostril 112. As illustrated, the body 12 of device 304 is configured to be compressed upon a user engaging and compressing opposing sides of the body 12 toward each other. Once operatively positioned within a nostril 112, release of the compressive force on the body 12 causes the body 12 to spring back toward the sprung conformation (FIG. 19) so that the body 12 engages the inside surface of the nostril 112 in a friction-fit arrangement to be retained within the nostril 112. Body 12 of device 302 defines and only partially circumscribes a void 28 when the body is in the sprung conformation. The body 12 supports a pathogen-deactivating mechanism 14 that comprises an LED 76 that, when activated, emits light within the void 28 to deactivate pathogens as air passes through the void 28 as a result of a user breathing. Device 302 may comprise an internal switch 53 configured to automatically activate the pathogen-deactivating mechanism 14 upon the body 12 being compressed away from the sprung conformation. Accordingly, when a user compresses the body 12 for insertion into a nostril 112, the pathogen-deactivating mechanism 14 will be activated, and when the body 12 is retained away from the sprung conformation as a result of engagement with the inside of the nostril 112, the pathogen-deactivating mechanism will continue to be activated.

Example device 330 is illustrated in FIGS. 21-29. Device 330 is another example of a nose-mounted device 300 that is configured to be inserted into and retained within a nostril 112 of the living individual 102. The body 12 of device 330 comprises a projection 67 that is configured to engage the superior region of as nasal vestibule and to wedge or urge the body 12 against an inside, opposite surface of the nostril 112.

The body 12 of device 330 defines an open void 28 and a plurality of baffles 63 extending into the void 28. The baffles 63 of device 330 are arcuate in shape and extend from opposing sides of the void 28 to create or otherwise define a central channel region 332, but other configurations of baffles 63 are within the scope of the present disclosure. The body 12 of device 330 defines a first opening 334 to the void 28, adjacent to the projection 67, and a second opening 336 to the void, opposite the projection 67, with the central channel region 332 extending between the first opening 334 and the second opening 336.

Each of the first opening 334 and the second opening 336 are defined in part by a flared region 338,339 of the body 12. These flared regions 338, 339 when present, may aid in making the device 330 more comfortable within the nostril and also may facilitate airflow through the void 28 when the living individual 102 is breathing. In particular, flared region 338, adjacent to first opening 334, is configured to nestle against the inferior side of the opening of the user's nostril when the device 330 is operatively installed. In some examples, a flared region may be constructed of a resilient, flexible, and/or soft material configured to generally conform to the shape of the portion of the living individual 102 against which it is positioned when the device 330 is donned or to otherwise provide for a comfortable fit of the device 330. Additionally or alternatively, the flared regions 338, 339 or other portions of the body 12 of device 330 may be repositionable relative to other portions of the body 12, such as to permit a user to selectively adjust the position of the flared regions 338, 339 relative to the projection 67. For example, the portion of the body 12 comprising the flared regions 338, 339 may be rotatable relative to the portion of the body 12 comprising the projection 67, so that a user may configure the device 330 in a manner that is most comfortable and fitting to the particular user's anatomy.

The body 12 of device 330 supports a pathogen-deactivating mechanism 14 that comprises an LED 76 that, when activated, emits light within the void 28 to deactivate pathogens as air passes through the void 28 as a result of a user breathing. Device 330 further comprises a user control 86 in the form of an on/off switch 340, and a power source 82 in the form of a battery 84.

Example device 306 is illustrated in FIGS. 30 and 31. Device 306 is an example of a nose-mounted device 300 that is configured to pinch the septal region 108 of a nose and emit light into both nostrils 112 of a living individual 102. The body 12 of device 306 may be described as comprising two arms 322 and a bridge 324 interconnecting the arms 322 and collectively defining a C- or U-shape, generally. Body 12 of device 306 comprises a resilient material 16 and is configured to be tensioned from a sprung conformation (FIG. 30) to or toward a flexed conformation (FIG. 31) for operative placement of the arms 322 on opposing sides of a septal region 108 of a nose 104. Body 12 may be constructed with first and second body parts 18 and 20, such as according to the cross-sectional representation of FIG. 3, with the second body part 20 defining a spring. Once operatively positioned with the arms 322 on opposing sides of a septal region 108, release of the tensile force on the body 12 causes the body to spring back toward the sprung conformation (FIG. 30), so that the arms 322 engage the opposing sides of the septal region 108 in a pinching configuration to be retained on the nose 104. The body 12 supports two pathogen-deactivating mechanisms 14 that each comprise an LED 76 that, when activated, emits light within respective nostrils 112 to deactivate pathogens as air passes through the nostrils 112 as a result of a user breathing. Device 306 may comprise an internal switch 53 configured to automatically activate the pathogen-deactivating mechanisms 14 upon the body 12 being tensioned away from the sprung conformation. Accordingly, when a user tensions the body 12 for placement of the arms 322 within the user's nostrils 112, the pathogen-deactivating mechanisms 14 will be activated, and when the body 12 is retained away from the sprung conformation as a result of the thickness of the septal region 108 restricting the body 12 from returning fully to the sprung conformation, the pathogen-deactivating mechanisms 14 will continue to be activated.

Example device 308 is illustrated in FIGS. 32 and 33. Device 308 is an example of a nose-mounted device 300 similar to device 306 for operative retention on a septal region 108 of a nose 104, but with the arms 322 of the body 12 defining and fully circumscribing two voids 28, within each of which an LED 76 is supported. The inward surfaces 64 of the body 12 may be reflective as discussed herein to concentrate the light emitted by the LEDs 76.

Figure 36:
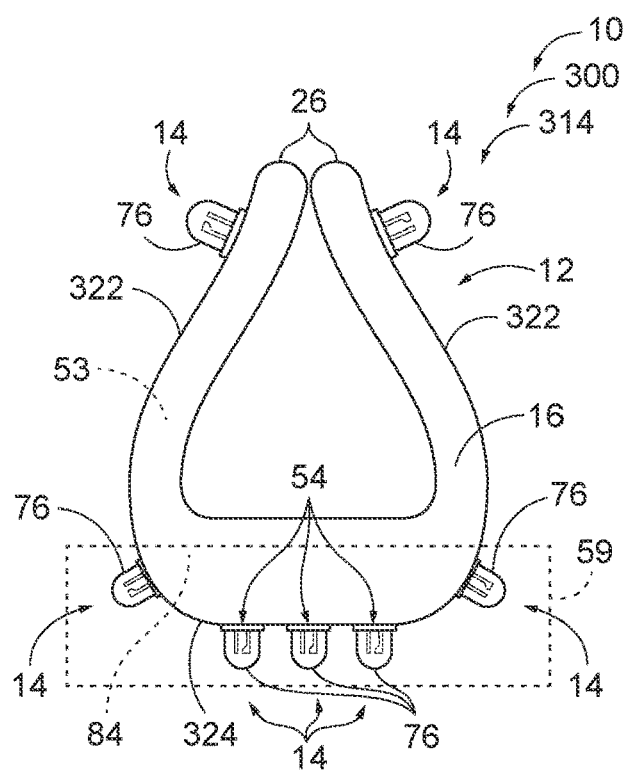
FIG. 36 is a schematic illustration representing example nose-mounted air-treatment devices, shown in a sprung conformation.
Figure 37:
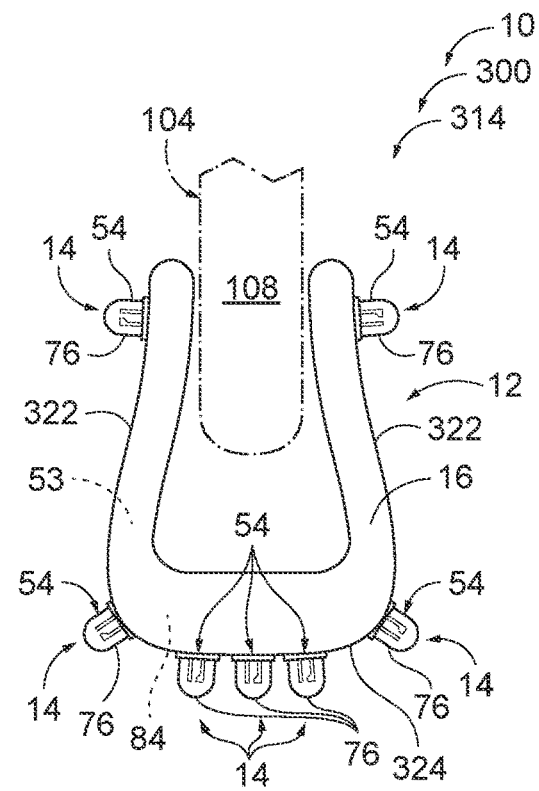
FIG. 37 is a schematic illustration representing the example nose-mounted air-treatment devices of FIG. 36, shown conformed to or toward a flexed conformation.
Figure 38:
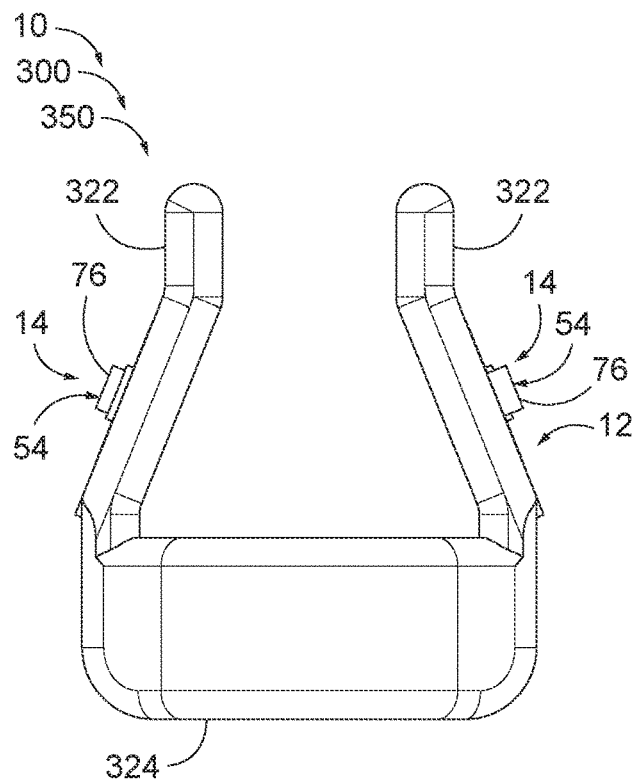
FIG. 38 is a side view of an example nose-mounted air-treatment device.
Figure 39:
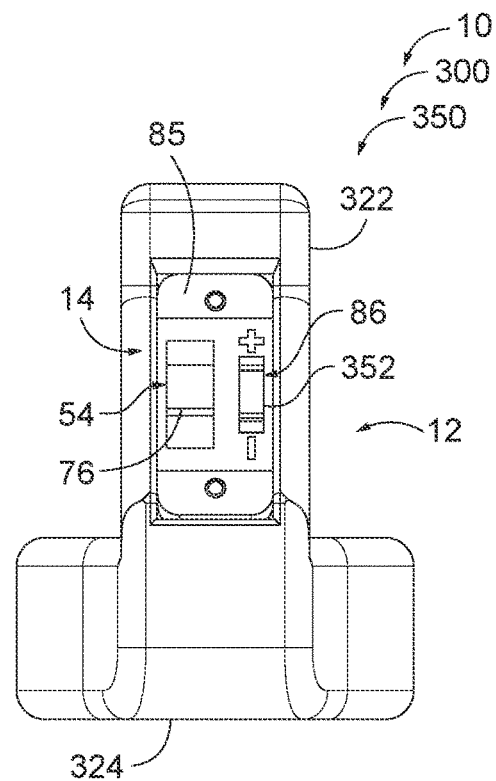
FIG. 39 is another side view of the nose-mounted air-treatment device of FIG. 38.
Figure 40:
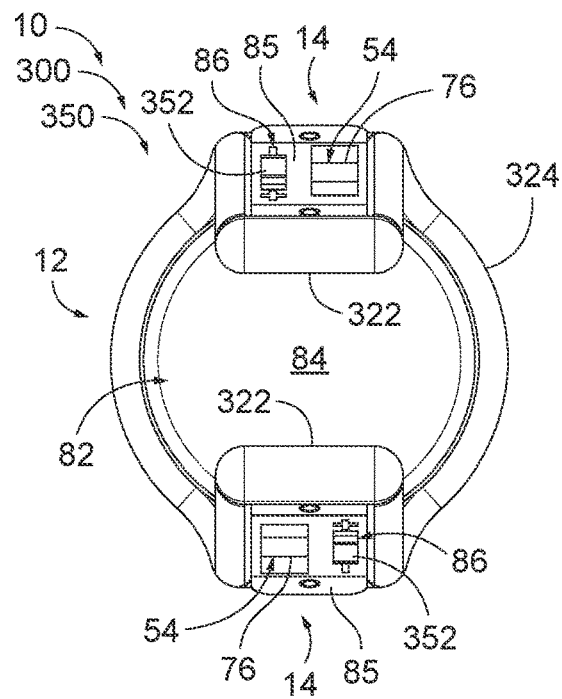
FIG. 40 is a rear view of the nose-mounted air-treatment device of FIG. 38.
Figure 41:
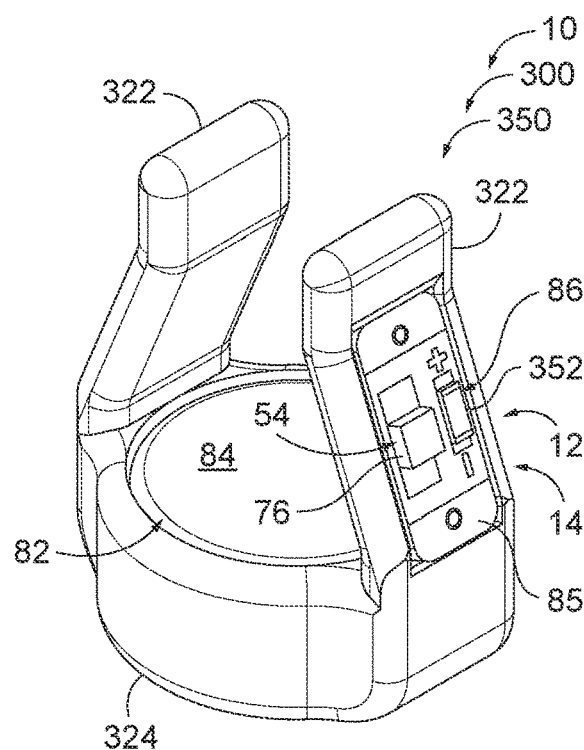
FIG. 41 is a rear isometric view of the nose-mounted air-treatment device of FIG. 38.

Example device 314 is illustrated in FIGS. 36 and 37. Device 314 is an example of a nose-mounted device 300 similar to device 306 for operative retention on a septal region 108 of a nose 104, but further comprising additional LEDs 76 supported along the bridge 324 of the body 12 and configured to emit light downward from a user's nose 104 in front of the user's mouth 106, so that device 314 not only deactivates pathogens entering and exiting the nose 104 but also deactivates pathogens entering and exiting the mouth 106 as a user breathes. As schematically represented in FIG. 36, body 12 of device 308 may further comprise or define additional structure 59 that is configured to direct light emitted by the bridge-mounted LEDs 76 as a curtain 55 of light in front of a user's mouth 106.

Example device 350 is illustrated in FIGS. 38-41. Device 350 is another example of a nose-mounted device 300 similar to device 306 for operative retention on a septal region 108 of a nose 104. Like device 306, the body 12 of device 350 comprises two arms 322 and a bridge 324 that interconnects the arms 322. The body 12 supports two pathogen-deactivating mechanisms 14 that each comprise an LED 76 that, when activated, emits light within respective nostrils 112 to deactivate pathogens as air passes through the nostrils 112 as a result of a user breathing. Device 350 comprises user controls 86 in the form of an on/off switch 352 corresponding to each LED 76. The bridge 324 houses a battery 84.

Figure 34:
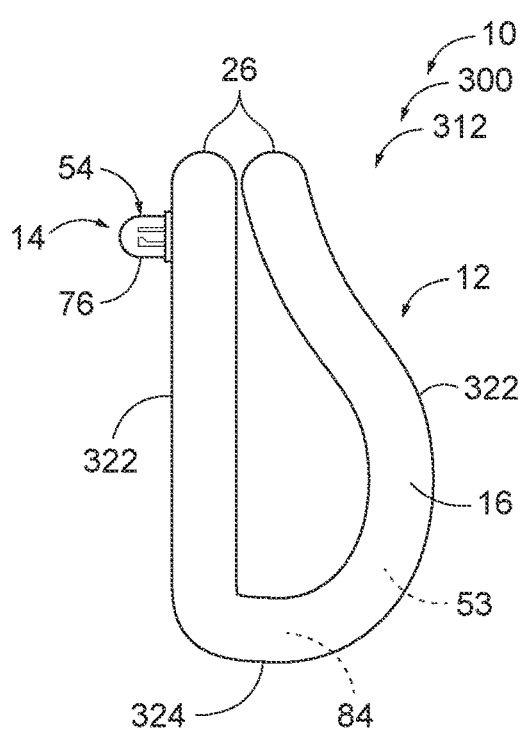
FIG. 34 is a schematic illustration representing example nose-mounted air-treatment devices, shown in a sprung conformation.
Figure 35:
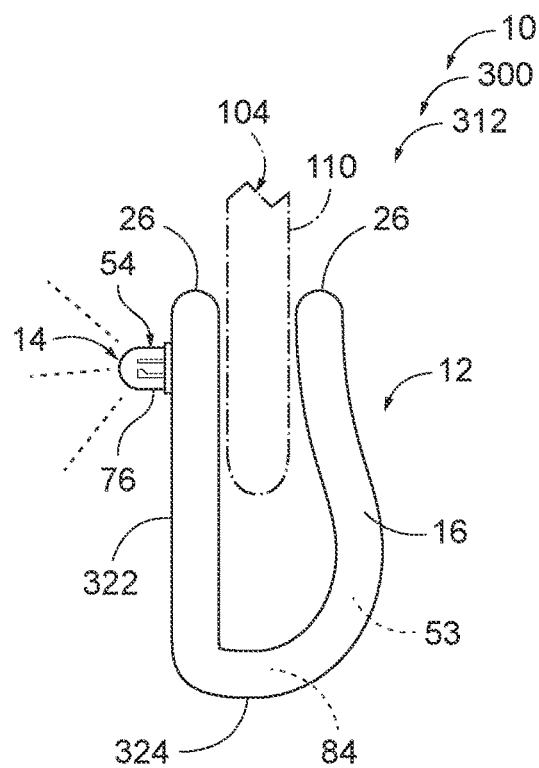
FIG. 35 is a schematic illustration representing the example nose-mounted air-treatment devices of FIG. 34, shown conformed to or toward a flexed conformation.

Example device 312 is illustrated in FIGS. 34 and 35. Device 312 is another example of a nose-mounted device 300 that is configured to operatively position an LED 76 within a nostril 112 similar to devices 306, 308, and 314; however, device 312 only has a pathogen-deactivating mechanism 14 on one of its two arms 322. Accordingly, device 312 is configured to be operatively retained on a wing 110 of a user's nose 104 and is intended to be used in a pair of devices 312, with one device 312 on each wing 110 of a user's nose 104.

FIGS. 42 and 43 provide examples of tooth-mounted devices 400 that are configured to be secured to a tooth 120 of the living individual 102. In FIG. 42, an example tooth-mounted device 402 is shown and includes an anchor 48 that is secured, such as adhesively secured, to the tooth 120 of the living individual. Anchor 48 may be, form a portion of, or be secured to an orthodontic appliance 148, such as an orthodontic bracket.

In FIG. 43, an example tooth-mounted device 404 is shown and includes a band 44 that is sized to extend at least partially, and optionally fully, around the tooth 120. The body 12 of the device is removably, semi-permanently, or permanently secured to the band 44. The band 44 may be described as forming a portion of the device 10 and/or as an anchor 48 to which at least the body 12 and/or pathogen-deactivating mechanism 14 thereof is operatively coupled and positioned to deactivate pathogens in the living individual's mouth, such as when the user inhales or exhales through the living individual's mouth.

An example of a tooth 120 is a molar or other tooth that extends from the maxilla of the living individual's mouth, but any maxillary or mandibular tooth may be utilized within the scope of the present disclosure. In the examples of FIGS. 42 and 43, it is within the scope of the present disclosure that at least pathogen-deactivating mechanism 14 and optionally the body 12 of the device may be removably, semi-permanently, or permanently secured to the tooth 120, the band 44, the orthodontic appliance 148, and/or the anchor 48.

Figure 48:
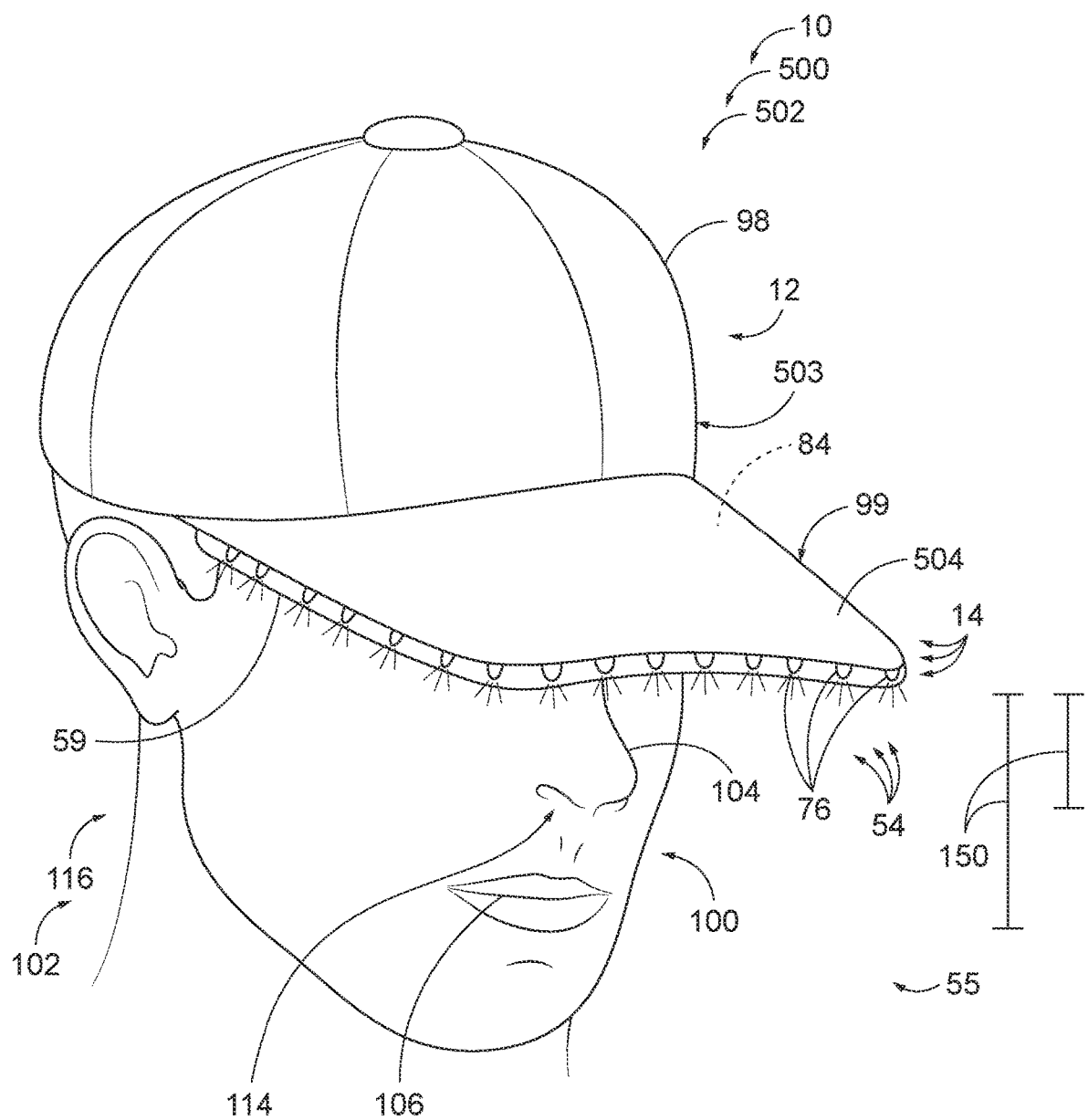
FIG. 48 is a schematic illustration representing example head-mounted body-worn air-treatment devices, shown being worn by a living individual.

In FIG. 48, example device 502 is an example of a head-mounted device 500, namely, a device 10 that is configured to be mounted to the head 116 of the living individual 102. Example device 502 is an example of a head-mounted device 500 in which the body 12 is, forms a portion of, or is coupled to a cap 503. More specifically, the cap 503 comprises a head mount 98 that secures the device to the living individual's head, and a support 99 that extends from the head mount and at least partially supports at least the pathogen-deactivating mechanism 14 of the body 12 of the device. In the illustrated example, the support 99 is in the form a bill 504 of the cap 503. The body 12 of the device 10 may be integrated into the bill 504, may form at least a portion of the bill 504, or may be removably, semi-permanently, or permanently coupled to the bill 504. As illustrated, the bill 504 and/or body 12 supports at least one light source 54 (and optionally a plurality of light sources, such as LEDs 76) and optionally at least one structure 59 for directing light from the LEDs 76 as a curtain 55 of light in front of a user's face, so that air being breathed by the user, whether via the user's nose or mouth, will pass through the curtain 55 of light.

Figure 49:
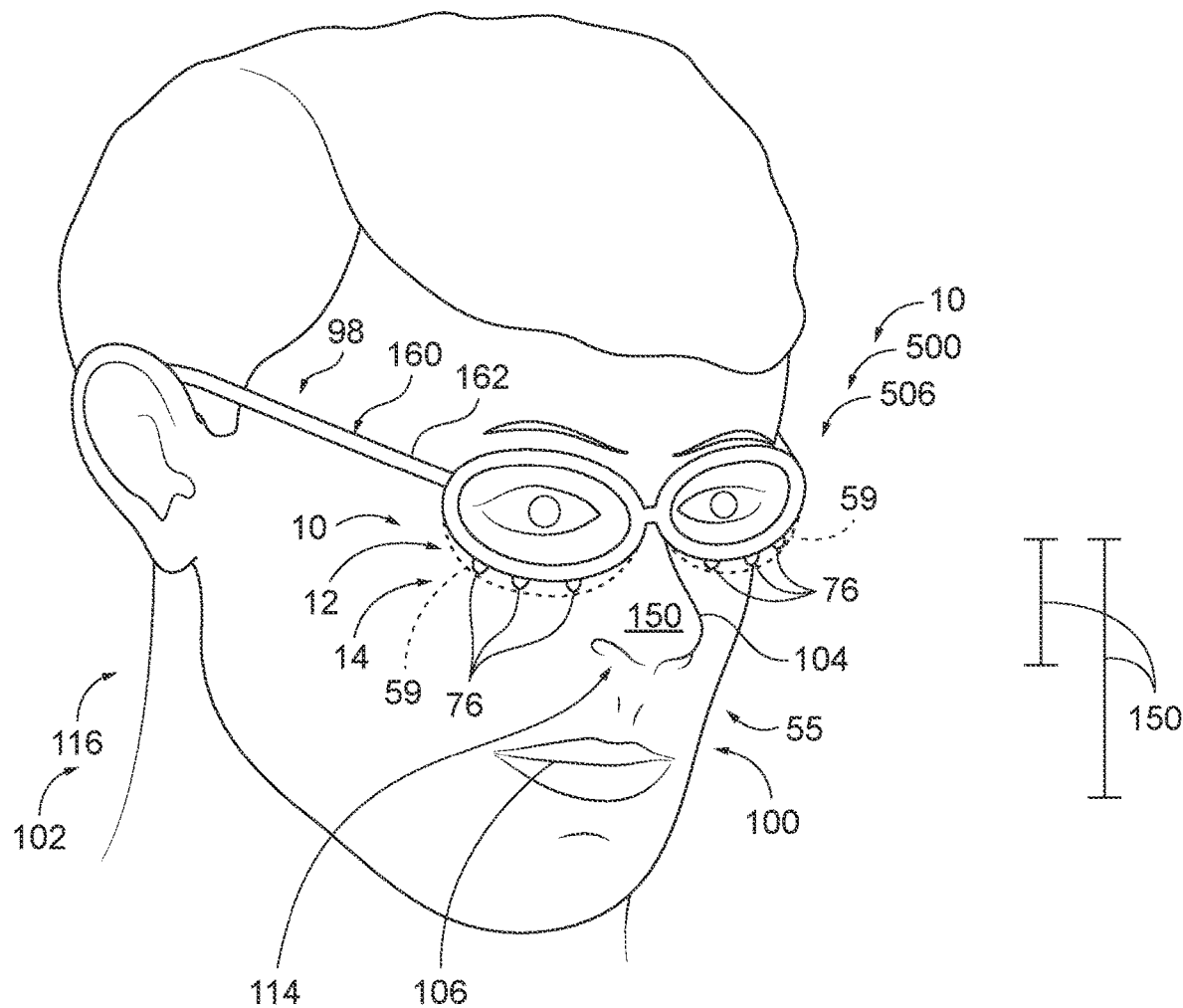
FIG. 49 is a schematic illustration representing example head-mounted body-worn air-treatment devices, shown being worn by a living individual.

In FIG. 49, example device 506 is another example of a head-mounted device 500. In this example, the head mount 98 is eyewear 160, or at least a frame 162 portion thereof. Eyewear 160 additionally or alternatively may be or may be referred to as eyeglasses 160, sunglasses 160, non-prescription eyewear 160, and/or prescription eyewear 160. The body 12 of device 506 may be, may form a portion of, or may be coupled to the frame 162 of the eyewear 160. As illustrated, the frame 162 and/or body 12 supports at least one light source 54 (and optionally a plurality of light sources, such as LEDs 76) and optionally a structure 59 for directing light from the LEDs 76 as a curtain 55 of light in front of a user's face, so that air being breathed by the user, whether via the user's nose or mouth, will pass through the curtain 55 of light.

Figure 50:
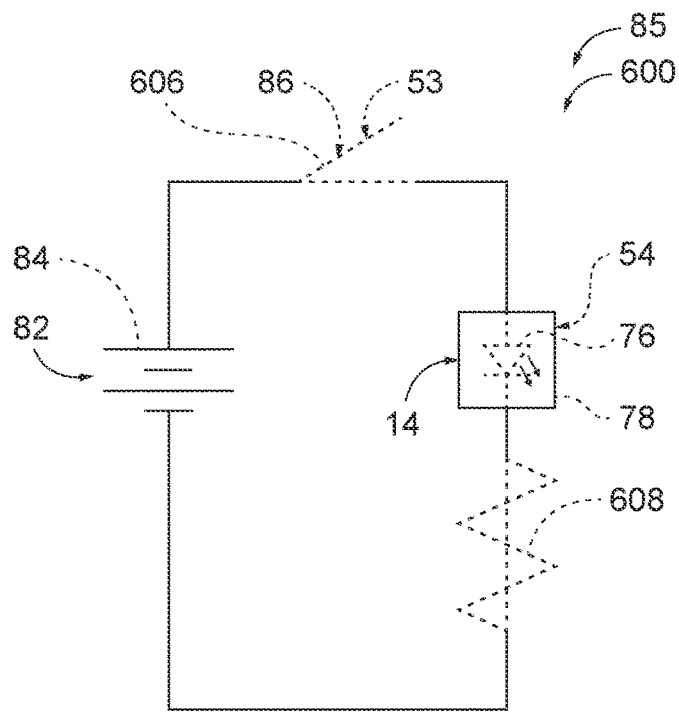
FIG. 50 is a schematic circuit diagram representing example electronics of body-worn air-treatment devices.
Figure 51:
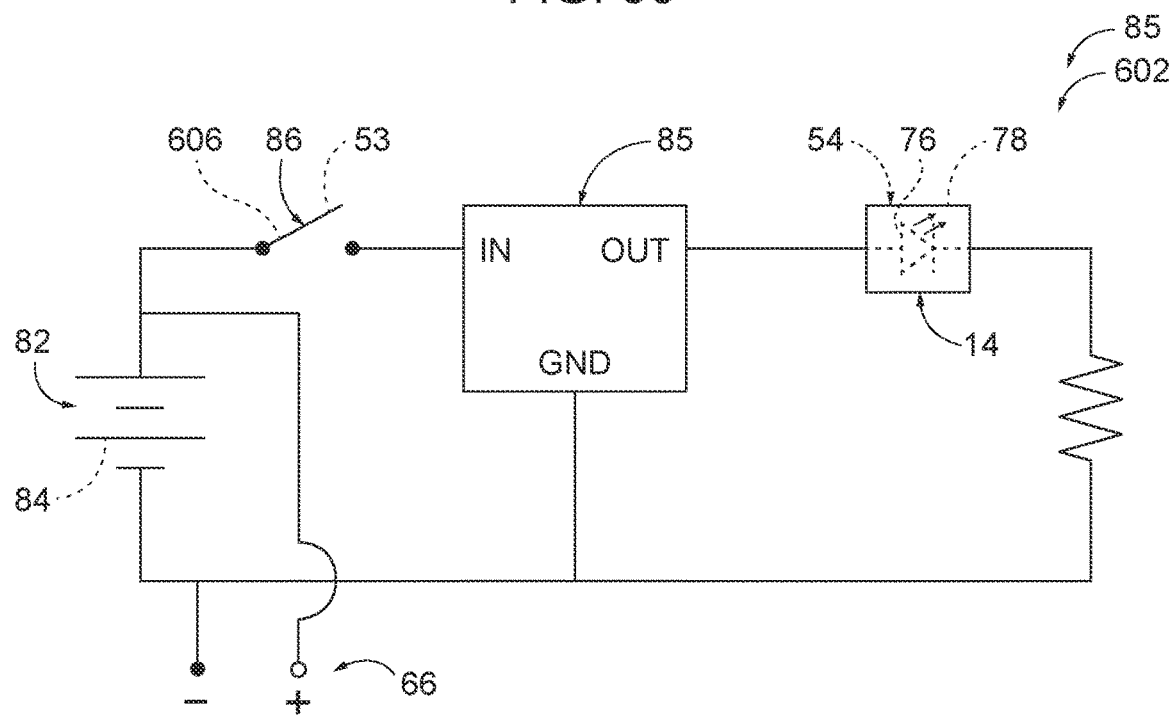
FIG. 51 is another schematic circuit diagram representing example electronics of body-worn air-treatment devices.

FIGS. 50-52 schematically represent example electronics (e.g., controllers 85) of devices 10 for powering and controlling the pathogen-deactivating mechanism 14 thereof, such as a light source 54 in the form of an LED 76 or an electroceutical fabric 78 or other structure that creates an electric field 77, as discussed herein. Example electronics 600 of FIG. 50 comprises a simple circuit having a power source 82, an optional user control 86 in the form of an on/off switch 606, which optionally may be an internal switch 53, and an optional resister 608. Example electronics 602 of FIG. 51 further comprises a controller 85, such as a microcontroller, and a charging port 66. Example electronics 604 of FIG. 52 further comprises a wireless transceiver 88, an external trigger or sensor 610, which optionally may be described as a user control 86, and an audible indicator 94 in the form of a speaker 612.

FIG. 53 schematically provides a flowchart that represents illustrative, non-exclusive examples of methods 200 according to the present disclosure and/or uses of devices 10 according to the present disclosure to deactivate pathogens entering and/or exiting the respiratory tract inlet 100 of the living individual 102. In FIG. 53, some steps are illustrated in dashed boxes indicating that such steps may be optional or may correspond to an optional version of a method according to the present disclosure. The methods 200 and steps illustrated in FIG. 53 are not limiting and other methods and steps are within the scope of the present disclosure, including methods 200 having greater than or fewer than the number of steps illustrated, as understood from the discussions herein.

Methods 200 comprise deactivating 202 pathogens proximate a respiratory tract inlet 100 of a living individual 102. In some methods 200, the deactivating 202 comprises emitting 204 light within a germicidal spectrum proximate to the respiratory tract inlet 100 of the living individual 102. In some such methods 200, the emitting 204 comprises emitting light within a nostril 112 of a nose 104 of the living individual 102. In some methods 200, the emitting 204 comprises emitting light within a mouth 106 of the living individual 102. In some such methods 200, the emitting 204 comprises emitting a curtain 55 of light proximate to a nasal cavity 114 and/or a mouth 106 of the living individual 102. In some methods 200, the deactivating 202 comprises generating 206 an electric field 77, through which air flows proximate to the respiratory tract inlet 100 of the living individual 102 when the living individual 102 breathes. Some methods 200 are performed by a body-worn air-treatment device 10 according to the present disclosure.

Illustrative, non-exclusive examples of body-worn air-treatment devices, uses thereof, and methods of deactivating pathogens according to the present disclosure are described in the following enumerated paragraphs:

A. A body-worn air-treatment device (10), comprising:
a body (12) configured to be selectively coupled proximate a respiratory tract inlet (100) of a living individual (102); and
a pathogen-deactivating mechanism (14) supported by the body (12).

A1. The body-worn air-treatment device (10) of paragraph A, wherein the body (12) is configured to be selectively coupled to a nose (104) of the living individual (102).

A2. The body-worn air-treatment device (10) of paragraph A, wherein the body (12) is configured to be selectively coupled to a tooth (120) of the living individual (102).

A2.1. The body-worn air-treatment device (10) of paragraph A2, wherein the body (12) is configured to be coupled to a palatal surface of the tooth (120) of the living individual (102).

A2.2. The body-worn air-treatment device (10) of any of any of paragraphs A2-A2.1, wherein the body (12) is configured to be coupled to a tooth (120) of an upper jaw of the living individual (102).

A2.3. The body-worn air-treatment device (10) of any of paragraphs A2-A2.2, wherein the body (12) includes a band (44) that extends around the tooth (120).

A2.3.1. The body-worn air-treatment device (10) of paragraph A2.3, wherein the band (44) and the body (12) collectively define a cavity (46) sized to receive the tooth (120) of the living individual (102) therein.

A2.3.2. The body-worn air-treatment device (10) of any of paragraphs A2.3-A2.3.1, wherein the band (44) has a length that is selectively adjustable.

A2.4. The body-worn air-treatment device (10) of any of paragraphs A2-A2.3.2, wherein the body (12) includes a first sub-portion (65) that is coupled to a first surface of the tooth (120) and a second sub-portion (65) that is coupled to a second surface of the tooth (120), with the first and second surfaces of the tooth (120) being generally opposed to each other.

A2.5. The body-worn air-treatment device (10) of paragraph A2.4, wherein a/the band (44) interconnects the first and second sub-portions (65).

A2.6. The body-worn air-treatment device (10) of any of paragraphs A2.4-A2.5, wherein a/the band (44) includes wires (414) that establish electrical communication between the first sub-portion (65) and the second sub-portion (65).

A2.7. The body-worn air-treatment device (10) of any of paragraphs A2-A2.6, wherein the body (12) includes a conformance layer (420) on a tooth-facing surface (422) of the body (12), and wherein the conformance layer (420) is formed from a resiliently compressible material.

A3. The body-worn air-treatment device (10) of any of paragraphs A-A2.7, wherein the body (12) comprises a resilient material (16).

A4. The body-worn air-treatment device (10) of any of paragraphs A-A3, wherein the body (12) is composed of a material that is compatible with tissue of the living individual (102).

A5. The body-worn air-treatment device (10) of any of paragraphs A-A4, wherein the body (12) comprises a first body part (18) composed of a first resilient material (22) and a second body part (20) at least partially embedded within the first body part (18) and composed of a second resilient material (24), and wherein the second resilient material (24) has a spring constant greater than a spring constant of the first resilient material (22).

A6. The body-worn air-treatment device (10) of any of paragraphs A-A5, wherein the body (12) is resiliently conformable amongst a range of conformations comprising a sprung conformation and a flexed conformation, wherein the body (12) is biased toward the sprung conformation.

A6.1. The body-worn air-treatment device (10) of paragraph A6, wherein the at least one pathogen-deactivating mechanism (14) is configured to be automatically activated when the body (12) is within a predetermined subset of conformations of the range of conformations.

A6.1.1. The body-worn air-treatment device (10) of paragraph A6.1, wherein the predetermined subset of conformations includes the sprung conformation.

A6.1.2. The body-worn air-treatment device (10) of paragraph A6.1, wherein the predetermined subset of conformations includes the flexed conformation.

A6.2. The body-worn air-treatment device (10) of any of paragraphs A6-A6.1.2, wherein the at least one pathogen-deactivating mechanism (14) is configured to be automatically activated when the body (12) is not in the sprung conformation.

A6.3. The body-worn air-treatment device (10) of any of paragraphs A6-A6.1.2, wherein the at least one pathogen-deactivating mechanism (14) is configured to be automatically activated when the body (12) is not in the flexed conformation.

A6.4. The body-worn air-treatment device (10) of any of paragraphs A6-A6.3, wherein the flexed conformation is a tensioned conformation.

A6.5. The body-worn air-treatment device (10) of any of paragraphs A6-A6.4, wherein the body (12) is configured to selectively pinch a portion of a/the nose (104) of the living individual (102).

A6.6. The body-worn air-treatment device (10) of any of paragraphs A6-A6.5, wherein the body (12) is configured to selectively engage opposite sides of a/the portion of a/the nose (104) of the living individual (102).

A6.6.1. The body-worn air-treatment device (10) of paragraph A6.6, wherein the portion of the nose (104) is one of a septal region (108) of the nose (104) or a wing (110) of the nose (104).

A6.7 The body-worn air-treatment device (10) of any of paragraphs A6-A6.6.1, wherein the body (12) is configured to be selectively expanded toward the flexed conformation responsive to an external force on the body (12).

A6.8. The body-worn air-treatment device (10) of any of paragraphs A6-A6.7, wherein the body (12) comprises two end regions (26), wherein the two end regions (26) are closer together when the body (12) is in the sprung conformation than in the flexed conformation, and wherein the two end regions (26) are configured to engage opposite sides of a/the portion of a/the nose (104) of the living individual (102).

A6.8.1. The body-worn air-treatment device (10) of paragraph A6.8, wherein in the sprung conformation, the two end regions (26) engage each other.

A6.9. The body-worn air-treatment device (10) of any of paragraphs A6-A6.3, wherein the flexed conformation is a compressed conformation.

A6.10. The body-worn air-treatment device (10) of any of paragraphs A6-A6.3 and A6.9, wherein the body (12) has an outermost/external dimension (30) that is greatest when the body (12) is in the sprung conformation.

A6.11. The body-worn air-treatment device (10) of any of paragraphs A6-A6.3 and A6.9-A6.10, wherein the body (12) is configured to be selectively compressed toward the flexed conformation responsive to an external force on the body (12).

A6.12. The body-worn air-treatment device (10) of any of paragraphs A6-A6.3 and A6.9-A6.11, wherein the body (12) is configured to be selectively compressed toward the flexed conformation for insertion into a nostril (112) of the nose (104) and released to expand toward the sprung conformation to engage inside surfaces of the nostril (112) and be retained at least partially within the nostril (112).

A6.13. The body-worn air-treatment device (10) of any of paragraphs A6-A6.3 and A6.9-A6.12, wherein the body (12) is sized to be positioned fully within the nostril (112).

A6.14. The body-worn air-treatment device (10) of any of paragraphs A6-A6.3 and A6.9-A6.13, wherein the body (12) at least partially defines a void (28) that is and/or extends inward, optionally radially inward, from an exterior, or exterior surface, of the body (12).

A6.14.1. The body-worn air-treatment device (10) of paragraph A6.14, wherein the body (12) has a longitudinal axis (32) extending through the void (28), and wherein the body (12) is configured to be selectively squeezed toward the longitudinal axis (32) to conform the body (12) toward the flexed conformation.

A6.14.2. The body-worn air-treatment device (10) of any of paragraphs A6.14-A6.14.1, wherein the body (12) fully circumscribes the void (28).

A6.14.3. The body-worn air-treatment device (10) of any of paragraphs A6.14-A6.14.1, wherein the body (12) only partially circumscribes the void (28).

A6.14.4. The body-worn air-treatment device (10) of any of paragraphs A6.14-A6.14.3, wherein the void (28) is cylindrical, substantially cylindrical, or generally cylindrical.

A6.14.5. The body-worn air-treatment device (10) of any of paragraphs A6.14-A6.14.4, wherein the void (28) includes first and second spaced end regions (72), which optionally are first and second longitudinally spaced end regions (72).

A6.14.6. The body-worn air-treatment device (10) of paragraph A6.14.5, wherein the void (28) extends into the body (12) from the end regions (72) and a side wall of the body.

A6.14.7. The body-worn air-treatment device (10) of paragraph A6.14.6, wherein the void (28) defines openings on the end regions (72) of the body (12), and further wherein the void (28) defines a lateral opening extending between the openings on the end regions (72) of the body (12).

A6.14.8. The body-worn air-treatment device (10) of paragraph A6.14.7, wherein the lateral opening is configured to be at least partially closed during use of the device (10) to deactivate pathogens, and optionally wherein the lateral opening is configured to be at least partially closed by a portion of the living individual's body during use of the device (10) to deactivate pathogens.

A7. The body-worn air-treatment device (10) of any of paragraphs A-A6.14.8 wherein the body (12) comprises a magnetic assembly (33) for operatively positioning the at least one pathogen-deactivating mechanism (14) of the device (10) proximate to the respiratory tract inlet (100) of the living individual (102).

A7.1. The body-worn air-treatment device (10) of paragraph A7, wherein the magnetic assembly (33) comprises at least one magnet (34), and optionally at least two magnets (34).

A7.2. The body-worn air-treatment device (10) of any of paragraphs A7-A7.1, wherein the magnetic assembly (33) comprises at least one magnet (34) and a ferromagnetic element (36) configured to be selectively positioned within a magnetic field of the magnet (34).

A7.3. The body-worn air-treatment device (10) of paragraph A7.2, wherein the at least one magnet (34) and the ferromagnetic element (36) are configured to position the body (12) on opposing sides of a portion, optionally of a/the nose (104), of the living individual (102).

A7.4. The body-worn air-treatment device (10) of any of paragraphs A7.2-A7.3, wherein the at least one pathogen-deactivating mechanism (14) is configured to be automatically activated when the ferromagnetic element (36) is within a threshold distance from the magnet (34).

A7.5. The body-worn air-treatment device (10) of any of paragraphs A7.2-A7.4, wherein the ferromagnetic element (36) is a second magnet.

A8. The body-worn air-treatment device (10) of any of paragraphs A-A7.5, wherein the body (12) comprises an adhesive surface (38) configured to be selectively affixed proximate to the respiratory tract inlet (100) of the living individual (102).

A8.1. The body-worn air-treatment device (10) of paragraph A8, wherein the adhesive surface (38) is composed of an adhesive (40) that is compatible with human tissue. A8.2. The body-worn air-treatment device (10) of any of paragraphs A8-A8.1, further comprising a backing (42) releasably coupled to the adhesive surface (38).

A9. The body-worn air-treatment device (10) of any of paragraphs A-A6.4 and A7-A8.2, wherein the body (12) is configured to be selectively coupled to a/the tooth (120) of the living individual (102).

A9.1. The body-worn air-treatment device (10) of paragraph A9, wherein the body (12) includes a/the band (44) sized to extend at least partially, and optionally fully, around the tooth (120).

A9.2. The body-worn air-treatment device (10) of any of paragraphs A9-A9.1, wherein the body (12) defines a/the cavity (46) sized to receive at least a portion of the tooth (120) to couple the body (12) to the tooth (120).

A9.3. The body-worn air-treatment device (10) of any of paragraphs A9-A9.2, wherein the body (12) comprises a/the magnet (34) configured to couple the body (12) relative to the tooth (120), optionally to a/the band (44) sized to extend at least partially, and optionally fully, around the tooth (120), or to an anchor (48) configured to be secured to the tooth (120).

A10. The body-worn air-treatment device (10) of any of paragraphs A-A9.3, further comprising an/the anchor (48) configured to be secured to at least one of a/the tooth (120) or a/the nose (104) of the living individual (102), and wherein the body (12) is configured to be removably coupled to the anchor (48).

A10.1. The body-worn air-treatment device (10) of paragraph A10, wherein the anchor (48) comprises at least one of an orthodontic appliance (148), a dental implant, a nasal piercing, or a nasal anchor.

A10.2. The body-worn air-treatment device (10) of any of paragraphs A10-A10.1, wherein the anchor (48) is configured to be adhesively bonded to the tooth (120).

A10.3. The body-worn air-treatment device (10) of any of paragraphs A10-A10.2, wherein the anchor (48) is configured to extend at least partially, and optionally fully, around the tooth (120).

A10.4. The body-worn air-treatment device (10) of any of paragraphs A10-A10.3, wherein the anchor (48) is configured to be removably clipped to one of a/the septal region (108) of the nose (104) or a/the wing (110) of the nose (104).

A10.5. The body-worn air-treatment device (10) of any of paragraphs A10-A10.4, wherein the anchor (48) is configured to extend through at least a/the portion of the nose (104).

A10.6. The body-worn air-treatment device (10) of any of paragraphs A10-A10.5, wherein the body (12) is configured to at least one of mechanically or magnetically be coupled to the anchor (48).

A10.7. The body-worn air-treatment device (10) of any of paragraphs A10-A10.6, further comprising a tether (50) interconnecting the body (12) and the anchor (48).

A11. The body-worn air-treatment device (10) of any of paragraphs A-A10.7, wherein the body (12) comprises an antimicrobial material (52).

A11.1. The body-worn air-treatment device (10) of paragraph A11, wherein the antimicrobial material (52) is at least one of embedded in the body (12) or applied to the exterior of the body (12).

A12. The body-worn air-treatment device (10) of any of paragraphs A-A11.1, wherein the at least one pathogen-deactivating mechanism (14) comprises at least one light source (54) supported by the body (12) and configured to emit light within a germicidal spectrum.

A12.1. The body-worn air-treatment device (10) of paragraph A12, wherein the at least one light source (54) is configured to emit the light within a/the nostril (112) of a/the nose (104) of the living individual (102) when the body (12) is operatively coupled relative to the nose (104).

A12.2. The body-worn air-treatment device (10) of any of paragraphs A12-A12.1, wherein the at least one light source (54) is configured to emit the light primarily, and optionally solely, within a single nostril (112) of a/the nose (104) of the living individual (102) when the body (12) is operatively coupled relative to the nose (104).

A12.2.1. The body-worn air-treatment device (10) of any of paragraphs A12-A12.2, wherein the at least one light source (54) comprises a first light source (54) configured to emit light primarily, and optionally solely, within a first nostril (112) of a/the nose (104) of the living individual (102) when the body (12) is operatively coupled relative to the nose (104) and a second light source (54) configured to emit light primarily, and optionally solely, within a second nostril (112) of the nose (104) of the living individual (102) when the body (12) is operatively coupled relative to the nose (104).

A12.3. The body-worn air treatment device (10) of paragraph A12, wherein the at least one light source (54) is configured to emit the light within an oral cavity of a/the mouth (106) of the living individual (102) when the body (12) is operatively coupled relative to a/the tooth (120) of the living individual.

A12.4. The body-worn air-treatment device (10) of any of paragraphs A12-A12.3, wherein the body (12) at least partially defines a/the void (28) radially inward from the body (12), and wherein the body (12) is shaped, and the at least one light source (54) is supported by the body (12) in a position, such that when the at least one light source (54) is activated, the light is directed to an entirety of the void (28).

A12.5. The body-worn air-treatment device (10) of any of paragraphs A12-A12.4, wherein the at least one light source (54) is configured to emit the light within a/the mouth (106) of the living individual (102) when the body (12) is operatively coupled proximate to the respiratory tract inlet (100) of the living individual (102).

A12.6. The body-worn air-treatment device (10) of any of paragraphs A12-A12.5, wherein the at least one light source (54) is configured to emit the light external and proximate to a nasal cavity (114) and/or a/the mouth (106) of the living individual (102) when the body (12) is operatively coupled proximate to the respiratory tract inlet (100) of the living individual (102).

A12.6.1. The body-worn air-treatment device (10) of paragraph A12.6, wherein the at least one light source (54) is configured to emit a curtain (55) of the light proximate to the nasal cavity (114) and/or a/the mouth (106) of the living individual (102) when the body (12) is operatively coupled proximate to the respiratory tract inlet (100) of the living individual (102).

A12.6.1.1. The body-worn air-treatment device (10) of paragraph A12.6.1, further comprising one or more of lenses (56) or reflectors (58) supported by the body (12) relative to the at least one light source (54) and configured to direct the light as the curtain (55) of the light.

A12.7. The body-worn air-treatment device (10) of any of paragraphs A12-A12.6.1.1, wherein the at least one light source (54) is supported by the body (12) such that the body (12) shields tissue of the living individual (102) from the light when the body (12) is operatively coupled proximate to the respiratory tract inlet (100) of the living individual (102).

A12.8. The body-worn air-treatment device (10) of any of paragraphs A12-A12.7, wherein the body (12) is shaped to shield tissue of the living individual (102) from the light when the body (12) is operatively coupled proximate to the respiratory tract inlet (100) of the living individual (102).

A12.8.1. The body-worn air-treatment device (10) of paragraph A12.8, wherein the body (12) defines a/the void (28) radially inward from the body (12), and wherein the at least one light source (54) is configured to emit the light solely within the void (28).

A12.8.2. The body-worn air-treatment device (10) of any of paragraphs A12.8-A12.8.1, wherein the body (12) defines a light trap (60), and wherein the at least one light source (54) is configured to emit the light solely within the light trap (60).

A12.9. The body-worn air-treatment device (10) of any of paragraphs A12-A12.8.2, wherein the body (12) defines a circuitous pathway (62), through which air is permitted to flow when the body (12) is operatively coupled proximate to the respiratory tract inlet (100) of the living individual (102), and wherein the at least one light source (54) is configured to emit the light throughout at least a substantial portion of the circuitous pathway (62).

A12.9.1. The body-worn air-treatment device (10) of paragraph A12.9, wherein the circuitous pathway (62) is fully within or substantially within a/the nostril (112) of a/the nose (104) of the living individual (102) when the body (12) is operatively coupled proximate to the respiratory tract inlet (100) of the living individual (102).

A12.9.2. The body-worn air-treatment device (10) of paragraph A12.9, wherein the circuitous pathway (62) extends within and outside of a/the nostril (112) of a/the nose (104) of the living individual (102) when the body (12) is operatively coupled proximate to the respiratory tract inlet (100) of the living individual (102).

A12.10. The body-worn air-treatment device (10) of any of paragraphs A12-A12.9.2, wherein the body (12) at least partially defines a/the void (28) radially inward from the body (12), wherein the body (12) comprises an inward surface (64) facing the void (28), and wherein the inward surface (64) is configured to reflect at least 20%, at least 40%, at least 60%, or at least 80% of the light.

A12.11. The body-worn air-treatment device (10) of any of paragraphs A12-A12.10, wherein the body (12) at least partially defines a/the void (28) radially inward from the body (12) and through which air is permitted to flow when the body (12) is operatively coupled proximate to the respiratory tract inlet (100) of the living individual (102), wherein the body (12) comprises a covering (70) extending across the void (28), and wherein the covering (70) is configured to permit air flow therethrough.

A12.11.1. The body-worn air-treatment device (10) of paragraph A12.11, wherein the covering (70) is further configured to restrict passage of visible light therethrough.

A12.11.2. The body-worn air-treatment device (10) of any of paragraphs A12.11-A12.11.1, wherein the covering (70) is further configured to restrict passage of UV light therethrough.

A12.11.3. The body-worn air-treatment device (10) of any of paragraphs A12.11-A12.11.2, wherein the covering (70) is further configured to restrict passage of near UVC light (230-280 nm) therethrough.

A12.11.4. The body-worn air-treatment device (10) of any of paragraphs A12.11-A12.11.3, wherein the void (28) has first and second longitudinally spaced ends regions (72), and further wherein the covering (70) extends across one of the first and the second longitudinally spaced end regions (72).

A12.11.5. The body-worn air-treatment device (10) of any of paragraphs A12.11-A12.11.4, wherein the covering (70) extends across both of the first and the second longitudinally spaced end regions (72).

A12.11.6. The body-worn air-treatment device (10) of any of paragraphs A12.11-A12.11.5, wherein the covering (70) encapsulates the body (12).

A12.12. The body-worn air-treatment device (10) of any of paragraphs A12-A12.11.6, wherein the at least one light source (54) is configured to emit light primarily, and optionally solely, within the germicidal spectrum.

A12.13. The body-worn air-treatment device (10) of any of paragraphs A12.11-A12.12, wherein the at least one light source (54) is configured to not emit light within the visible spectrum.

A12.14. The body-worn air-treatment device (10) of any of paragraphs A12-A12.13, wherein the at least one light source (54) comprises a light filter (74).

A12.14.1. The body-worn air-treatment device (10) of paragraph A12.14, wherein the light filter (74) is configured to prevent emission of visible light.

A12.14.2. The body-worn air-treatment device (10) of any of paragraphs A12.14-A12.14.1, wherein the light filter (74) is configured to prevent emission of light in the near UVC range (230-280 nm).

A12.15. The body-worn air-treatment device (10) of any of paragraphs A12-A12.14.2, wherein the at least one light source (54) is configured to emit light within the UV range.

A12.16. The body-worn air-treatment device (10) of any of paragraphs A12-A12.15, wherein the at least one light source (54) is configured to emit light within the UVC range.

A12.17. The body-worn air-treatment device (10) of any of paragraphs A12-A12.16, wherein the at least one light source (54) is configured to emit light solely within the UVC range.

A12.18. The body-worn air-treatment device (10) of any of paragraphs A12-A12.17, wherein the at least one light source (54) is configured to emit light within the far UVC range (205-230 nm).

A12.19. The body-worn air-treatment device (10) of any of paragraphs A12-A12.18, wherein the at least one light source (54) is configured to emit light solely within the far UVC range (205-230 nm).

A12.20. The body-worn air-treatment device (10) of any of paragraphs A12-A12.19, wherein the at least one light source (54) is configured to emit light having a wavelength of 222 nm.

A12.21. The body-worn air-treatment device (10) of any of paragraphs A12-A12.20, wherein at least a substantial portion of, and optionally all of, the light has a wavelength of 222 nm.

A12.22. The body-worn air-treatment device (10) of any of paragraphs A12-A12.21, wherein the at least one light source (54) is configured to emit lightly solely within a spectrum configured to not damage human tissue.

A12.23. The body-worn air-treatment device (10) of any of paragraphs A12-A12.22, wherein the at least one light source (54) comprises one or more LEDs (76) configured to emit the light within the germicidal spectrum.

A13. The body-worn air-treatment device (10) of any of paragraphs A-A12.23, wherein the at least one pathogen-deactivating mechanism (14) is configured to generate an electric field (77) through which air is permitted to flow when the body (12) is operatively coupled proximate to the respiratory tract inlet (100) of the living individual (102).

A13.1. The body-worn air-treatment device (10) of paragraph A13, wherein the electric field (77) is sufficient to deactivate pathogens.

A13.2. The body-worn air-treatment device (10) of any of paragraphs A13-A13.1, wherein the pathogen-deactivating mechanism (14) comprises an electroceutical fabric (78).

A13.2.1. The body-worn air-treatment device (10) of paragraph A13.2, wherein the body (12) at least partially defines a/the void (28) radially inward from the body (12) and through which air is permitted to flow when the body (12) is operatively coupled proximate to the respiratory tract inlet (100) of the living individual (102), and wherein the electroceutical fabric (78) spans the void (28).

A13.2.1.1. The body-worn air-treatment device (10) of paragraph A13.2.1, wherein the electroceutical fabric (78) comprises a plurality of plies (80) that spans the void (28).

A14. The body-worn air-treatment device (10) of any of paragraphs A-A13.2.1.1, wherein the body (12) is configured to support a power source (82) to power the at least one pathogen-deactivating mechanism (14).

A14.1. The body-worn air-treatment device (10) of paragraph A14, further comprising the power source (82).

A14.2. The body-worn air-treatment device (10) of any of paragraphs A14-A14.1, wherein the power source (82) comprises one or more batteries (84).

A14.3. The body-worn air-treatment device (10) of any of paragraphs A14-A14.2, wherein the power source (82) comprises one or more rechargeable batteries (84).

A14.3.1. The body-worn air-treatment device (10) of paragraph A14.3, wherein the one or more rechargeable batteries (84) are configured to be recharged via a contactless recharger.

A14.4. The body-worn air-treatment device (10) of any of paragraphs A14-A14.3.1, further comprising a charging port (66) supported by the body (12) and configured to be selectively coupled to an external power source for charging the power source (82).

A15. The body-worn air-treatment device (10) of any of paragraphs A-A14.4, further comprising a controller (85) supported by the body (12) and configured to one or more of:

regulate a voltage applied by a/the power source (82) to the at least one pathogen-deactivating mechanism (14);

regulate a current supplied by the power source (82) to the at least one pathogen-deactivating mechanism (14);

track a number of cycles that the at least one pathogen-deactivating mechanism (14) has been activated;

track a length of time that the at least one pathogen-deactivating mechanism (14) has been activated;

restrict activation of the at least one pathogen-deactivating mechanism (14) upon the at least one pathogen-deactivating mechanism (14) having been activated for a predetermined length of time;

restrict activation of the at least one pathogen-deactivating mechanism (14) upon the power source (82) falling below a predetermined power level;

restrict activation of the at least one pathogen-deactivating mechanism (14) based at least in part on criteria associated with efficacy of the at least one pathogen-deactivating mechanism (14);

generate an alert upon the at least one pathogen-deactivating mechanism (14) having been activated for a predetermined length of time;

generate an alert upon the power source (82) falling below a predetermined power level;

generate an alert based at least in part on criteria associated with efficacy of the at least one pathogen-deactivating mechanism (14); or determine a potential output of the power source (82) and to restrict activation of the at least one pathogen-deactivating mechanism (14) when the power source (82) does not have sufficient output to activate the at least one pathogen-deactivating mechanism (14) for a predetermined period of time.

A15.1. The body-worn air-treatment device (10) of paragraph A15, further comprising a user control (86) supported by the body (12) and operatively coupled to the controller (85).

A15.1.1. The body-worn air-treatment device (10) of paragraph A15.1, wherein the user control (86) is configured to permit a user to one or more of:

activate the at least one pathogen-deactivating mechanism (14);

deactivate the at least one pathogen-deactivating mechanism (14);

program the controller (85); or set an activation period of time for the at least one pathogen-deactivating mechanism (14).

A15.2. The body-worn air-treatment device (10) of any of paragraphs A15-A15.1.1, further comprising a wireless transceiver (88) and/or a wired connection port (90) supported by the body (12) and coupled to the controller (85), wherein the controller (85) is further configured send via the wireless transceiver (88) and/or the wired connection port (90) signals representative of one or more of:

a status of the power source (82);

a status of the at least one pathogen-deactivating mechanism (14);

the voltage across the power source (82);

the current able to be supplied by the power source (82);

the number of cycles that the at least one pathogen-deactivating mechanism (14) has been selectively activated;

the length of time that the at least one pathogen-deactivating mechanism (14) has been selectively activated; or a subsequent length of time the power source (82) is able to operatively power the at least one pathogen-deactivating mechanism (14).

A15.2.1. The body-worn air-treatment device (10) of paragraph A15.2, wherein the controller (85) is further configured to receive via the wireless transceiver (88) and/or the wired connection port (90) signals representative of instructions to one or more of:

activate the at least one power source (82);

deactivate the at least one power source (82);

program the controller (85); or set an/the activation period of time for the at least one pathogen-deactivating mechanism (14).

A15.2.2. The body-worn air-treatment device (10) of any of paragraphs A15.2-A15.2.1, in combination with non-transitory computer readable media (92) having computer executable instructions configured to cause a computing device to communicate with the controller (85) via the wireless transceiver (88) and/or the wired connection port (90).

A16. The body-worn air-treatment device (10) of any of paragraphs A-A15.2.2, further comprising an indicator (94) supported by the body (12) and configured to indicate a current status of the body-worn air-treatment device (10).

A16.1. The body-worn air-treatment device (10) of paragraph A16, wherein the indicator (94) comprises one or more of a visible indicator or an audible indicator.

A17. The body-worn air-treatment device (10) of any of paragraphs A-A16.1, further comprising a display (96) supported by the body (12) and configured to display information associated with the body-worn air-treatment device (10).

A18. The body-worn air-treatment device (10) of any of paragraphs A-A17, wherein the body (12) is configured to mate with, extend into, or otherwise nest or nestle with a specific portion or portions of the living individual (102) for operative retention of the device (10) on the living individual (102).

A19. The body-worn air-treatment device (10) of any of paragraphs A-18, wherein the body (12) comprises one or more sub-portions (65) that are sized and/or shaped to mate with, extend into, or otherwise nest or nestle with a/the specific portion or portions of the living individual (102) for operative retention of the device (10) on the living individual (102).

A19.1. The body-worn air-treatment device (10) of paragraph A19, wherein the one or more sub-portions (65) are configured to engage the specific portion or portions of the living individual (102) and restrict gravity from causing the device (10) to fall away from the living individual (102).

A19.2. The body-worn air-treatment device (10) of any of paragraphs A19-A19.1, wherein the one or more sub-portions (65) are configured to engage the specific portion or portions of the living individual (102) to cause an opposite region of the body (12) to wedge or be urged against another portion of the living individual (102), optionally against a distal region of a/the nostril (112).

A20. The body-worn air-treatment device (10) of any of paragraphs A18-A19.2 when depending from paragraph A1, wherein the specific portion or portions comprise a nasal vestibule of the living individual (102), and optionally a superior region of the nasal vestibule.

A21. The body-worn air-treatment device (10) of any of paragraphs A18-A20, wherein the one or more sub-portions (65) comprise a projection (67).

A21.1. The body-worn air-treatment device (10) of paragraph A21, whereon the projection (67) is narrowed relative to an adjacent portion of the body (12).

A22. The body-worn air-treatment device (10) of any of paragraphs A-A21.1, wherein the body (12) at least partially defines a/the void (28) radially inward from the body (12).

A22.1. The body-worn air-treatment device (10) of paragraph A22, wherein the body (12) defines a plurality of baffles (63) extending into the void (28) and configured to disrupt airflow through the void (28).

A22.1.1. The body-worn air-treatment device (10) of paragraph A22.1, wherein the plurality of baffles (63) define a/the circuitous pathway (62).

A22.1.2. The body-worn air-treatment device (10) of any of paragraphs A22.1-A22.1.1, wherein the baffles (63) are arcuate in shape and extend from opposing sides of the void (28).

A22.1.3. The body-worn air-treatment device (10) of any of paragraphs A22.1-A22.1.2, wherein the baffles (63) define a central channel region (332) between a first opening (334) and a second opening (336) to the void (28).

A22.2. The body-worn air-treatment device (10) of any of paragraphs A22-A22.1.3, wherein the body (12) has a first flared region (338) that at least partially defines a/the first opening (334) to the void (28).

A22.2.1. The body-worn air-treatment device (10) of paragraph A22.1, wherein the body (12) has a second flared region (339) that at least partially defines a/the second opening (336) to the void (28).

A22.2.2. The body-worn air-treatment device (10) of any of paragraphs A22.2-A22.2.1 when depending from paragraph A1, wherein the first flared region (338) is configured to nestle against an opening of the nose (104), and optionally an inferior side of the opening.

A23. The body-worn air-treatment device (10) of any of paragraphs A-A6.4, A8-A8.2, A10, A10.6-A17, wherein the body (12) is configured to be selectively coupled to a head (116) of the living individual (102).

A23.1. The body-worn air-treatment device (10) of paragraph A23, wherein the body (12) defines or forms a hat, a visor, a cap, a headband, other headwear, eyewear, glasses, or an eyewear frame (162).

A23.2. The body-worn air-treatment device (10) of any of paragraphs A23-A23.1, wherein the body (12) comprises:

a head mount (98) configured to be selectively and operatively coupled to the head (116); and optionally, a support (99) extending from the head mount (98), wherein the pathogen-deactivating mechanism (14) is at least partially supported by at least one of the head mount (98) and the support (99).

A23.2.1. The body-worn air-treatment device (10) of paragraph A23.2, wherein the pathogen-deactivating mechanism (14) comprises at least one/the light source (54) supported by the support (99) and configured to emit light within a/the germicidal spectrum.

A24. The body-worn air-treatment device (10) of paragraph A, further comprising any suitable subject matter from any of paragraphs A1-A23.2.1.

A25. Use of the body-worn air-treatment device (10) of any of paragraphs A-A24 to deactivate pathogens entering and/or exiting the respiratory tract inlet (100) of the living individual (102).

B. A body-worn air-treatment device (10), comprising:

a body (12) configured to be selectively coupled proximate a respiratory tract inlet (100) of a living individual (102); and a pathogen-deactivating mechanism (14) supported by the body (12);

wherein:

the body (12) is configured to be selectively coupled to a nose (104) of the living individual (102), and the pathogen-deactivating mechanism (14) is positioned to deactivate pathogens within the nose (104) of the living individual (102) as the pathogens pass the pathogen-deactivating mechanism (14) responsive to the living individual (102) breathing through the nose (104); or the body (12) is configured to be selectively coupled to a tooth (120) of the living individual (102), and the pathogen-deactivating mechanism (14) is positioned to deactivate pathogens within the mouth (106) of the living individual (102) as the pathogens pass the pathogen-deactivating mechanism (14) responsive to the living individual (102) breathing through the mouth (106); or the body (12) is configured to be selectively coupled to a head (116) of the living individual (102), the body (12) defines headwear, and the pathogen-deactivating mechanism (14) is positioned to deactivate pathogens as the pathogens enter and exit the nose (104) and the mouth (106) responsive to the living individual (102) breathing.

B1. The body-worn air-treatment device (10) of paragraph B, further comprising the subject matter of any of paragraphs A-A24.

B2. Use of the body-worn air-treatment device (10) of any of paragraphs B-B1 to deactivate pathogens entering and/or exiting the respiratory tract inlet (100) of the living individual (102).

C. A method (200), comprising deactivating (202) pathogens proximate a respiratory tract inlet (100) of a living individual (102).

C1. The method (200) of paragraph C, wherein the deactivating (202) comprises emitting (204) light within a germicidal spectrum proximate to the respiratory tract inlet (100) of the living individual (102).

C1.1. The method (200) of paragraph C1, wherein the emitting (204) comprises emitting the light within a nostril (112) of a nose (104) of the living individual (102).

C1.2. The method (200) of any of paragraphs C1-C1.1, wherein the emitting (204) comprises emitting the light within a mouth (106) of the living individual (102).

C1.3. The method (200) of paragraph C1, wherein the emitting (204) comprises emitting a curtain (55) of the light proximate to a nasal cavity (114) and/or a mouth (106) of the living individual (102).

C2. The method (200) of any of paragraphs C-C1.3, wherein the deactivating (202) comprises generating (206) an electric field (77), through which air flows proximate to the respiratory tract inlet (100) of the living individual (102) when the living individual (102) breathes.

C3. The method (200) of any of paragraphs C-C2, further comprising any suitable subject matter of any of paragraphs A-B1.

C4. The method (200) of any of paragraphs C-C3, wherein the method (200) is performed by the body-worn air-treatment device (10) of any of paragraphs A-B1.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa. Similarly, subject matter that is recited as being configured to perform a particular function may additionally or alternatively be described as being operative to perform that function.

As used herein, the term "and/or" placed between a first entity and a second entity means one of (1) the first entity, (2) the second entity, and (3) the first entity and the second entity. Multiple entries listed with "and/or" should be construed in the same manner, i.e., "one or more" of the entities so conjoined. Other entities optionally may be present other than the entities specifically identified by the "and/or" clause, whether related or unrelated to those entities specifically identified. Thus, as a non-limiting example, a reference to "A and/or B," when used in conjunction with open-ended language such as "comprising," may refer, in one example, to A only (optionally including entities other than B); in another example, to B only (optionally including entities other than A); in yet another example, to both A and B (optionally including other entities). These entities may refer to elements, actions, structures, steps, operations, values, and the like.

As used herein, the term "restrict," as used to describe a mechanism or action in opposition to a process or outcome, is intended to indicate that the mechanism or action operates to at least substantially, and optionally fully, diminish, block, and/or preclude the process or outcome from proceeding and/or being completed. As examples, the use of the term "restrict," such as in describing a mechanism as restricting visible light being emitted from light source 54, is intended to indicate that the mechanism impedes, blocks, obstructs, selectively prevents, and/or otherwise substantially limits visible light from being emitted from the device 10. As used herein, the term "prevent," as used to describe a mechanism or action in opposition to a process or outcome, is intended to indicate that the mechanism or action operates to fully block and/or preclude the process or outcome from proceeding and/or being completed during operative use of the structures and components according to the present disclosure. Thus, a mechanism that prevents visible light from being emitted from light source 54 precludes visible light from being emitted from light source 54, at least during intended operative use of the device 10. Stated differently, as used herein, the term "prevent" is not intended to indicate that the mechanism or action will fully block and/or preclude the process or outcome from proceeding and/or being completed in all possible uses, but rather is intended to indicate that the process or outcome is prevented at least when the structures and components disclosed herein are utilized in a manner consistent with the present disclosure.

As used herein, the term "substantial" or "substantially," when modifying a degree or relationship, includes not only the recited "substantial" degree or relationship, but also the full extent of the recited degree or relationship. A substantial amount of a recited degree or relationship may include at least 50%, and in some examples at least 75%, of the recited degree or relationship. For example, a device 10 that deactivates at least a substantial portion of pathogens being acted upon by the device includes a device 10 that deactivates 50% or 75% of the pathogens, as well as devices 10 that deactivate more than 50% or 75% of the pathogens, including 100% of the pathogens.

As used herein, the terms "selective" and "selectively," when modifying an action, movement, configuration, or other activity of one or more components or characteristics of an apparatus, mean that the specific action, movement, configuration, or other activity is a direct or indirect result of one or more dynamic processes, as described herein. The terms "selective" and "selectively" thus may characterize an activity that is a direct or indirect result of user manipulation of an aspect of, or one or more components of, the apparatus, or may characterize a process that occurs automatically, such as via the mechanisms disclosed herein.

As used herein, the phrase "at least one," in reference to a list of one or more entities should be understood to mean at least one entity selected from any one or more of the entities in the list of entities, but not necessarily including at least one of each and every entity specifically listed within the list of entities and not excluding any combinations of entities in the list of entities. This definition also allows that entities may optionally be present other than the entities specifically identified within the list of entities to which the phrase "at least one" refers, whether related or unrelated to those entities specifically identified. Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including entities other than B); in another embodiment, to at least one, optionally including more than one, B, with no A present (and optionally including entities other than A); in yet another embodiment, to at least one, optionally including more than one, A, and at least one, optionally including more than one, B (and optionally including other entities). In other words, the phrases "at least one," "one or more," and "and/or" are open-ended expressions that are both conjunctive and disjunctive in operation. For example, each of the expressions "at least one of A, B, and C," "at least one of A, B, or C," "one or more of A, B, and C," "one or more of A, B, or C," and "A, B, and/or C" may mean A alone, B alone, C alone, A and B together, A and C together, B and C together, A, B, and C together, and optionally any of the above in combination with at least one other entity.

As used herein, the phrase, "for example," the phrase, "as an example," and/or simply the term "example," when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

The various disclosed elements of apparatuses and steps of methods disclosed herein are not required to all apparatuses and methods according to the present disclosure, and the present disclosure includes all novel and non-obvious combinations and subcombinations of the various elements and steps disclosed herein. Moreover, one or more of the various elements and steps disclosed herein may define independent inventive subject matter that is separate and apart from the whole of a disclosed apparatus or method. Accordingly, such inventive subject matter is not required to be associated with the specific apparatuses and methods that are expressly disclosed herein, and such inventive subject matter may find utility in apparatuses and/or methods that are not expressly disclosed herein.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, when the disclosure or subsequently filed claims recite "a" or "a first" element or the equivalent thereof, such disclosure and/or claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements, and/or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

The invention claimed is:
1. A body-worn air-treatment device (10), comprising:
a body (12) configured to be selectively coupled proximate a respiratory tract inlet (100) of a living individual (102); and
a pathogen-deactivating mechanism (14) supported by the body (12);
wherein the body (12) is configured to be selectively coupled to a tooth (120) of the living individual (102), and the pathogen-deactivating mechanism (14) is positioned to deactivate pathogens within a mouth (106) of the living individual (102) as the pathogens pass the pathogen-deactivating mechanism (14) responsive to the living individual (102) breathing through the mouth (106); and
wherein the body (12) includes a band (44) configured to extend around the tooth (120).

2. The body-worn air-treatment device (10) of claim 1, wherein the body (12) is configured to be coupled to a palatal surface of the tooth (120) of the living individual (102).

3. The body-worn air-treatment device (10) of claim 1, wherein the tooth (120) is of an upper jaw of the living individual (102).

4. The body-worn air-treatment device (10) of claim 1, wherein the band (44) and the body (12) collectively define a cavity (46) sized to receive the tooth (120) of the living individual (102) therein.

5. The body-worn air-treatment device (10) of claim 1, wherein the band (44) has a length that is selectively adjustable.

6. The body-worn air-treatment device (10) of claim 1, wherein the body (12) includes a first sub-portion (65) that is configured to be coupled to a first surface of the tooth (120) and a second sub-portion (65) that is configured to be coupled to a second surface of the tooth (120), with the first and second surfaces of the tooth (120) being generally opposed to each other.

7. The body-worn air-treatment device (10) of claim 6, wherein the band (44) interconnects the first and second sub-portions (65).

8. The body-worn air-treatment device (10) of claim 6, wherein the band (44) includes wires (414) that establish electrical communication between the first sub-portion (65) and the second sub-portion (65).

9. The body-worn air-treatment device (10) of claim 1, wherein the body (12) includes a conformance layer (420) on a tooth-facing surface (422) of the body (12), and wherein the conformance layer (420) is formed from a resiliently compressible material.

10. The body-worn air-treatment device (10) of claim 1, wherein the body (12) defines a cavity (46) sized to receive at least a portion of the tooth (120) to couple the body (12) to the tooth (120).

11. The body-worn air-treatment device (10) of claim 1, wherein the pathogen-deactivating mechanism (14) comprises at least one light source (54) supported by the body (12) and configured to emit light within a germicidal spectrum.

12. The body-worn air-treatment device (10) of claim 11, wherein the at least one light source (54) is configured to emit light within the far UVC range (205-230 nanometers (nm)).

13. The body-worn air-treatment device (10) of claim 11, wherein the at least one light source (54) is configured to emit light solely within the far UVC range (205-230 nm).

14. The body-worn air-treatment device (10) of claim 11, wherein the at least one light source (54) comprises a light filter (74) configured to prevent emission of visible light.

15. The body-worn air-treatment device (10) of claim 11, wherein the at least one light source (54) comprises a light filter (74) configured to prevent emission of light in the near UVC range (230-280 nm).

16. The body-worn air-treatment device (10) of claim 1, further comprising a controller (85) supported by the body (12) and configured to one or more of:
regulate a voltage applied by a power source (82) to the pathogen-deactivating mechanism (14);
regulate a current supplied by the power source (82) to the pathogen-deactivating mechanism (14);
track a number of cycles that the pathogen-deactivating mechanism (14) has been activated;
track a length of time that the pathogen-deactivating mechanism (14) has been activated;
restrict activation of the pathogen-deactivating mechanism (14) upon the pathogen-deactivating mechanism (14) having been activated for a predetermined length of time;
restrict activation of the pathogen-deactivating mechanism (14) upon the power source (82) falling below a predetermined power level;
restrict activation of the pathogen-deactivating mechanism (14) based at least in part on criteria associated with efficacy of the pathogen-deactivating mechanism (14);
generate an alert upon the pathogen-deactivating mechanism (14) having been activated for a predetermined length of time;
generate an alert upon the power source (82) falling below a predetermined power level;
generate an alert based at least in part on criteria associated with efficacy of the pathogen-deactivating mechanism (14); or
determine a potential output of the power source (82) and to restrict activation of the pathogen-deactivating mechanism (14) when the power source (82) does not have sufficient output to activate the pathogen-deactivating mechanism (14) for a predetermined period of time.

17. A body-worn air-treatment device (10), comprising:
a body (12) configured to be selectively coupled proximate a respiratory tract inlet (100) of a living individual (102); and
a pathogen-deactivating mechanism (14) supported by the body (12);
wherein the body (12) is configured to be selectively coupled to a tooth (120) of the living individual (102), and the pathogen-deactivating mechanism (14) is positioned to deactivate pathogens within a mouth (106) of the living individual (102) as the pathogens pass the pathogen-deactivating mechanism (14) responsive to the living individual (102) breathing through the mouth (106); and
wherein the body (12) comprises a magnet (34) configured to couple the body (12) relative to the tooth (120).

18. A body-worn air-treatment device (10), comprising:
a body (12) configured to be selectively coupled proximate a respiratory tract inlet (100) of a living individual (102); and a pathogen-deactivating mechanism (14) supported by the body (12);

wherein the body (12) is configured to be selectively coupled to a tooth (120) of the living individual (102), and the pathogen-deactivating mechanism (14) is positioned to deactivate pathogens within a mouth (106) of the living individual (102) as the pathogens pass the pathogen-deactivating mechanism (14) responsive to the living individual (102) breathing through the mouth (106); and wherein the body-worn air-treatment device (10) further comprises an anchor (48) configured to be secured to the tooth (120), and wherein the body (12) is configured to be removably coupled to the anchor (48).

19. The body-worn air-treatment device (10) of claim 18, wherein the anchor (48) comprises an orthodontic appliance (148) or a dental implant.

20. The body-worn air-treatment device (10) of claim 18, wherein the anchor (48) is configured to be adhesively bonded to the tooth (120).

21. The body-worn air-treatment device (10) of claim 18, wherein the anchor (48) is configured to extend at least partially around the tooth (120).

22. A method (200), comprising deactivating (202) pathogens proximate a respiratory tract inlet (100) of a living individual (102) within a nese (104) er a mouth (106) of the living individual as the living individual (102) breathes, wherein the deactivating (202) is performed by an intra-body-worn air-treatment device (10) that comprises:

a body (12) configured to be selectively coupled proximate the respiratory tract inlet (100) of the living individual (102); and a pathogen-deactivating mechanism (14) supported by the body (12);

wherein the body (12) is configured to be selectively coupled to a tooth (120) of the living individual (102), and the pathogen-deactivating mechanism (14) is positioned to deactivate pathogens within the mouth (106) of the living individual (102) as the pathogens pass the pathogen-deactivating mechanism (14) responsive to the living individual (102) breathing through the mouth (106); and wherein:

the body (12) includes a band (44) configured to extend around the tooth (120); or the body (12) comprises a magnet (34) configured to couple the body (12) relative to the tooth (120); or the body-worn air-treatment device (10) further comprises an anchor (48) configured to be secured to the tooth (120), and wherein the body (12) is configured to be removably coupled to the anchor (48).

* * * * *

UNITED STATES PATENT AND TRADEMARK OFFICE
CERTIFICATE OF CORRECTION

| | | |
|---|---|---|
| PATENT NO. | : 12,172,039 B2 | Page 1 of 1 |
| APPLICATION NO. | : 18/477269 | |
| DATED | : December 24, 2024 | |
| INVENTOR(S) | : Joseph W. Bingold et al. | |

It is certified that error appears in the above-identified patent and that said Letters Patent is hereby corrected as shown below:

In the Claims

Claim 22, Column 43, Line 26, after "individual (102) within" please delete "a nese (104) er".

Signed and Sealed this
Fourth Day of February, 2025

Coke Morgan Stewart
*Acting Director of the United States Patent and Trademark Office*